(12) United States Patent
Shen et al.

(10) Patent No.: US 9,662,324 B2
(45) Date of Patent: May 30, 2017

(54) METHODS AND COMPOSITIONS FOR TREATING β-THALASSEMIA AND SICKLE CELL DISEASE

(71) Applicant: Academia Sinica, Taipei (TW)

(72) Inventors: Che-Kun James Shen, Taipei (TW); Yu-Chi Chou, Taipei (TW); Tsann-Long Su, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/787,885

(22) PCT Filed: May 1, 2014

(86) PCT No.: PCT/US2014/036369
§ 371 (c)(1),
(2) Date: Oct. 29, 2015

(87) PCT Pub. No.: WO2014/179567
PCT Pub. Date: Nov. 6, 2014

(65) Prior Publication Data
US 2016/0106728 A1    Apr. 21, 2016

Related U.S. Application Data

(60) Provisional application No. 61/818,058, filed on May 1, 2013.

(51) Int. Cl.
| | |
|---|---|
| *A61K 31/473* | (2006.01) |
| *A61K 9/00* | (2006.01) |
| *A61K 45/06* | (2006.01) |
| *G01N 33/50* | (2006.01) |
| *C07D 221/14* | (2006.01) |

(52) U.S. Cl.
CPC .......... *A61K 31/473* (2013.01); *A61K 9/0053* (2013.01); *A61K 45/06* (2013.01); *C07D 221/14* (2013.01); *G01N 33/5044* (2013.01); *G01N 2333/805* (2013.01); *G01N 2800/52* (2013.01)

(58) Field of Classification Search
CPC .. A61K 31/473; A61K 9/0053; C07D 221/14; G01N 33/5044
USPC ....................................................... 514/296
See application file for complete search history.

(56) References Cited

U.S. PATENT DOCUMENTS

| 8,822,491 B2 | 9/2014 | Shen et al. |
| 2008/0234342 A1 | 9/2008 | Granger et al. |
| 2010/0272660 A1 | 10/2010 | Malle |
| 2010/0303719 A1 | 12/2010 | Huang et al. |

FOREIGN PATENT DOCUMENTS

| CN | 1328549 A | 12/2001 | |
| CN | 1330638 A | 1/2002 | |
| DE | WO 0031039 A1 * | 6/2000 | ........... C07D 221/14 |
| EP | 0 604 181 A1 | 6/1994 | |
| EP | 1323711 A1 | 7/2003 | |
| KR | 2000-0052949 A | 8/2000 | |
| KR | 2009-0026141 A | 3/2009 | |
| WO | WO 99/11649 A2 | 3/1999 | |
| WO | WO 2013/057592 A2 | 4/2013 | |

OTHER PUBLICATIONS

Zein et al., Experimental Biology and Medicine 2010, 235, p. 1385-1394.*
Chakalova et al. Blood (2005) 105(5) p. 2154-2160.*
Corcoran et al., A novel action of histone deacetylase inhibitors in a protein aggresome disease model. Curr Biol. Mar. 23, 2004;14(6):488-92.
Tokumitsu et al., STO-609, a specific inhibitor of the Ca(2+)/calmodulin-dependent protein kinase kinase. J Biol Chem. May 3, 2002;277(18):15813-8. Epub Feb. 26, 2002. Erratum in: J Biol Chem. Feb. 7, 2003;278(6):4368.
Wang et al., Scriptaid, a novel histone deacetylase inhibitor, protects against traumatic brain injury via modulation of PTEN and AKT pathway : scriptaid protects against TBI via AKT. Neurotherapeutics. Jan. 2013;10(1):124-42.
Norton et al., Synthesis and anticancer activities of 6-amino amonafide derivatives. Anticancer Drugs. Jan. 2008;19(1):23-36.

\* cited by examiner

*Primary Examiner* — Yong Chu
(74) *Attorney, Agent, or Firm* — Wolf, Greenfield & Sacks, P.C.

(57) ABSTRACT

Compounds, pharmaceutical compositions, and methods for treating anemia (β-thalassemia anemia or sickle cell anemia.

16 Claims, 18 Drawing Sheets

Compound B1

Compound B4

Compound E3

METHODS AND COMPOSITIONS FOR TREATING β-THALASSEMIA AND SICKLE CELL DISEASE

RELATED APPLICATIONS

This application is a national stage filing under 35 U.S.C. 371 of International Application PCT/US2014/036369 entitled "METHODS AND COMPOSITIONS FOR TREATING BETA-THALASSEMIA AND SICKLE CELL DISEASE" filed May 1, 2014, which claims the benefit of U.S. provisional application No. 61/818,058, filed May 1, 2013, the entire disclosure of each of which is incorporated by reference herein in its entirety.

BACKGROUND OF THE INVENTION

The human hemoglobin molecule consists of a protein heterotetramer (two α-like globin chains and two β-like globin chains) and four non-protein heme groups. The α-like and β-like globin gene clusters are located on different chromosomes, and expression of the different globin genes within the two gene clusters are under temporal control during development. Genetic defects, such as deletions or mutations, inside these globin gene loci result in abnormal synthesis of hemoglobins and consequently lead to hemoglobinopathies. Weatherall D J, *Nat Rev Genet.* 2001;2(4):245-255.

β-thalassemia and sickle cell disease are the two most common hemoglobinopathies, which together affect approximately 4.5% of populations worldwide. Patrinos et al., *Hemoglobin.* 2008;32(1-2):229-236. β-thalassemia is the result of either a deletion or mutation within the β-like globin gene cluster, diminishing the synthesis of adult β globin chain. Severe deficiency or absence of the β globin chain leads to imbalanced expression of the adult α globin chain and the overloaded α globin chain in turn precipitates and damages the red cell membrane, ultimately inducing rapid apoptosis of the erythrocytes during early erythroblast development (also termed β-thalassemia major or Cooley's anemia). Individuals with β-thalassemia major become profoundly anemic within 6 to 9 months after birth, the time when the hemoglobin switch is completed from HbF (α2/γ2) to HbA (α2/β2).

Sickle cell disease is caused by a point mutation at the sixth position of the β globin chain (from Glu to Val). Patients with sickle cell disease are characterized by the existence of sickle hemoglobin HbS (α2/$β^S$2). The mutated adult β globin chain promotes the polymerization of HbS at low oxygen condition, which distorts the red blood cells into the characteristic sickle shape. Schechter A N, *Blood.* 2008; 112(10):3927-3938.

The illness of sickle cell disease is primarily caused by hemolysis, since the misshaped sickle cells are destroyed inside the spleen within 10-20 days. With high risk of early death, life expectancy of patients with the sickle cell disease is reported to be shortened to an average of 42-48 years. Impairing the generation of normal adult hemoglobin, both β-thalassemia major and sickle cell disease patients require regular blood transfusion to replenish functional HbA for survival. However, constant transfusions are accompanied by a high cost (exceeding 1 billion US dollars per year in the US alone) and a high risk of iron overloading which often leads to death.

In both β-thalassemia and sickle cell disease, the elevated expression of HbF has been reported to be helpful in improving the clinical symptoms of the underlying diseases. In β-thalassemia major patients, elevation of the fetal γ globin chain synthesis balances the excess α globin chains by formation of HbF, thus modulating the severe anemia in patients. Natta et al., *J Clin Invest.* 1974;54(2):433-438.

Moreover, the increase of the γ globin chain can also prevent the formation of HbS, and the existence of HbF directly inhibits the polymerization of HbS in the sickle cell patients. Noguchi et al., *N Engl J Med.* 1988;318(2):96-99.

Thus, pharmacological induction of HbF in patients with hemoglobinopathies is a potentially useful therapeutic strategy. To date, several chemotherapeutic agents, such as trichostatin A (histone deacetylase inhibitor), apicidin (histone deacetylase inhibitor), 5'-aza-cytidine (DNA methyltransferase inhibitor), hydroxyurea (ribonucleotide reductase inhibitor), butyrate and other short-chain fatty acids, have been demonstrated to stimulate fetal hemoglobin production. Ley et al., *Annu Rev Med.* 1985;36:485-498; Humphries et al., *J Clin Invest.* 1985;75(2):547-557; Olivieri et al., *Hum Mol Genet.* 1998;7(10):1655-1658; McCaffrey et al., *Blood.* 1997;90(5):2075-2083; Witt et al., *Blood.* 2003;101(5):2001-2007; and Constantoulakis et al., *Blood.* 1989;74(6):1963-1971.

However, most of these HbF inducers show variable efficacies from individual to individual, low specificity in globin gene induction, and high toxicity with irreversible apoptosis. Among these drugs, hydroxyurea is the first US FDA-approved medicine for the curing of hemoglobinopathies disease. Unfortunately, approximately 25% of the recipients are poor or non-responders to hydroxyurea treatment. Moreover, potential side effects of myelosuppression and reproductive toxicity exist, leading to therapeutic concerns for the usage of hydroxyurea in patients. Grigg A., *Intern Med J* 2007;37(3):190-192; Kinney et al., *Blood.* 1999;94(5):1550-1554; Steinberg et al., *Blood.* 1997;89(3):1078-1088; and Atweh et al., *Hematol Oncol Clin North Am.* 2010;24(6):1131-1144.

In view of this, compounds that induce expression of endogenous embryonic/fetal globin chains for the treatment of β-thalassemia major and sickle cell diseases are of great clinical interest.

SUMMARY OF THE INVENTION

The present disclosure is based on the unexpected discovery of novel compounds that possess the activity of inducing the expression of endogenous embryonic/fetal globin (e.g., γ globin) in erythrycoytes. Accordingly, the present disclosure provides compositions and methods for the treatment of anemia such as β-thalassemia or sickle cell disease through at least the induction of the globin gene expression in erythrycoytes. The methods described herein comprise the administration of a pharmaceutical composition to a subject comprising a therapeutically effective amount of a compound of the present disclosure effective to treat, delay or prevent the adverse effects of β-thalassemia or sickle cell disease. In certain embodiments, a therapeutically effective amount of a compound described herein is effective for inducing the expression of embryonic/fetal globin genes.

In some embodiments, pharmaceutical compositions of compounds for the treatment of β-thalassemia or sickle cell disease through induction of endogenous embryonic/fetal globin chains are provided. Provided compositions comprise an effective amount of a compound as described herein, and a pharmaceutically acceptable excipient. In other embodiments, compounds possessing the property of inducing expression of endogenous embryonic/fetal globin chains in erythroid cells may be present in a mammalian host, or in culture as an in vitro model.

One aspect of the present disclosure is a compound represented by Formula A:

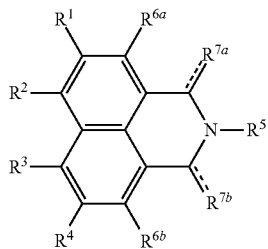

or a pharmaceutically acceptable salt, solvate, or hydrate thereof.

$R^1$, $R^2$, $R^3$, $R^4$, $R^{6a}$, and $R^{6b}$ are each independently selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$.

$R^5$ is hydrogen, optionally substituted alkyl, optionally substituted alkenyl, optionally substituted alkynyl, optionally substituted heterocyclyl, optionally substituted heteroaryl, or optionally substituted aryl.

$R^{7a}$ and $R^{7b}$ are each independently selected from the group consisting of hydrogen, oxygen, hydroxyl, —OR, and —OC(=O)R wherein the symbol ===== represents a double bond when $R^{7a}$ and $R^{7b}$ is oxygen atom or a single bond when $R^{7a}$ and $R^{7b}$ is a hydrogen, hydroxyl, —OR, or —OC(=O)R. R is optionally substituted alkyl, optionally substituted alkenyl, optionally substituted alkynyl, optionally substituted heterocyclyl, optionally substituted heteroaryl, and optionally substituted aryl.

Each instance of $R^A$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl.

Each instance of $R^B$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl, or two $R^B$ are taken together with the intervening atoms to form a heterocycle.

In some embodiments, the present disclosure provides a compound of Formula (I-a):

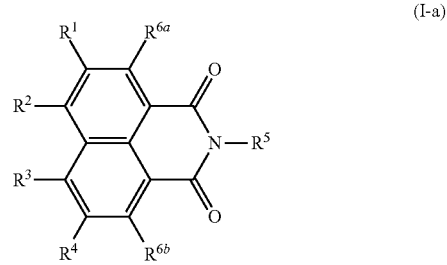

or a pharmaceutically acceptable salt, solvate, or hydrate thereof, wherein $R^1$, $R^2$, $R^3$, $R^4$, $R^5$, $R^{6a}$, and $R^{6b}$ are as defined herein. In another aspect, provided herein is a pharmaceutical composition comprising a compound of Formula (I-a) and a pharmaceutically acceptable carrier or diluent.

In other embodiments, the present disclosure provides a compound of Formula (V-a):

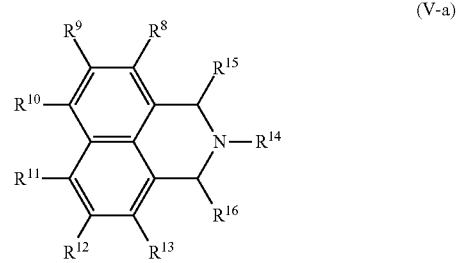

or a pharmaceutically acceptable salt, solvate, or hydrate thereof, wherein $R^{89}$, $R^9$, $R^{10}$, $R^{11}$, $R^{12}$, $R^{13}$, $R^{14}$, $R^{15}$, and $R^{16}$ are as defined herein. Also provided herein is a pharmaceutical composition comprising a compound of Formula (V-a) and a pharmaceutically acceptable carrier or diluent.

Another aspect of the present disclosure provides a pharmaceutical composition, which comprises one or more of the compounds disclosed herein (e.g., one or more of compounds of Formula A, (I-a), (II), (III), (III-a), (III-b), (VI), (V-a), (VI), (VI-a), (VII), (VII-a), (VIII), (VIII-a), (IX), (IX-a), (X), (X-a), (XI), and/or (XI-a)) and a pharmaceutically acceptable carrier.

Further, the present disclosure provides a method of treating a subject with β-thalassemia or sickle cell anemia. The method comprises administering an effective amount of a pharmaceutical composition to the subject in need thereof, wherein the composition comprises a compound disclosed herein (e.g., a compound of Formula A, (I-a), (II), (III), (III-a), (III-b), (VI), (V-a), (VI), (VI-a), (VII), (VII-a), (VIII), (VIII-a), (IX), (IX-a), (X), (X-a), (XI), and/or (XI-a))) or a pharmaceutically acceptable salt thereof, and a pharmaceutically acceptable carrier.

In another aspect, the present disclosure provides methods of inducing γ globin comprising contacting a cell with a compound or composition provided herein. In certain embodiments, the contacting step is performed in vitro. In other embodiments, the contacting step is performed in vivo. In certain embodiments, the present disclosure provides a method of treating β-thalassemia comprising administering an effective amount of a compound or composition provided herein to a patient in need thereof. In other embodiments, the present disclosure provides a method of treating sickle cell anemia comprising administering an effective amount of a compound or composition provided herein to a patient in need thereof.

Also within the scope of the present disclosure are pharmaceutical compositions for use in treating β-thalassemia or sickle cell anemia, the composition comprising one or more of the compounds described herein and a pharmaceutically acceptable carrier, as well as uses of such compounds or compositions in manufacturing a medicament for use in treating the anemia.

Further, the present disclosure provides a method for assessing responsiveness of a subject (e.g., a human patient) to a hydroxyurea. The method comprises (i) providing a sample derived from the subject, the sample comprising adult erythroid cells, which are treated by the hydroxyurea, (ii) measuring the expression level of a hemoglobin gene in the erythroid cells, and identifying the subject as being responsive to the hydroxyurea if the expression level of the hemoglobin in the adult erythorid cells is elevated as compared to adult erythroid cells not treated by the hydroxyurea, and identifying the subject as being not responsive to the hydroxyurea if the expression level of the hemoglobin in the adult erythorid cells is unchanged or redued as compared to adult erythroid cells not treated by the hydroxyurea. In some examples, the hemoglobin gene is a fetal hemoglobin (HbF) gene. In other examples, the hydroxyurea is administered to the subject. A subject identified as being inresponsive to the hydroxyurea may be treated by a different anti-anemia therapeutic agent, such as the compounds disclosed herein.

The details of one or more embodiments of the disclosure are set forth in the description below. Other features or advantages of the present disclosure will be apparent from the following drawings and detailed description of several embodiments, and also from the appended claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, a "hydrocarbon chain" refers to a substituted or unsubstituted divalent alkyl, alkenyl, or alkynyl group. A hydrocarbon chain includes at least one chain, each node ("carbon unit") of which including at least one carbon atom between the two radicals of the hydrocarbon chain. For example, hydrocarbon chain —C$^A$H(C$^B$H$_2$C$^C$H$_3$)— includes only one carbon unit C$^A$. The term "C$_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

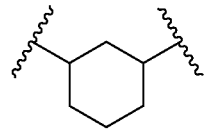 [SMILES: *C1CCCC(*)C1]

is a C$_3$ hydrocarbon chain. When a range of values is used, e.g., a C$_{1-6}$hydrocarbon chain, the meaning of the range is as described herein. A hydrocarbon chain may be saturated (e.g., —(CH$_2$)$_4$—). A hydrocarbon chain may also be unsaturated and include one or more C═C and/or C≡C bonds anywhere in the hydrocarbon chain. For instance, —CH═CH—(CH$_2$)$_2$—, —CH$_2$—C≡C—CH$_2$—, and —C≡C—CH═CH— are all examples of a unsubstituted and unsaturated hydrocarbon chain. In certain embodiments, the hydrocarbon chain is unsubstituted (e.g., —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

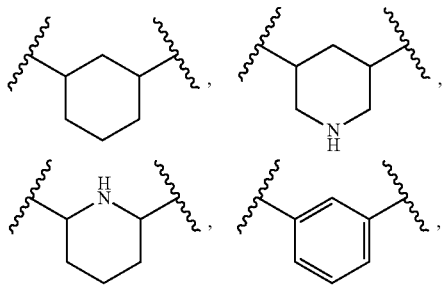

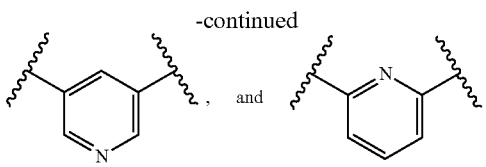

are all examples of a hydrocarbon chain. In contrast, in certain embodiments

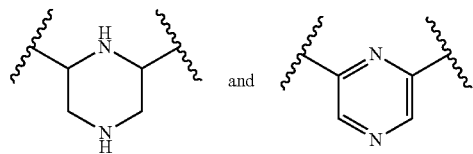 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused toone or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur. In some embomdients, the 5-6 membered heterocyclyl is further substituted with another heterocyclic ring, which is optionally substituted Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl, and thiepanyl. Exemplary 8-membered heterocyclyl groups containing one heteroatom include, without limitation, azocanyl, oxecanyl, and thiocanyl. Exemplary 5-membered heterocyclyl groups fused to a C$_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like. Exemplary 5-6 membered heterocyclyl which is further substituted with another heterocyclic ring, which is optionally substituted include, without limitation, 4-piperidinopiperidine.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen, and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Alkyl, alkenyl, alkynyl, carbocyclyl, heterocyclyl, aryl, and heteroaryl groups, as defined herein, which are divalent bridging groups are further referred to using the suffix—ene, e.g., alkylene, alkenylene, alkynylene, carbocyclylene, heterocyclylene, arylene, and heteroarylene.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —O$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from the group consisting of hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electrostaticneutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)$R^{aa}$, —CHO, —CO$_2 R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2 R^{aa}$, —C(=S)N($R^{bb}$)$_2$, —C(=O)S$R^{aa}$, and —C(=S)S$R^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2 R^{aa}$, —SO$_2 R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2 R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2 R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2 R^{aa}$, —SO$_2 R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2 R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2 R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)phenylmethyl, tri (ryl, triphenylmethyl, α-naphthyldiphenylmethyl, M), 2,2, 2-trichloroethoxymethyl, bis(2 - chloroethoxy) metlinoyloxyphenyl)methyl, 4,4',4''-tris(benzoyloxyphenyl) methyl, 3-(imidazol-1-yl)bis(4',4''-dimethoxyphenyl) methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, t-butyl carbonate (BOC), alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl) benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N, N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R^{aa}$, —$Si(R^{aa})_3$, —$P(R^{cc})_2$, —$P(R^{cc})_3$, —P(=O)$_2R^{aa}$, —P(=O)$(R^{aa})_2$, —P(=O)$(OR^{cc})_2$, —P(=O)$_2N(R^{bb})_2$, and —P(=O)$(NR^{bb})_2$, wherein $R^{aa}$, $R^{bb}$, and $R^{cc}$ are as defined herein. Sulfur protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Figures, Examples, and Claims. The disclosure is not intended to be limited in any manner by the above exemplary listing of substituents.

As used throughout, "modulation" is meant to refer to an increase or a decrease in the indicated phenomenon (e.g., modulation of a biological activity refers to an increase in a biological activity or a decrease in a biological activity).

As used herein, the terms "treatment," "treating," and the like, refer to obtaining a desired pharmacologic and/or physiologic effect. The effect may be prophylactic in terms of completely or partially preventing a disease or condition, or symptom thereof, and/or may be therapeutic in terms of a partial or complete cure for a condition and/or adverse affect attributable to the condition. "Treatment," as used herein, covers any treatment of a disease or condition in a mammal, particularly in a human, and includes: (a) reducing the risk for developing the condition from occurring in a subject which may be predisposed to the condition but has not yet been diagnosed as having it; (b) inhibiting the development of the condition; and/or (c) relieving the condition, i.e., causing its regression.

An "effective amount" is an amount sufficient to effect beneficial or desired results. An effective amount can be administered in one or more administrations. An effective amount corresponds with the quantity required to provide a desired average local concentration of a particular biologic agent, in accordance with its known efficacy, for the intended period of therapy. A dose may be determined by those skilled in the art by conducting preliminary animal studies and generating a dose response curve, as is known in the art. Maximum concentration in the dose response curve would be determined by the solubility of the compound in the solution and by toxicity to the animal model, as known in the art.

The effective amount further corresponds with the quantity required to provide a desired average local concentration of the particular biologic agent, in accordance with its efficacy for the intended period of time. Due allowance can be made for losses due to circulatory fluctuation due to physical activity, for example, from ten to ninety percent loss allowance could be made depending upon the individual patient and their routines.

The terms "individual," "subject," "host," and "patient," used interchangeably herein, refer to a mammal, including, but not limited to, humans, murines, simians, felines, canines, equines, bovines, mammalian farm animals, mammalian sport animals, and mammalian pets. Human subjects are of particular interest.

As used herein, the terms "determining", "assessing", "assaying", "measuring" and "detecting" refer to both quantitative and qualitative determinations and as such, the term "determining" is used interchangeably herein with "assaying," "measuring," and the like. Where a quantitative determination is intended, the phrase "determining an amount" and the like is used. Where either a qualitative or quantitative determination is intended, the phrase "determining a level of proliferation" or "detecting proliferation" is used.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry," Thomas Sorrell, University Science Books, Sausalito: 1999, the entire contents of which are incorporated herein by reference.

Certain compounds of the present disclosure may exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

Isomeric mixtures containing any of a variety of isomer ratios may be utilized in accordance with the present disclosure. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present disclosure. Those of ordinary skill in the art will readily appreciate that analogous ratios are contemplated for more complex isomer mixtures.

If, for instance, a particular enantiomer of a compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycyclic heterocycle. The heterocycle may also be fused to a spirocyclic group. In some cases, the heterocycle may be attached to a compound via a nitrogen or a carbon atom in the ring. The heterocycle may be substituted with another heterocycle.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamnethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle is substituted with another heterocycle (e.g., 4-piperidinopiperidine or the like). In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The term "amino," as used herein, refers to a primary (—NH$_2$), secondary (—NHR$_x$), tertiary (—NR$_x$R$_y$), or quaternary (—N$^+$R$_x$R$_y$R$_z$) amine, where R$_x$, R$_y$, and R$_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the disclosure contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "aryloxy" refers to the group, —O-aryl. The term "acyloxy" refers to the group, —O-acyl.

The term "alkoxyalkyl" refers to an alkyl group substituted with at least one alkoxy group (e.g., one, two, three, or more, alkoxy groups). For example, an alkoxyalkyl group may be -(C$_{1-6}$-alkyl)—O—(C$_{1-6}$-alkyl), optionally substituted. In some cases, the alkoxyalkyl group may be optionally substituted with another alkyoxyalkyl group (e.g., -($C_{1-6}$-alkyl)—O—($C_{1-6}$-alkyl)—O—($C_{1-6}$-alkyl), optionally substituted.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like. When there is a position on the compounds that can be substituted with alkyl, the compounds can be substituted at that position with a haloalkyl in certain embodiments.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceeded by the term "optionally" or not, and substituents contained in formulas of this disclosure, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valencies of the heteroatoms. Furthermore, this disclosure is not intended to be limited in any manner by the permissible substituents of organic compounds. Combinations of substituents and variables envisioned by this disclosure are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

Any of the compounds described herein may be in a variety of forms, such as, but not limited to, salts, solvates, hydrates, tautomers, and isomers.

The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, loweralkyl sulfonate and aryl sulfonate.

In certain embodiments, the compound is in the form of a hydrate or solvate. The term "hydrate" as used herein refers to a compound non-covalently associated with one or more molecules of water. Likewise, the term "solvate" refers to a compound non-covalently associated with one or more molecules of an organic solvent.

In certain embodiments, the compound described herein may exist in various tautomeric forms. The term "tautomer" as used herein includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

In certain embodiments, the compounds described herein may exist in various isomeric forms. The term "isomer" as used herein includes any and all geometric isomers and stereoisomers (e.g., enantiomers, diasteromers, etc.). For example, "isomer" includes cis- and trans-isomers, E- and Z-isomers, R- and S-enantiomers, diastereomers, (D)-isomers, (L)-isomers, racemic mixtures thereof, and other mixtures thereof, as falling within the scope of the disclosure. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present disclosure is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The present disclosure provides the endogenous embryonic/fetal globin chain inducers in a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration is achieved in various ways. In some formulations, the inducers are systemic after administration; in others, the inhibitor is localized by virtue of the formulation, such as the use of an implant that acts to retain the active dose at the site of implantation.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the present disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned hereunder are incorporated herein by reference. Unless mentioned otherwise, the techniques employed herein are standard methodologies well known to one of ordinary skill in the art.

It must be noted that as used herein and in the appended claims, the singular forms "a," "and," and "the" include plural referents unless the context clearly dictates otherwise. Thus, for example, reference to "a biomarker" includes a plurality of such biomarkers and reference to "the sample" includes reference to one or more samples and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Moreover any positively recited element of the disclosure provides basis for a negative limitation to exclude that element from the claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

Other objects, features and advantages of the present disclosure will become apparent from the following detailed description. It should be understood, however, that the detailed description and specific examples, while indicating preferred embodiments of the disclosure, are given by way of illustration only, since various changes and modifications within the spirit and scope of the disclosure will become apparent to those skilled in the art from this detailed description.

DETAILED DESCRIPTION OF THE INVENTION

Figure 1:
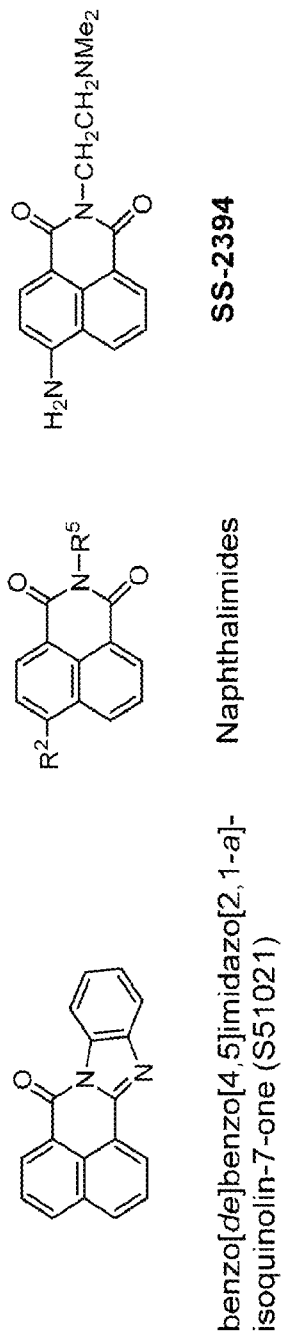
FIG. 1 shows the structures of S51021, naphthalimides, and SS-2394.

The present disclosure stems, in part, from the unexpected discovery that a number of small molecules were found to induce γ globin gene expression. The compounds identified herein are useful for treatment of β-thalassemia or sickle cell disease through induction of endogenous embryonic/fetal globin chains. Accordingly, disclosed herein are compounds capable of inducing γ globin gene expression and uses thereof in treating anemia such as β-thalassemia or sickle cell disease.

Compounds Capable of Inducing γ Globin Gene Expression

In one embodiment, the compound is represented by structural formula A, I, I-a, II, III, IV, III-a, III-b, (V-a), (VI), (VI-a), (VII), (VII-a), (VIII), (VIII-a), (IX), (IX-a), (X), (X-a), (XI), and/or (XI-a) wherein the values for the variables are as defined herein.

Compounds of interest include naphthalimides, e.g., compounds that include a naphthalimide scaffold substituted with one or more substituents, which are non-hydrogen. The naphthalimide scaffold of Formula (I) may be substituted at any position 1, 2, 3, 4, 5, 6, and/or 7 shown below.

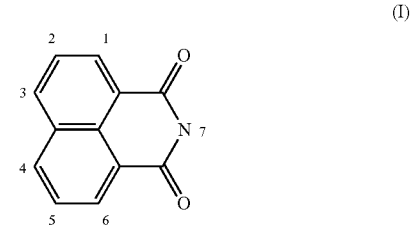 [SMILES: O=C1NC(=O)c2cccc3cccc1c23]

(I)

In certain embodiments, positions 3 and 4 of the naphthalimide scaffold are substituted. In certain embodiments, position 3 of the naphthalimide scaffold is substituted. In certain embodiments, positions 3, 4, and 7 of the naphthalimide scaffold are substituted. In certain embodiments, positions 3 and 7 of the naphthalimide scaffold are substituted.

In certain embodiments, a substituent may contribute to optical isomerism and/or stereo isomerism of a compound. The compound(s) of the present disclosure provided herein include the neutral form, salts, solvates, hydrates, and prodrug forms of a compound. All such forms are embraced by the present disclosure. Thus the compounds described herein include salts, solvates, hydrates, prodrug, and isomer forms thereof, including the pharmaceutically acceptable salts, solvates, hydrates, prodrugs, and isomers thereof. In certain embodiments, a compound may be a metabolized into a pharmaceutically active derivative.

In certain embodiments, the present disclosure employs a compound of Formula (I-a):

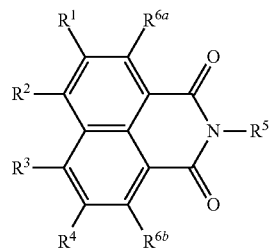

(I-a)

or a pharmaceutically acceptable salt, solvate, or hydrate thereof,
wherein:

$R^1$, $R^2$, $R^3$, $R^4$, $R^{6a}$, and $R^{6b}$ are each independently selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$;

$R^5$ is hydrogen, optionally substituted alkyl, optionally substituted alkenyl, optionally substituted alkynyl, optionally substituted heterocyclyl, optionally substituted heteroaryl, or optionally substituted aryl;

each instance of $R^A$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl;

each instance of $R^B$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl, or two $R^B$ are taken together with the intervening atoms to form a heterocycle.

In some embodiments of Formula I-a, $R^{6a}$ and $R^{6b}$ are each hydrogen. In certain embodiments, the present disclosure employs a compound of Formula (II):

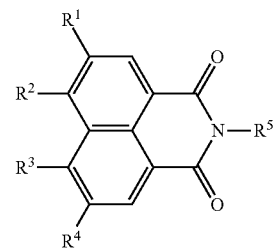

(II)

or a pharmaceutically acceptable salt, solvate, or hydrate thereof, wherein $R^1$, $R^2$, $R^3$, $R^4$ and $R^5$ are as described herein.

As described generally above, $R^1$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^1$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^1$ is selected from the group consisting of —H, —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heteroaryl, heterocyclyl, —$SO_2$-alkyl, and —$SO_2$-aryl. In certain embodiments, $R^1$ is selected from the group consisting of —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, heteroaryl, —$SO_2$-alkyl, and —$SO_2$-aryl. In certain embodiments, $R^1$ is selected from the group consisting of —H, —OH, —Cl, —Br, —F, methyl, ethyl, methoxy, ethoxy, —C≡C-aryl, phenyl, naphthyl, —$NO_2$, —NH—$C_{1-6}$ alkyl, —$C(O)CH_3$, —$CO_2H$, —$CO_2Et$, —CONH-aryl, —CN, N-morpholinyl, —$SO_2$-alkyl, and —$SO_2$-aryl. In certain embodiments, $R^1$ is hydrogen. In some embodiments, $R^1$ is $C_{1-6}$ alkyl. In certain embodiments, $R^1$ is —$C(O)OR^A$. In certain embodiments, $R^1$ is —$CO_2H$. In certain embodiments, $R^1$ is —$C(O)N(R^B)_2$, —$N(R^A)C(O)R^A$, or —$N(R^A)C(O)OR^A$. In some embodiments, $R^1$ is halogen. In certain embodiments, $R^1$ is fluoro. In certain embodiments, $R^1$ is chloro. In certain embodiments, $R^1$ is bromo. In certain embodiments, $R^1$ is iodo. In some embodiments, $R^1$ is —$N(R^B)_2$. In some embodiments, $R^1$ is —$NH_2$. In some embodiments, $R^1$ is —NH—$C_{1-6}$ alkyl. In certain embodiments, $R^1$ is —$NHCH_3$. In certain embodiments, $R^1$ is —$NO_2$. In some embodiments, $R^1$ is optionally substituted naphthyl.

As described generally above, $R^2$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^2$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^2$ is selected from the group consisting of —H, —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^2$ is selected from the group consisting of —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^2$ is selected from the group consisting of —H, —OH, —Cl, —Br, —F, methyl, ethyl, methoxy, ethoxy, —C≡C-aryl, phenyl, naphthyl, —$NO_2$, —NH-$C_{1-6}$ alkyl, —$C(O)CH_3$, —$CO_2H$, —$CO_2Et$, —CONH-aryl, —CN, N-morpholinyl, —$SO_2$-alkyl, and —$SO_2$-aryl. In certain embodiments, $R^2$ is hydrogen. In some embodiments, $R^2$ is $C_{1-6}$ alkyl. In certain embodiments, $R^2$ is —$C(O)OR^A$. In certain embodiments, $R^2$ is —$CO_2H$. In certain embodiments, $R^2$ is —$C(O)N(R^B)_2$, —$N(R^A)C(O)R^A$, or —$N(R^A)C(O)OR^A$. In some embodiments, $R^2$ is halogen. In certain embodiments, $R^2$ is fluoro. In certain embodiments, $R^2$ is chloro. In certain embodiments, $R^2$ is bromo. In certain embodiments, $R^2$ is iodo. In some embodiments, $R^2$ is —$NH_2$. In some embodiments, $R^2$ is —$N(R^B)_2$. In some embodiments, $R^2$ is —NH-$C_{1-6}$ alkyl. In certain embodiments, $R^2$ is —$NHCH_3$. In certain embodiments, $R^2$ is —$NO_2$. In some embodiments, $R^2$ is optionally substituted naphthyl.

As described generally above, $R^3$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^3$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^3$ is selected from the group consisting of —H, —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^3$ is selected from the group consisting of —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^3$ is selected from the group consisting of —H, —OH, —Cl, —Br, —F, methyl, ethyl, methoxy, ethoxy, —C≡C-aryl, phenyl, naphthyl, —$NO_2$, —NH-$C_{1-6}$ alkyl, —$C(O)CH_3$, —$CO_2H$, —$CO_2Et$, —CONH-aryl, —CN, N-morpholinyl, —$SO_2$-alkyl, and —$SO_2$-aryl. In certain embodiments, $R^3$ is hydrogen. In some embodiments, $R^3$ is $C_{1-6}$ alkyl. In certain embodiments, $R^3$ is —$C(O)OR^A$. In certain embodiments, $R^3$ is —$CO_2H$. In certain embodiments, $R^3$ is —$C(O)N(R^B)_2$, —$N(R^A)C(O)R^A$, or —$N(R^A)C(O)OR^A$. In some embodiments, $R^3$ is halogen. In certain embodiments, $R^3$ is fluoro. In certain embodiments, $R^3$ is chloro. In certain embodiments, $R^3$ is bromo. In certain embodiments, $R^3$ is iodo. In some embodiments, $R^3$ is —$N(R^B)_2$. In some embodiments, $R^3$ is —$NH_2$. In some embodiments, $R^3$ is —NH-$C_{1-6}$ alkyl. In certain embodiments, $R^3$ is —$NHCH_3$. In certain embodiments, $R^3$ is —$NO_2$. In some embodiments, $R^3$ is optionally substituted naphthyl.

As described generally above, $R^4$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^4$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^4$ is selected from the group consistinf of —H, —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^4$ is selected from the group consistinf of —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^4$ is selected from the group consisting of —H, —OH, —Cl, —Br, —F, methyl, ethyl, methoxy, ethoxy, —C≡C-aryl, phenyl, naphthyl, —$NO_2$, —NH-$C_{1-6}$ alkyl, —$C(O)CH_3$, —$CO_2H$, —$CO_2Et$, —CONH-aryl, —CN, N-morpholinyl, —$SO_2$-alkyl, and —$SO_2$-aryl. In certain embodiments, $R^4$ is hydrogen. In some embodiments, $R^4$ is $C_{1-6}$ alkyl. In certain embodiments, $R^4$ is —$C(O)OR^A$. In certain embodiments, $R^4$ is —$CO_2H$. In certain embodiments, $R^4$ is —$C(O)N(R^B)_2$, —$N(R^A)C(O)R^A$, or —$N(R^A)C(O)OR^A$. In some embodiments, $R^4$ is halogen. In certain embodiments, $R^4$ is fluoro. In certain embodiments, $R^4$ is chloro. In certain embodiments, $R^4$ is bromo. In certain embodiments, $R^4$ is iodo. In some embodiments, $R^4$ is —$N(R^B)_2$. In some embodiments, $R^4$ is —NH-$C_{1-6}$ alkyl. In certain embodiments, $R^4$ is —$NHCH_3$. In certain embodiments, $R^4$ is —$NO_2$. In some embodiments, $R^4$ is optionally substituted naphthyl.

As described generally above, $R^5$ is hydrogen, optionally substituted alkyl, optionally substituted alkenyl, optionally substituted alkynyl, optionally substituted heterocyclyl, optionally substituted heteroaryl, or optionally substituted aryl. In certain embodiments, $R^5$ is hydrogen. In some embodiments, $R^5$ is optionally substituted alkyl, optionally substituted alkenyl, optionally substituted alkynyl, optionally substituted heterocyclyl or optionally substituted aryl. In certain embodiments, $R^5$ is optionally substituted $C_{1-6}$ alkyl. In certain embodiments, $R^5$ is substituted $C_{1-6}$ alkyl. In certain embodiments, $R^5$ is unsubstituted $C_{1-6}$ alkyl. In certain embodiments, $R^5$ is methyl, ethyl, propyl, butyl, pentyl, or hexyl. In certain embodiments, $R^5$ is isopropyl, isobutyl, or isoamyl. In certain embodiments, $R^5$ is isobutyl.

In certain embodiments, $R^5$ is tent-butyl. In certain embodiments, $R^5$ is —$(CH_2)_n$—$N(R^B)_2$, wherein n is 1, 2, 3, 4, 5, or 6. In certain embodiments, n is 1. In certain embodiments, n is 2. In certain embodiments, n is 3. In certain embodiments, n is 4. In certain embodiments, n is 5. In certain embodiments, n is 6. In certain embodiments, $R^5$ is —$(CH_2)_n$—$NHR^B$. In certain embodiments, $R^5$ is —$(CH_2)_n$—$NHR^B$, wherein $R^B$ is optionally substituted $C_{1-6}$ alkyl. In certain embodiments, $R^5$ is —$(CH_2)_n$—$NHR^B$, wherein $R^B$ is unsubstituted $C_{1-6}$ alkyl. In certain embodiment, $R^5$ is —$(CH_2)_n$—$NHR^B$, wherein $R^B$ is substituted $C_{1-6}$ alkyl. In certain embodiments, $R^5$ is —$(CH_2)_n$—$N(CH_3)R^B$, wherein each $R^B$ is independently optionally substituted $C_{1-6}$ alkyl. In certain embodiments, $R^5$ is —$(CH_2)_n$—$N(CH_3)R^B$, wherein each $R^B$ is independently unsubstituted $C_{1-6}$ alkyl. In certain embodiments, $R^5$ is —$(CH_2)_n$—$N(CH_3)_2$. In certain embodiments, $R^5$ is —$(CH_2)_n$—$N(CH_2CH_3)R^B$, wherein each $R^B$ is independently optionally substituted $C_{1-6}$ alkyl. In certain embodiments, $R^5$ is —$(CH_2)_n$—$N(CH_2CH_3)R^B$, wherein each $R^B$ is independently unsubstituted $C_{1-6}$ alkyl. In certain embodiments, $R^5$ is —$(CH_2)_n$—$N(R^B)_2$, wherein each $R^B$ is independently selected from the group consisting of methyl, ethyl, isopropyl, isobutyl, isoamyl, and benzyl. In some embodiments, $R^5$ is —$(CH_2)_n$—$N(R^B)_2$, wherein each $R^B$ is the same. In certain embodiments, $R^5$ is —$(CH_2)_n$—$N(R^B)_2$, wherein n is 1, 2, 3, 4, 5, or 6, and wherein $R^B$ is independently optionally substituted $C_{1-6}$ alkyl or two $R^B$ are taken together with the intervening atoms to form a heterocycle with at least 1-4 heteroatoms. In certain embodiments, the heterocycle is a 3-8 membered ring. In certain embodiments, the heterocycle formed is In certain embodiments, $R^5$ is —$(CH_2)_n$—$N(R^B)_2$, wherein n is 1, 2, 3, 4, or 5, and wherein $R^B$ is independently optionally substituted $C_{1-6}$ alkyl or two $R^B$ are taken together with the intervening atoms to form a heterocycle. In some embodiments, $R^5$ is —$(CH_2)_n$—$N(R^B)_2$, wherein each $R^B$ is different. In certain embodiments, $R^5$ is —$(CH_2)_n$—$NH_2$. In certain embodiments, $R^5$ is —$(CH_2)_s$—$CO_2R^A$, wherein s is 1, 2, 3, 4, 5, or 6. In certain embodiments, $R^5$ is —$(CH_2)_s$—$CO_2H$. In some embodiments, s is 1. In some embodiments, s is 2. In some embodiments, s is 3. In some embodiments, s is 4. In some embodiments, s is 5. In some embodiments, s is 6. In certain embodiments, $R^5$ is —$CH_2$—$CO_2R^A$, wherein $R^A$ is hydrogen or optionally substituted alkyl. In certain embodiments, $R^5$ is —$C(O)O$-methyl. In certain embodiments, $R^5$ is —$C(O)O$-ethyl. In certain embodiments, $R^5$ is —$C(O)O$-propyl, —$OC(O)$-isopropyl, —$C(O)O$-isobutyl, or —$OC(O)$-isoamyl. In certain embodiments, $R^5$ is —$(CH_2)_2$—$CO_2R^A$, wherein $R^A$ is hydrogen or optionally substituted alkyl. In certain embodiments, $R^5$ is —$(CH_2)_3$—$CO_2R^A$, wherein $R^A$ is hydrogen or optionally substituted alkyl. In certain embodiments, $R^5$ is —$(CH_2)_4$—$CO_2R^A$, wherein $R^A$ is hydrogen or optionally substituted alkyl. In certain embodiments, $R^5$ is —$(CH_2)_5$—$CO_2R^A$, wherein $R^A$ is hydrogen or optionally substituted alkyl. In certain embodiments, $R^5$ is —$(CH_2)_6$—$CO_2R^A$, wherein $R^A$ is hydrogen or optionally substituted alkyl. In certain embodiments, $R^5$ is —$(CH_2)_s$—$CO_2NR^A_3$, wherein $R^A$ is hydrogen or optionally substituted alkyl, and s is 1 to 5.

In certain embodiments, $R^5$ is optionally substituted aryl. In some embodiments, $R^5$ is of the following structure:

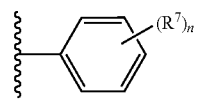

wherein:

each instance of $R^7$ is independently selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$C(O)N(R^B)_2$, —$CN$, —$NO_2$, —$C(O)R^A$, —$C(O)OR^A$, —$S(O)R^A$, —$SO_2R^A$, —$SO_2N(R^B)_2$, and —$NHSO_2R^B$;

each instance of $R^A$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl;

each instance of $R^B$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl, or two $R^B$ are taken together with the intervening atoms to form a heterocycle; and n is 0, 1, 2, 3, 4 or 5.

As generally defined herein, n is 0, 1, 2, 3, 4, or 5. In certain embodiments, n is 0 and $R^5$ is phenyl. In certain embodiments, n is 1 and $R^5$ is of the formula

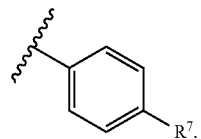

In certain embodiments, n is 1 and $R^5$ is of the formula

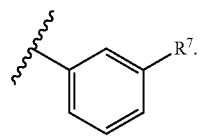

In certain embodiments, n is 1 and $R^5$ is of the formula

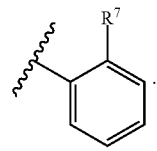

In certain embodiments, n is 2 and $R^5$ is of the formula

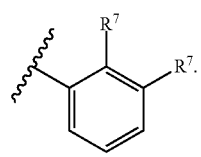

In certain embodiments, n is 2 and $R^5$ is of the formula

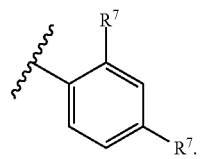

In certain embodiments, n is 2 and $R^5$ is of the formula

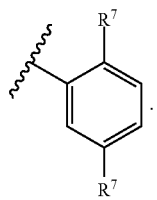

In certain embodiments, n is 2 and $R^5$ is of the formula

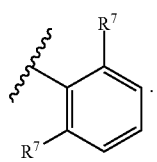

In certain embodiments, In certain embodiments, n is 2 and $R^5$ is of the formula

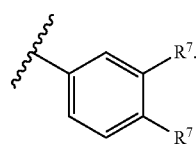

In certain embodiments, In certain embodiments, n is 2 and $R^5$ is of the formula

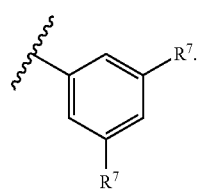

In certain embodiments, n is 3 and $R^5$ is of the formula

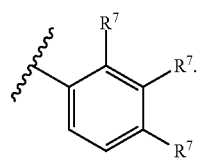

In certain embodiments, n is 3 and $R^5$ is of the formula

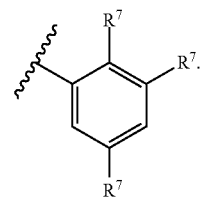

In certain embodiments, n is 3 and $R^5$ is of the formula

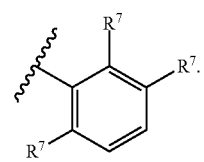

In certain embodiments, n is 3 and $R^5$ is of the formula

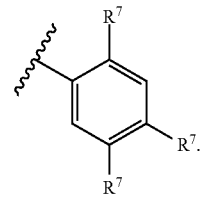

In certain embodiments, n is 3 and $R^5$ is of the formula

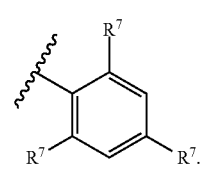

In certain embodiments, n is 4 and $R^5$ is of the formula

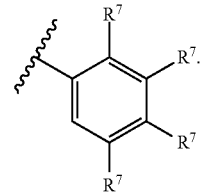

In certain embodiments, n is 4 and $R^5$ is of the formula

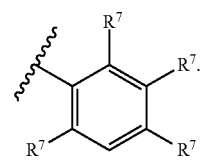

In certain embodiments, n is 4 and $R^5$ is of the formula

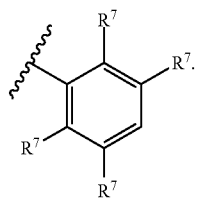

In certain embodiments, n is 5 and $R^5$ is of the formula

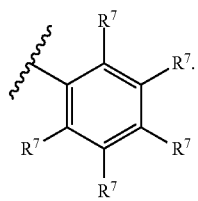

In certain embodiments, $R^7$ is hydrogen. In some embodiments, $R^7$ is halo. In certain embodiments, $R^7$ is fluoro. In certain embodiments, $R^7$ is chloro. In certain embodiments, $R^7$ is bromo. In certain embodiments, $R^7$ is iodo. In some embodiments, $R^7$ is optionally substituted alkyl, optionally substituted alkenyl, optionally substituted alkynyl, optionally substituted heterocyclyl or optionally substituted aryl. In certain embodiments, $R^7$ is optionally substituted $C_{1-6}$ alkyl. In certain embodiments, $R^7$ is substituted $C_{1-6}$ alkyl. In certain embodiments, $R^7$ is substituted methyl, ethyl, propyl, butyl, pentyl, or hexyl. In certain embodiments, $R^7$ is $CH_2F$. In certain embodiments, $R^7$ is $CHF_2$. In certain embodiments, $R^7$ is $CF_3$. In certain embodiments, $R^7$ is —$(CH_2)_s$—$CO_2R^A$, wherein s is 1, 2, 3, 4, 5, or 6. In certain embodiments, $R^7$ is —$(CH_2)_s$—$CO_2H$. In some embodiments, s is 1. In some embodiments, s is 2. In some embodiments, s is 3. In some embodiments, s is 4. In some embodiments, s is 5. In some embodiments, s is 6. In certain embodiments, $R^7$ is —$CH_2$—$CO_2R^A$, wherein $R^A$ is hydrogen or optionally substituted alkyl. In certain embodiments, $R^7$ is —C(O)O-methyl. In certain embodiments, $R^7$ is —C(O)O-ethyl. In certain embodiments, $R^7$ is —C(O)O-propyl, —OC(O)-isopropyl, —C(O)O-isobutyl, or —OC(O)-isoamyl. In certain embodiments, $R^7$ is —$(CH_2)_2$—$CO_2R^A$, wherein $R^A$ is hydrogen or optionally substituted alkyl. In certain embodiments, $R^7$ is —$(CH_2)_3$—$CO_2R^A$, wherein $R^A$ is hydrogen or optionally substituted alkyl. In certain embodiments, $R^7$ is —$(CH_2)_4$—$CO_2R^A$, wherein $R^A$ is hydrogen or optionally substituted alkyl. In certain embodiments, $R^7$ is —$(CH_2)_5$—$CO_2R^A$, wherein $R^A$ is hydrogen or optionally substituted alkyl. In certain embodiments, $R^7$ is —$(CH_2)_6$—$CO_2R^A$, wherein $R^A$ is hydrogen or optionally substituted alkyl.

In certain embodiments, $R^7$ is unsubstituted $C_{1-6}$ alkyl. In certain embodiments, $R^7$ is methyl, ethyl, propyl, butyl, pentyl, or hexyl. In certain embodiments, $R^7$ is isopropyl, isobutyl, or isoamyl. In certain embodiments, $R^7$ is isobutyl. In certain embodiments, $R^7$ is tert-butyl.

In certain embodiments, $R^7$ is —$OR^A$. In certain embodiments, $R^7$ is —OH. In certain embodiments, $R^7$ is —$OR^A$, wherein $R^A$ is optionally substituted alkyl. In certain embodiments, $R^7$ is —O-methyl. In certain embodiments, $R^7$ is —O-ethyl. In certain embodiments, $R^7$ is —O-propyl, —O-isopropyl, —O-isobutyl, or —O-isoamyl.

In certain embodiments, $R^7$ is —$N(R^B)_2$, wherein each $R^B$ is independently selected from the group consisting of methyl, ethyl, isopropyl, isobutyl, isoamyl, and benzyl. In some embodiments, $R^7$ is —$N(R^B)_2$, wherein each $R^B$ is the same. In some embodiments, $R^7$ is —$N(R^B)_2$, wherein each $R^B$ is different. In certain embodiments, $R^7$ is —$NH_2$.

In certain embodiments, $R^7$ is —$CO_2R^A$. In certain embodiments, $R^7$ is —$CO_2H$. In certain embodiments, $R^7$ is —$CO_2R^A$, wherein $R^A$ is optionally substituted alkyl. In certain embodiments, $R^7$ is —C(O)O-methyl. In certain embodiments, $R^7$ is —C(O)O-ethyl. In certain embodiments, $R^7$ is —C(O)O-propyl, —OC(O)-isopropyl, —C(O)O-isobutyl, or —OC(O)-isoamyl.

In some embodiments, at least two of $R^1$, $R^2$, $R^3$, and $R^4$ are hydrogen. In certain embodiments, $R^1$ and $R^4$ are hydrogen. In certain embodiments, $R^3$ and $R^4$ are hydrogen. In certain embodiments, $R^1$ and $R^2$ are hydrogen. In certain embodiments, $R^1$ and $R^3$ are hydrogen. In certain embodiments, $R^2$ and $R^4$ are hydrogen. In some embodiments, at least two of $R^1$, $R^2$, $R^3$, and $R^4$ are each hydrogen, and $R^5$ is hydrogen. In some embodiments, $R^1$, $R^3$, and $R^4$ are hydrogen. In some embodiments, $R^1$, $R^2$, and $R^3$ are hydrogen. In some embodiments, $R^2$, $R^3$, and $R^4$ are hydrogen.

In some embodiments, the compound provided herein is of Formula (III) or (IV):

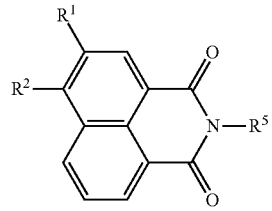

(III)

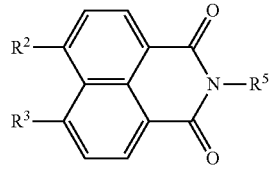

(IV)

or a pharmaceutically acceptable salt, solvate, or hydrate thereof, wherein $R^1$, $R^2$, $R^3$, and $R^5$ are as defined herein. In certain embodiments, $R^2$ and $R^3$ are taken together with their intervening atoms to form an optionally substituted carbocycle or heterocycle.

In certain embodiments, the compound provided herein is of Formula (III-a) or (III-b):

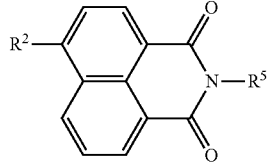

(III-a)

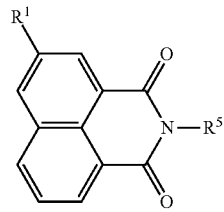

(III-b)

or a pharmaceutically acceptable salt, solvate, or hydrate thereof, wherein $R^1$, $R^2$, and $R^5$ are as defined herein. In certain embodiments, a compound of the present disclosure is selected from the group consisting of the compounds listed in Tables 1a and 1b.

Compounds of interest also include 2,3-dihydro-1H-benzo[de]isoquinoline analogues, e.g., compounds that include a 2,3-dihydro-1H-benzo[de]isoquinoline scaffold substituted with one or more substituents which are non-hydrgoen. The 2,3-dihydro-1H-benzo[de]isoquinoline scaffold of Formula (V) may be substituted at any position 1, 2, 3, 4, 5, 6, 7, 8 and/or 9:

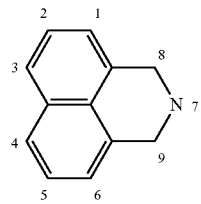

(V)

In certain embodiments, positions 3, 7, 8, and/or 9 of the Formula (V) scaffold are substituted as described herein. In certain embodiments, only positions 3 and 7 of the Formula (V) scaffold are substituted as described herein. In certain embodiments, positions 7, 8, and/or 9 of the Formula (V) scaffold are substituted as described herein. In certain embodiments, positions 7 and 8 of the Formula (V) scaffold are substituted as described herein. In certain embodiments, positions 7 and 9 of the Formula (V) scaffold are substituted as described herein. In certain embodiments, positions 7 of the Formula (V) scaffold are substituted as described herein. In certain embodiments, positions 3, 4, 7, 8, and/or 9 of the Formula (V) scaffold are substituted as described herein. In certain embodiments, positions 4, 7, 8, and 9 of the Formula (V) scaffold are substituted as described herein. In certain embodiments, positions 4 and 7 of the Formula (V) scaffold are substituted as described herein. The remaining positions of the foregoing embodiments are substituted with hydrogen.

TABLE 1a

Exemplary Compounds of Formula I-a.

| ID | BO number | Structure | $IC_{50}$ (μM) | γ globin induction (at $IC_{50}$) | MF | MW | MP (° C.) | Reference MP (° C.) | Yield (%) |
|---|---|---|---|---|---|---|---|---|---|
| A1 | BO-2388 | 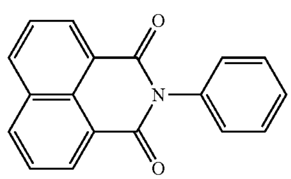 [SMILES: O=C1c2cccc3cccc(c23)C(=O)N1c1ccccc1] | >100 | ND | $C_{18}H_{11}NO_2$ | 273.3 | 218-220 | 202 (16) | 70.7 |
| A2 | BO-2375 | 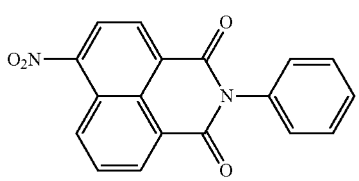 [SMILES: O=C1c2cccc3c([N+](=O)[O-])ccc(c23)C(=O)N1c1ccccc1] | 0.3 | 1.1 | $C_{18}H_{10}N_2O_4$ | 318.3 | >280 | 280-282 (17) | 92.7 |
| A3 | BO-2376 | 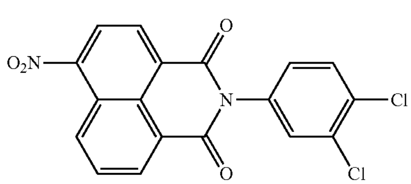 [SMILES: O=C1c2cccc3c([N+](=O)[O-])ccc(c23)C(=O)N1c1ccc(Cl)c(Cl)c1] | 5.2 | ND | $C_{18}H_8Cl_2N_2O_4$ | 387.2 | >280 | | 85.2 |
| A4 | BO-2377 | 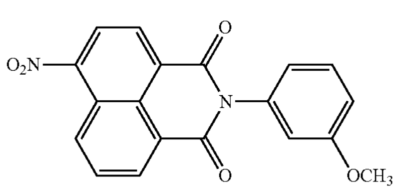 [SMILES: COc1cccc(N2C(=O)c3cccc4c([N+](=O)[O-])ccc(c34)C2=O)c1] | 21 | ND | $C_{19}H_{12}N_2O_5$ | 348.3 | >280 | | 92.2 |

TABLE 1a-continued

Exemplary Compounds of Formula I-a.

| ID | BO number | Structure | IC$_{50}$ (μM) | γ globin induction (at IC$_{50}$) | MF | MW | MP (° C.) | Reference MP (° C.) | Yield (%) |
|---|---|---|---|---|---|---|---|---|---|
| A5 | BO-2378 | 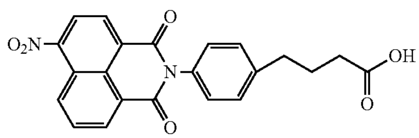 [SMILES: O=C(O)CCCc1ccc(N2C(=O)c3cccc4c([N+](=O)[O-])ccc(c34)C2=O)cc1] | 6.7 | ND | C$_{22}$H$_{12}$N$_2$O$_6$ | 404.4 | 254.5-256 | | 38 |
| A6 | BO-2379 | 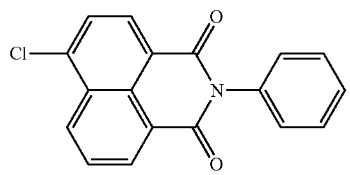 [SMILES: O=C1c2cccc3c(Cl)ccc(c23)C(=O)N1c1ccccc1] | >100 | ND | C$_{18}$H$_{10}$ClNO$_3$ | 307.7 | 263-265.5 | 231-233 (18) | 22.4 |
| A7 | BO-2380 | 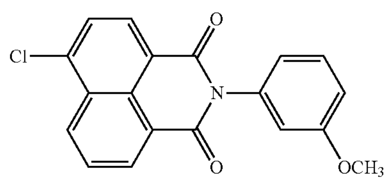 [SMILES: COc1cccc(N2C(=O)c3cccc4c(Cl)ccc(c34)C2=O)c1] | >100 | ND | C$_{19}$H$_{12}$ClNO$_2$ | 337.8 | >280 | | 37 |
| A8 | BO-2381 | 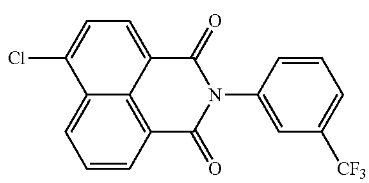 [SMILES: O=C1c2cccc3c(Cl)ccc(c23)C(=O)N1c1cccc(C(F)(F)F)c1] | >100 | ND | C$_{19}$H$_9$ClF$_3$NO$_2$ | 375.7 | 278-279 | | 17.3 |
| A9 | BO-2382 | 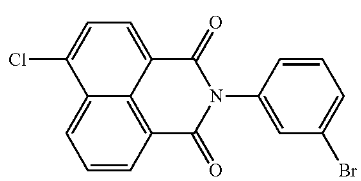 [SMILES: O=C1c2cccc3c(Cl)ccc(c23)C(=O)N1c1cccc(Br)c1] | >100 | ND | C$_{18}$H$_9$BrClNO$_2$ | 386.6 | >280 | | 13.2 |
| A10 | BO-2383 | 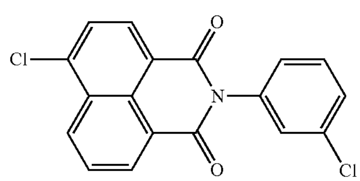 [SMILES: O=C1c2cccc3c(Cl)ccc(c23)C(=O)N1c1cccc(Cl)c1] | >100 | ND | C$_{18}$H$_9$Cl$_2$NO$_2$ | 342.2 | 273-275 | | 12.1 |
| A11 | BO-2384 | 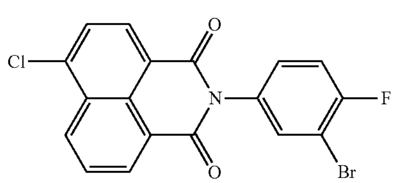 [SMILES: O=C1c2cccc3c(Cl)ccc(c23)C(=O)N1c1ccc(F)c(Br)c1] | >100 | ND | C$_{18}$H$_8$BrClFNO$_2$ | 404.6 | >280 | | 49.2 |
| A12 | BO-2384 | 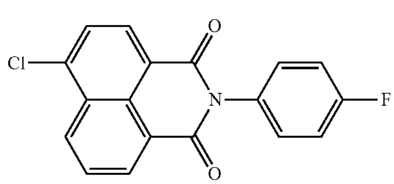 [SMILES: O=C1c2cccc3c(Cl)ccc(c23)C(=O)N1c1ccc(F)cc1] | >100 | ND | C$_{18}$H$_9$ClFNO$_2$ | 325.7 | 274-276 | | 40.5 |

TABLE 1a-continued

Exemplary Compounds of Formula I-a.

| ID | BO number | Structure | IC$_{50}$ (μM) | γ globin induction (at IC$_{50}$) | MF | MW | MP (° C.) | Reference MP (° C.) | Yield (%) |
|---|---|---|---|---|---|---|---|---|---|
| A13 | BO-2386 | 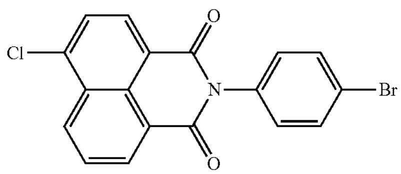 [SMILES: O=C1c2cccc3c(Cl)ccc(c23)C(=O)N1c1ccc(Br)cc1] | >100 | ND | C$_{18}$H$_9$BrClNO$_2$ | 386.6 | >280 | | 66.3 |
| A14 | BO-2387 | 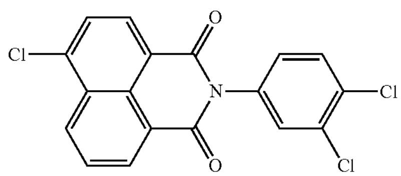 [SMILES: O=C1c2cccc3c(Cl)ccc(c23)C(=O)N1c1ccc(Cl)c(Cl)c1] | >100 | ND | C$_{18}$H$_8$Cl$_3$NO$_2$ | 376.6 | >280 | >300 (18) | 15.9 |
| B1 | BO-2393 | 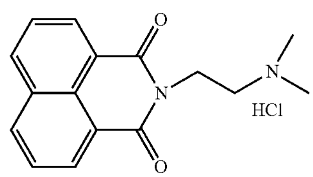 [SMILES: CN(C)CCN1C(=O)c2cccc3cccc(c23)C1=O ; Cl] | 10.7 | 4.1 | C$_{16}$H$_{17}$ClN$_2$O$_2$ | 304.8 | >280 | 296-298 (20) | 84.5 |
| B2 | BO-2390 | 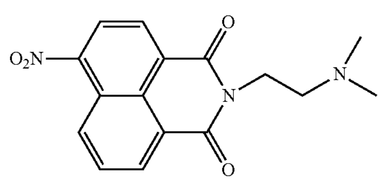 [SMILES: CN(C)CCN1C(=O)c2cccc3c([N+](=O)[O-])ccc(c23)C1=O] | 2.6 | ND | C$_{16}$H$_{15}$N$_3$O$_4$ | 313.3 | 131-133 | 106-109 (20) | 65.7 |
| B3 | BO-2391 | 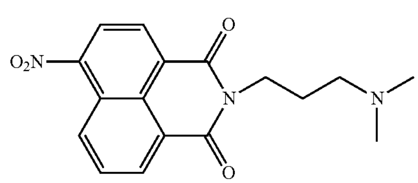 [SMILES: CN(C)CCCN1C(=O)c2cccc3c([N+](=O)[O-])ccc(c23)C1=O] | 2.3 | ND | C$_{17}$H$_{17}$N$_3$O$_4$ | 327.3 | 108-110 | 106-109 (21) | 42 |
| B4 | BO-2392 | 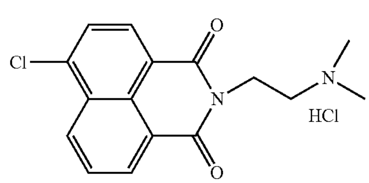 [SMILES: CN(C)CCN1C(=O)c2cccc3c(Cl)ccc(c23)C1=O ; Cl] | 5 | 3.3 | C$_{16}$H$_{16}$Cl$_2$N$_2$O$_2$ | 339.2 | >280 | 293-295 (22) | 81.5 |
| C1 | BO-2400 | 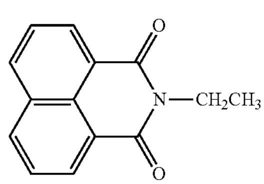 [SMILES: CCN1C(=O)c2cccc3cccc(c23)C1=O] | >100 | ND | C$_{14}$H$_{11}$NO$_2$ | 225.2 | 171-172.5 | 158 (18) | 37.3 |
| C2 | BO-2396 | 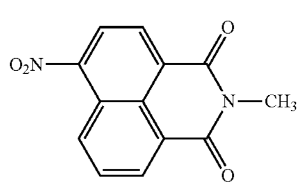 [SMILES: CN1C(=O)c2cccc3c([N+](=O)[O-])ccc(c23)C1=O] | >100 | ND | C$_{13}$H$_8$N$_2$O$_4$ | 256.2 | 209-212.5 | 208-209 (18) | 51.1 |

TABLE 1a-continued

Exemplary Compounds of Formula I-a.

| ID | BO number | Structure | IC$_{50}$ (μM) | γ globin induction (at IC$_{50}$) | MF | MW | MP (° C.) | Reference MP (° C.) | Yield (%) |
|---|---|---|---|---|---|---|---|---|---|
| C3 | BO-2397 | 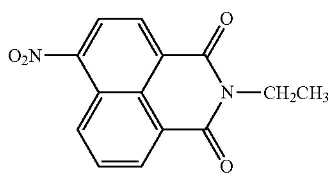 [SMILES: CCN1C(=O)c2cccc3c([N+](=O)[O-])ccc(c23)C1=O] | >100 | ND | C$_{14}$H$_{10}$N$_2$O$_4$ | 270.2 | 191-192.5 | 187.5-188.5 (18) | 34.1 |
| C4 | BO-2398 | 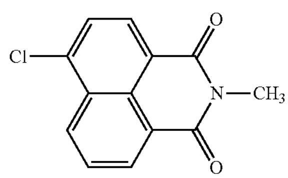 [SMILES: CN1C(=O)c2cccc3c(Cl)ccc(c23)C1=O] | >100 | ND | C$_{13}$H$_8$ClNO$_2$ | 245.7 | 186-188 | 171-173 (18) | 32.6 |
| C5 | BO-2399 | 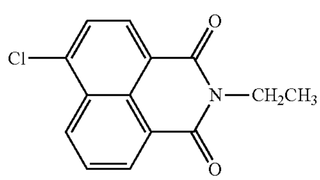 [SMILES: CCN1C(=O)c2cccc3c(Cl)ccc(c23)C1=O] | >100 | ND | C$_{14}$H$_{10}$ClNO$_2$ | 259.7 | 167-170 | 165-166 (18) | 33.7 |
| D1 | BO-2401 | 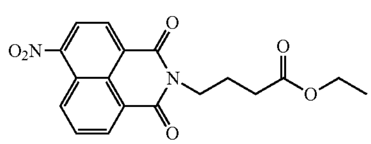 [SMILES: CCOC(=O)CCCN1C(=O)c2cccc3c([N+](=O)[O-])ccc(c23)C1=O] | 6.3 | ND | C$_{18}$H$_{16}$N$_2$O$_6$ | 356.3 | 115-116 | | 97 |
| E1 | BO-2389 | 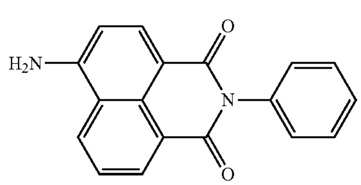 | 2.2 | 1.3 | C$_{18}$H$_{12}$N$_2$O$_2$ | 288.3 | 276-278 | 302-304 (23) | 56.4 |
| E2 (SS-2394) | BO-2394 | 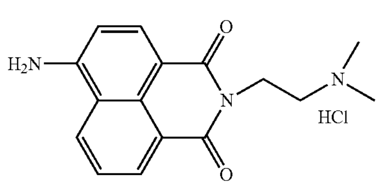 [SMILES: CN(C)CCN1C(=O)c2cccc3c(N)ccc(c23)C1=O ; Cl] | 2.3 | 4 | C$_{16}$H$_{18}$ClN$_3$O$_2$ | 319.8 | >280 | 184-185 (20) | 77.3 |
| E3 | BO-2395 | 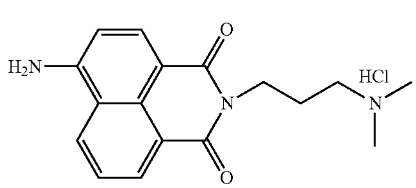 | 11.2 | 2.7 | C$_{17}$H$_{20}$ClN$_3$O$_2$ | 333.8 | >280 | 184-185 (21) | 42.8 |

TABLE 1b

Additional Exemplary Compounds of Formula I-a.

| BO number | Structure |
|---|---|
| BO-2562 | ![structure] |
| BO-2559 | ![structure] |
| BO-2561 | ![structure] |

In certain embodiments, a substituent may contribute to optical isomerism and/or stereo isomerism of a compound. The compound(s) of the present disclosure provided herein include the neutral form, salts, solvates, hydrates, and prodrug forms of a compound. All such forms are embraced by the present disclosure. Thus the compounds described herein include salts, solvates, hydrates, prodrug, and isomer forms thereof, including the pharmaceutically acceptable salts, solvates, hydrates, prodrugs, and isomers thereof. In certain embodiments, a compound may be a metabolized into a pharmaceutically active derivative.

In certain embodiments, the present disclosure employs a compound of Formula (V-a):

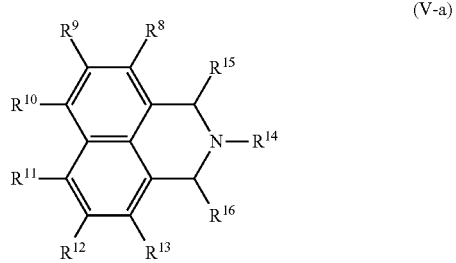

(V-a)

or a pharmaceutically acceptable salt, solvate, or hydrate thereof, wherein:

$R^8$, $R^9$, $R^{10}$, $R^{11}$, $R^{12}$ and $R^{13}$ are each independently selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$;

$R^{14}$ is hydrogen, optionally substituted alkyl, optionally substituted alkenyl, optionally substituted alkynyl, optionally substituted heterocyclyl, optionally substituted heteroaryl, or optionally substituted aryl;

$R^{15}$ and $R^{16}$ are each independently selected from the group consisting of hydrogen, oxygen, hydroxyl, —OR, and —OC(O)R, wherein both $R^{15}$ and $R^{16}$ are not oxygen connected via a double bond, wherein R is optionally substituted alkyl, optionally substituted alkenyl, optionally substituted alkynyl, optionally substituted heterocyclyl, optionally substituted heteroaryl, and optionally substituted aryl;

each instance of $R^A$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl; and each instance of $R^B$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl, or two $R^B$ are taken together with the intervening atoms to form a heterocycle.

In some embodiments, $R^{10}$ is —$N(R^B)_2$, —$N(R^A)C(O)R^A$, or —$N(R^A)C(O)OR^A$. In some embodiments, $R^A$ is independently hydrogen or optionally substituted alkyl. In some embodiments, $R^A$ is independently hydrogen, methyl or ethyl. In some embodiments, $R^B$ is independently hydrogen or optionally substituted alkyl. In some embodiments, $R^B$ is independently hydrogen, methyl or ethyl. In some embodiments, each $R^B$ is hydrogen. In some embodiments, each $R^B$ is methyl. In some embodiments, $R^{10}$ is hydrogen, —$NH_2$, —$NHC(O)CH_3$, —$NHC(O)OR^A$, —$NHR^B$, —$NR^B_2$, wherein $R^B$ can be $C_1$-$C_5$ alkyl. In some embodiments, $R^{10}$ is hydrogen, —$NHC(O)CH_3$, —$NHC(O)O(CH_3)$, —$N(CH_3)_2$, —$NH_2$, or —$NHCH_2CH_3$. In some embodiments, $R^{10}$ is hydrogen and $R^8$, $R^9$, $R^{11}$, $R^{12}$, and $R^{13}$ are each independently H or the groups recited for $R^{10}$.

In some embodiments, $R^{11}$ is —$N(R^B)_2$, —$N(R^A)C(O)R^A$, or —$N(R^A)C(O)OR^A$. In some embodiments, $R^A$ is independently hydrogen or optionally substituted alkyl. In some embodiments, $R^A$ is independently hydrogen, methyl or ethyl. In some embodiments, $R^B$ is independently hydrogen or optionally substituted alkyl. In some embodiments, $R^B$ is independently hydrogen, methyl or ethyl. In some embodiments, each $R^B$ is hydrogen. In some embodiments, each $R^B$ is methyl. In some embodiments, $R^{11}$ is hydrogen, —$NH_2$, —$NHC(O)CH_3$, —$N(R^A)C(O)OR^B$, —$NHR^B$, —$NR^B_2$, wherein $R^B$ can be $C_1$-$C_5$ alkyl. In some embodiments, $R^{11}$ is hydrogen, —$NHC(O)CH_3$, —$NHC(O)O(CH_3)$, —$N(CH_3)_2$, —$NH_2$, or —$NHCH_2CH_3$. In some embodiments, $R^{11}$ is hydrogen and $R^8$, $R^9$, $R^{11}$, $R^{12}$, and $R^{13}$ are each independently H or the groups recited for $R^{11}$.

In certain embodiments, $R^{14}$ is hydrogen. In some embodiments, $R^{14}$ is an optionally substituted alkyl. In certain embodiments, $R^{14}$ is an optionally substituted $C_{1-6}$ alkyl. In certain embodiments, $R^{14}$ is a substituted $C_{1-6}$ alkyl.

In certain embodiments, $R^{14}$ is a unsubstituted $C_{1-6}$ alkyl. In certain embodiments, $R^{14}$ is a substituted methyl, ethyl, propyl, butyl, pentyl, or hexyl. In certain embodiments, $R^{14}$ is —$(CH_2)_n$—$N(R^B)_2$, wherein n is 1, 2, 3, 4, 5, or 6, and wherein $R^B$ is independently optionally substituted $C_{1-6}$ alkyl or two $R^B$ are taken together with the intervening atoms to form a heterocycle with at least 1-4 heteroatoms. In certain embodiments, the heterocycle is a 3-8 membered ring. In certain embodiments, $R^{14}$ is —$(CH_2)_n$—$N(R^B)_2$, wherein n is 1, 2, 3, 4, or 5, and wherein $R^B$ is independently optionally substituted $C_{1-6}$ alkyl or two $R^B$ are taken together with the intervening atoms to form a heterocycle. In certain embodiments, n is 1. In certain embodiments, n is 2. In certain embodiments, n is 3. In certain embodiments, n is 4. In certain embodiments, n is 5. In certain embodiments, n is 6. In certain embodiments, $R^{14}$ is —$(CH_2)_n$—$N(R^B)_2$, wherein n is 2. In certain embodiments, $R^{14}$ is —$(CH_2)_n$—$NHR^B$, wherein $R^B$ is optionally substituted $C_{1-6}$ alkyl. In certain embodiments, $R^{14}$ is —$(CH_2)_n$—$NHR^B$, wherein $R^B$ is unsubstituted $C_{1-6}$ alkyl. In certain embodiment, $R^{14}$ is —$(CH_2)_n$—$NHR^B$, wherein $R^B$ is substituted $C_{1-6}$ alkyl. In certain embodiments, $R^{14}$ is —$(CH_2)_n$—$N(CH_3)R^B$, wherein each $R^B$ is independently optionally substituted $C_{1-6}$ alkyl. In certain embodiments, $R^{14}$ is —$(CH_2)_n$—$N(CH_3)R^B$, wherein each $R^B$ is independently unsubstituted $C_{1-6}$ alkyl. In certain embodiments, $R^{14}$ is —$(CH_2)_n$—$N(CH_3)_2$. In certain embodiments, $R^{14}$ is —$(CH_2)_n$—$N(CH_2CH_3)R^B$, wherein each $R^B$ is independently optionally substituted $C_{1-6}$ alkyl. In certain embodiments, $R^{14}$ is —$(CH_2)_n$—$N(CH_2CH_3)R^B$, wherein each $R^B$ is independently unsubstituted $C_{1-6}$ alkyl. In certain embodiments, $R^{14}$ is —$(CH_2)_n$—$N(R^B)_2$, wherein each $R^B$ is independently selected from the group consisting of methyl, ethyl, isopropyl, isobutyl, isoamyl, and benzyl. In some embodiments, $R^{14}$ is —$(CH_2)_n$—$N(R^B)_2$, wherein each $R^B$ is the same. In some embodiments, $R^{14}$ is —$(CH_2)_n$—$N(R^B)_2$, wherein each $R^B$ is different. In certain embodiments, $R^{14}$ is —$(CH_2)_n$—$NH_2$. In certain embodiments, $R^{14}$ is —$(CH_2)_2N(CH_3)_2$. In certain embodiments, $R^{14}$ comprises a carboxylic acid or tetraammonium moiety. In certain embodiments, $R^{14}$ is —$(CH_2)_n$—COOH or —$(CH_2)_n$—$COONR^C_3$ or, wherein n is 1, 2, 3, 4, 5, or 6 and $R^C$ is an optionally substituted $C_{1-6}$ alkyl, wherein the optional substituent is a hydroxyl. In certain embodiments, $R^C$ is —$(CH_2)_2OH$, —$(CH_2)_2OH$, —$(CH_2)_3OH$, —$(CH_2)_4OH$, —$(CH_2)_5OH$.

As described generally above, $R^8$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^8$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^8$ is selected from the group consisting of —H, —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^8$ is selected from the group consisting of —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^8$ is selected from the group consisting of —H, —OH, —Cl, —Br, —F, methyl, ethyl, methoxy, ethoxy, —C≡C-aryl, phenyl, naphthyl, —$NO_2$, —NH-$C_{1-6}$ alkyl, —$C(O)CH_3$, —$CO_2H$, —$CO_2Et$, —CONH-aryl, —CN, N-morpholinyl, —$SO_2$-alkyl, and —$SO_2$-aryl. In certain embodiments, $R^8$ is hydrogen. In some embodiments, $R^8$ is $C_{1-6}$ alkyl. In certain embodiments, $R^8$ is —$C(O)OR^A$. In certain embodiments, $R^8$ is —$CO_2H$. In certain embodiments, $R^8$ is —$C(O)N(R^B)_2$ or —$N(R^A)C(O)R^A$. In some embodiments, $R^8$ is halogen. In certain embodiments, $R^8$ is fluoro. In certain embodiments, $R^8$ is chloro. In certain embodiments, $R^8$ is bromo. In certain embodiments, $R^8$ is iodo. In some embodiments, $R^8$ is —$NH_2$. In some embodiments, $R^8$ is —$N(R^B)_2$. In some embodiments, $R^8$ is —NH-$C_{1-6}$ alkyl. In certain embodiments, $R^8$ is —$NHCH_3$. In certain embodiments, $R^8$ is —$NO_2$. In some embodiments, $R^8$ is optionally substituted naphthyl.

As described generally above, $R^9$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^9$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^9$ is selected from the group consisting of —H, —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^9$ is selected from the group consisting of —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^9$ is selected from the group consisting of —H, —OH, —Cl, —Br, —F, methyl, ethyl, methoxy, ethoxy, —C≡C-aryl, phenyl, naphthyl, —$NO_2$, —NH-$C_{1-6}$ alkyl, —$C(O)CH_3$, —$CO_2H$, —$CO_2Et$, —CONH-aryl, —CN, N-morpholinyl, —$SO_2$-alkyl, and —$SO_2$-aryl. In certain embodiments, $R^9$ is hydrogen. In some embodiments, $R^9$ is $C_{1-6}$ alkyl. In certain embodiments, $R^9$ is —$C(O)OR^A$. In certain embodiments, $R^9$ is —$CO_2H$. In certain embodiments, $R^9$ is —$C(O)N(R^B)_2$, —$N(R^A)C(O)R^A$, or —$N(R^A)C(O)OR^A$. In some embodiments, $R^9$ is halogen. In certain embodiments, $R^9$ is fluoro. In certain embodiments, $R^9$ is chloro. In certain embodiments, $R^9$ is bromo. In certain embodiments, $R^9$ is iodo. In some embodiments, $R^9$ is —$N(R^B)_2$. In some embodiments, $R^9$ is —$NH_2$. In some embodiments, $R^9$ is —NH-$C_{1-6}$ alkyl. In certain embodiments, $R^9$ is —$NHCH_3$.

In certain embodiments, $R^9$ is —$NO_2$. In some embodiments, $R^9$ is optionally substituted naphthyl.

As described generally above, $R^{10}$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^{10}$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^{10}$ is selected from the group consisting of —H, —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^{10}$ is selected from the group consisting of —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^{10}$ is selected from the group consisting of —OH, —Cl, —Br, —F, methyl, ethyl, methoxy, ethoxy, —C≡C-aryl, phenyl, naphthyl, —$NO_2$, —NH-$C_{1-6}$ alkyl, —$C(O)CH_3$, —$CO_2H$, —$CO_2Et$, —CONH-aryl, —CN, N-morpholinyl, —$SO_2$-alkyl, and —$SO_2$-aryl. In certain embodiments, $R^{10}$ is hydrogen. In some embodiments, $R^{10}$ is $C_{1-6}$ alkyl. In certain embodiments, $R^{10}$ is —$C(O)OR^A$. In certain embodiments, $R^{10}$ is —$CO_2H$. In certain embodiments, $R^{10}$ is —$C(O)N(R^B)_2$, —$N(R^A)C(O)R^A$, or —$N(R^A)C(O)OR^A$—. In some embodiments, $R^{10}$ is halogen. In certain embodiments, $R^{10}$ is fluoro. In certain embodiments, $R^{10}$ is chloro. In certain embodiments, $R^{10}$ is bromo. In certain embodiments, $R^{10}$ is iodo. In some embodiments, $R^{10}$ is —$N(R^B)_2$. In some embodiments, $R^{10}$ is —$NH_2$. In some embodiments, $R^{10}$ is —NH-$C_{1-6}$ alkyl. In certain embodiments, $R^{10}$ is —$NHCH_3$. In certain embodiments, $R^{10}$ is —$NO_2$. In some embodiments, $R^{10}$ is optionally substituted naphthyl. In some embodiments, $R^{10}$ is —$N(R^B)_2$, —$N(R^A)C(O)R^A$, or —$N(R^A)C(O)OR^A$. In some embodiments, $R^A$ is independently hydrogen or optionally substituted alkyl. In some embodiments, $R^A$ is independently hydrogen, methyl or ethyl. In some embodiments, $R^B$ is independently hydrogen or optionally substituted alkyl. In some embodiments, $R^B$ is independently hydrogen, methyl or ethyl. In some embodiments, each $R^B$ is hydrogen. In some embodiments, each $R^B$ is methyl. In some embodiments, $R^{10}$ is hydrogen, —$NH_2$, —$NHC(O)CH_3$, —$NHC(O)O(R^A)$, —$NHR^B$, —$NR^B_2$, wherein $R^B$ can be $C_1$-$C_5$ alkyl. In some embodiments, $R^{10}$ is hydrogen, —$NHC(O)CH_3$, —$NHC(O)O(CH_3)$, —$N(CH_3)_2$, —$NH_2$, or —$NHCH_2CH_3$.

As described generally above, $R^{11}$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^{11}$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^{11}$ is selected from the group consisting of —H, —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^{11}$ is selected from the group consisting of —OH, —Cl, —Br, —F, optionally substituted $C_{1-6}$ alkyl, optionally substituted alkenyl, optionally substituted alkynyl, optionally substituted aryl, —$OR^A$, —$NO_2$, —$N(R^B)_2$, —$C(O)CH_3$, —$CO_2H$, —$C(O)OR^A$, —$C(O)N(R^B)_2$, —CN, heterocyclyl, —$SO_2$-alkyl, and —$SO_2$-aryl. In certain embodiments, $R^{11}$ is selected from the group consisting of —OH, —Cl, —Br, —F, methyl, ethyl, methoxy, ethoxy, —C≡C-aryl, phenyl, naphthyl, —$NO_2$, —NH-$C_{1-6}$ alkyl, —$C(O)CH_3$, —$CO_2H$, —$CO_2Et$, —CONH-aryl, —CN, N-morpholinyl, —$SO_2$-alkyl, and —$SO_2$-aryl. In certain embodiments, $R^{11}$ is hydrogen. In some embodiments, $R^{11}$ is $C_{1-6}$ alkyl. In certain embodiments, $R^{11}$ is —$C(O)OR^A$. In certain embodiments, $R^{11}$ is —$CO_2H$. In certain embodiments, $R^{11}$ is —$C(O)N(R^B)_2$, —$N(R^A)C(O)R^A$, or —$N(R^A)C(O)OR^A$. In some embodiments, $R^{11}$ halogen. In certain embodiments, $R^{11}$ is fluoro. In certain embodiments, $R^{11}$ is chloro. In certain embodiments, $R^{11}$ is bromo. In certain embodiments, $R^{11}$ is iodo. In some embodiments, $R^{11}$ is —$N(R^B)_2$. In some embodiments, $R^{11}$ is —$NH_2$. In some embodiments, $R^{11}$ is —NH-$C_{1-6}$ alkyl. In certain embodiments, $R^{11}$ is —$NHCH_3$. In certain embodiments, $R^{11}$ is —$NO_2$. In some embodiments, $R^{11}$ is optionally substituted naphthyl. In some embodiments, $R^{11}$ is —$N(R^B)_2$, —$N(R^A)C(O)R^A$, or —$N(R^A)C(O)OR^A$. In some embodiments, $R^A$ is independently hydrogen or optionally substituted alkyl. In some embodiments, $R^A$ is independently hydrogen, methyl or ethyl. In some embodiments, $R^B$ is independently hydrogen or optionally substituted alkyl. In some embodiments, $R^B$ is independently hydrogen, methyl or ethyl. In some embodiments, each $R^B$ is hydrogen. In some embodiments, each $R^B$ is methyl. In some embodiments, $R^{11}$ is hydrogen, —$NH_2$, —$NHC(O)CH_3$, —$NHC(O)O(R^A)$, —$NHR^B$, —$NR^B_2$, wherein $R^B$ can be $C_1$-$C_5$ alkyl. In some embodiments, $R^{11}$ is hydrogen, —$NHC(O)CH_3$, —$NHC(O)O(CH_3)$, —$N(CH_3)_2$, —$NH_2$, or —$NHCH_2CH_3$.

As described generally above, $R^{12}$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)OR^A$—$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$. In certain embodiments, $R^{12}$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$N(R^A)C(O)$ $OR^A$, —C(O)N($R^B$)$_2$, —CN, —NO$_2$, —C(O)$R^A$, —C(O)$OR^A$, —S(O)$R^A$, —SO$_2$$R^A$, —SO$_2$N($R^B$)$_2$, and —NHSO$_2$$R^B$. In certain embodiments, $R^{12}$ is selected from the group consisting of —H, —OH, —Cl, —Br, —F, optionally substituted $C_{1-6}$ alkyl, optionally substituted alkenyl, optionally substituted alkynyl, optionally substituted aryl, —$OR^A$, —NO$_2$, —N($R^B$)$_2$, —C(O)CH$_3$, —CO$_2$H, —C(O)$OR^A$, —C(O)N($R^B$)$_2$, —CN, heterocyclyl, —SO$_2$-alkyl, and —SO$_2$-aryl. In certain embodiments, $R^{12}$ is selected from the group consisting of —OH, —Cl, —Br, —F, optionally substituted $C_{1-6}$ alkyl, optionally substituted alkenyl, optionally substituted alkynyl, optionally substituted aryl, —$OR^A$, —NO$_2$, —N($R^B$)$_2$, —C(O)CH$_3$, —CO$_2$H, —C(O)$OR^A$, —C(O)N($R^B$)$_2$, —CN, heterocyclyl, —SO$_2$-alkyl, and —SO$_2$-aryl. In certain embodiments, $R^{12}$ is selected from the group consisting of —H, —OH, —Cl, —Br, —F, methyl, ethyl, methoxy, ethoxy, —C≡C-aryl, phenyl, naphthyl, —NO$_2$, —NH-$C_{1-6}$ alkyl, —C(O)CH$_3$, —CO$_2$H, —CO$_2$Et, —CONH-aryl, —CN, N-morpholinyl, —SO$_2$-alkyl, and —SO$_2$-aryl. In certain embodiments, $R^{12}$ is hydrogen. In some embodiments, $R^{12}$ is $C_{1-6}$ alkyl. In certain embodiments, $R^{12}$ is —C(O)$OR^A$. In certain embodiments, $R^{12}$ is —CO$_2$H. In certain embodiments, $R^{12}$ is —C(O)N($R^B$)$_2$, —N($R^A$)C(O)$R^A$, or —N($R^A$)C(O)$OR^A$. In some embodiments, $R^{12}$ is halogen. In certain embodiments, $R^{12}$ is fluoro. In certain embodiments, $R^{12}$ is chloro. In certain embodiments, $R^{12}$ is bromo. In certain embodiments, $R^{12}$ is iodo. In some embodiments, $R^{12}$ is —N($R^B$)$_2$. In some embodiments, $R^{12}$ is —NH$_2$. In some embodiments, $R^{12}$ is —NH-$C_{1-6}$ alkyl. In certain embodiments, $R^{12}$ is —NHCH$_3$. In certain embodiments, $R^{12}$ is —NO$_2$. In some embodiments, $R^{12}$ is optionally substituted naphthyl.

As described generally above, $R^{13}$ is selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —OC(O)$R^A$, —S$R^A$, —N($R^B$)$_2$, —N($R^A$)C(O)$R^A$, —N($R^A$)C(O)$OR^A$, —C(O)N($R^B$)$_2$, —CN, —NO$_2$, —C(O)$R^A$, —C(O)$OR^A$, —S(O)$R^A$, —SO$_2$$R^A$, —SO$_2$N($R^B$)$_2$, and —NHSO$_2$$R^B$. In certain embodiments, $R^{13}$ is selected from the group consisting of halogen, optionally substituted alkyl, optionally substituted alkenyl, optionally substituted alkynyl, optionally substituted heterocyclyl, optionally substituted heteroaryl, optionally substituted aryl, —$OR^A$, —OC(O)$R^A$, —S$R^A$, —N($R^B$)$^2$, —N($R^A$)C(O)$R^A$, —N($R^A$)C(O)$OR^A$, —C(O)N($R^B$)$_2$, —CN, —NO$_2$, —C(O)$R^A$, —C(O)$OR^A$, —S(O)$R^A$, —SO$_2$$R^A$, —SO$_2$N($R^B$)$_2$, and —NHSO$_2$$R^B$. In certain embodiments, $R^{13}$ is selected from the group consisting of —H, —OH, —Cl, —Br, —F, optionally substituted $C_{1-6}$ alkyl, optionally substituted alkenyl, optionally substituted alkynyl, optionally substituted aryl, —$OR^A$, —NO$_2$, —N($R^B$)$_2$, —C(O)CH$_3$, —CO$_2$H, —C(O)$OR^A$, —C(O)N($R^B$)$_2$, —CN, heterocyclyl, —SO$_2$-alkyl, and —SO$_2$-aryl. In certain embodiments, $R^{13}$ is selected from the group consisting of —OH, —Cl, —Br, —F, optionally substituted $C_{1-6}$ alkyl, optionally substituted alkenyl, optionally substituted alkynyl, optionally substituted aryl, —$OR^A$, —NO$_2$, —N($R^B$)$_2$, —C(O)CH$_3$, —CO$_2$H, —C(O)$OR^A$, —C(O)N($R^B$)$_2$, —CN, heterocyclyl, —SO$_2$-alkyl, and —SO$_2$-aryl. In certain embodiments, $R^{13}$ is selected from the group consisting of —H, —OH, —Cl, —Br, —F, methyl, ethyl, methoxy, ethoxy, —C≡C-aryl, phenyl, naphthyl, —NO$_2$, —NH-$C_{1-6}$ alkyl, —C(O)CH$_3$, —CO$_2$H, —CO$_2$Et, —CONH-aryl, —CN, N-morpholinyl, —SO$_2$-alkyl, and —SO$_2$-aryl. In certain embodiments, $R^{13}$ is hydrogen. In some embodiments, $R^{13}$ is $C_{1-6}$ alkyl. In certain embodiments, $R^{13}$ is —C(O)$OR^A$. In certain embodiments, $R^{13}$ is —CO$_2$H. In certain embodiments, $R^{13}$ is —C(O)N($R^B$)$_2$, —N($R^A$)C(O)$R^A$ or —N($R^A$)C(O)$OR^A$. In some embodiments, $R^{13}$ is halogen. In certain embodiments, $R^{13}$ is fluoro. In certain embodiments, $R^{13}$ is chloro. In certain embodiments, $R^{13}$ is bromo. In certain embodiments, $R^{13}$ is iodo. In some embodiments, $R^{13}$ is —N($R^B$)$_2$. In some embodiments, $R^{13}$ is —NH$_2$. In some embodiments, $R^{13}$ is —NH-$C_{1-6}$ alkyl. In certain embodiments, $R^{13}$ is —NHCH$_3$. In certain embodiments, $R^{13}$ is —NO$_2$. In some embodiments, $R^{13}$ is optionally substituted naphthyl.

As described generally above, $R^{14}$ is hydrogen, optionally substituted alkyl, optionally substituted alkenyl, optionally substituted alkynyl, optionally substituted heterocyclyl, optionally substituted heteroaryl, or optionally substituted aryl. In certain embodiments, $R^{14}$ is hydrogen. In some embodiments, $R^{14}$ is optionally substituted alkyl, optionally substituted alkenyl, optionally substituted alkynyl, optionally substituted heterocyclyl or optionally substituted aryl. In certain embodiments, $R^{14}$ is optionally substituted $C_{1-6}$ alkyl. $R^{14}$ is substituted $C_{1-6}$ alkyl. In certain embodiments, $R^{14}$ is unsubstituted $C_{1-6}$ alkyl. In certain embodiments, $R^{14}$ is methyl, ethyl, propyl, butyl, pentyl, or hexyl. In certain embodiments, $R^{14}$ is isopropyl, isobutyl, or isoamyl. In certain embodiments, $R^{14}$ is isobutyl. In certain embodiments, $R^{14}$ is tert-butyl. In certain embodiments, $R^{14}$ is —(CH$_2$)$_n$—N($R^B$)$_2$, wherein n is 1, 2, 3, 4, 5, or 6 and wherein $R^B$ is independently optionally substituted $C_{1-6}$ alkyl or two $R^B$ are taken together with the intervening atoms to form a heterocycle with at least 1-4 heteroatoms. In certain embodiments, the heterocycle is a 3-8 membered ring. In certain embodiments, the heterocycle formed is In certain embodiments, $R^{14}$ is —(CH$_2$)$_n$—N($R^B$)$_2$, wherein n is 1, 2, 3, 4, or 5, and wherein $R^B$ is independently optionally substituted $C_{1-6}$ alkyl or two $R^B$ are taken together with the intervening atoms to form a heterocycle . In certain embodiments, n is 1. In certain embodiments, n is 2. In certain embodiments, n is 3. In certain embodiments, n is 4. In certain embodiments, n is 5. In certain embodiments, n is 6. In certain embodiments, $R^{14}$ is —(CH$_2$)$_n$—NH$R^B$. In certain embodiments, $R^{14}$ is —(CH$_2$)$_n$—NH$R^B$, wherein $R^B$ is optionally substituted $C_{1-6}$ alkyl. In certain embodiments, $R^{14}$ is —(CH$_2$)$_n$—NH$R^B$, wherein $R^B$ is unsubstituted $C_{1-6}$ alkyl. In certain embodiment, $R^{14}$ is —(CH$_2$)$_n$—NH$R^B$, wherein $R^B$ is substituted $C_{1-6}$ alkyl. In certain embodiments, $R^{14}$ is —(CH$_2$)$_n$—N(CH$_3$)$R^B$, wherein each $R^B$ is independently optionally substituted $C_{1-6}$ alkyl. In certain embodiments, $R^{14}$ is —(CH$_2$)$_n$—N(CH$_3$)$R^B$, wherein each $R^B$ is independently unsubstituted $C_{1-6}$ alkyl. In certain embodiments, $R^{14}$ is —(CH$_2$)$_n$—N(CH$_3$)$_2$. In certain embodiments, $R^{14}$ is —(CH$_2$)$_n$—N(CH$_2$CH$_3$)$R^B$, wherein each $R^B$ is independently optionally substituted $C_{1-6}$ alkyl. In certain embodiments, $R^{14}$ is —(CH$_2$)$_n$—N(CH$_2$CH$_3$)$R^B$, wherein each $R^B$ is independently unsubstituted $C_{1-6}$ alkyl. In certain embodiments, $R^{14}$ is —(CH$_2$)$_n$—N($R^B$)$_2$, wherein each $R^B$ is independently selected from the group consisting of methyl, ethyl, isopropyl, isobutyl, isoamyl, and benzyl. In some embodiments, $R^{14}$ is —(CH$_2$)$_n$—N($R^B$)$_2$, wherein each $R^B$ is the same. In some embodiments, $R^{14}$ is —(CH$_2$)$_n$—N($R^B$)$_2$, wherein each $R^B$ is different. In certain embodiments, $R^{14}$ is —(CH$_2$)$_n$—NH$_2$. In certain embodiments, $R^{14}$ is —(CH$_2$)$_2$N(CH$_3$)$_2$. In certain embodiments, $R^{14}$ comprises a carboxylic acid or tetra-ammonium moiety. In certain embodiments, $R^{14}$ is —(CH$_2$)$_s$—CO$_2$$R^A$, wherein s is 1, 2, 3, 4, 5, or 6. In certain embodiments, $R^{14}$ is —(CH$_2$)$_s$—CO$_2$H. In some embodiments, s is 1. In some embodiments, s is 2. In some embodiments, s is 3. In some embodiments, s is 4. In some embodiments, s is 5. In some embodiments, s is 6. In certain embodiments, $R^{14}$ is $-CH_2-CO_2R^A$, wherein $R^A$ is hydrogen or optionally substituted alkyl. In certain embodiments, $R^{14}$ is $-CH_2-CO_2NR^C_3$, wherein $R^C$ is an optionally substituted $C_{1-6}$ alkyl, wherein the optional substituent is a hydroxyl. In certain embodiments, $R^C$ is $-(CH_2)_2OH$, $-(CH_2)_2OH$, $-(CH_2)_3OH$, $-(CH_2)_4OH$, $-(CH_2)_5OH$. In certain embodiments, $R^{14}$ is $-C(O)O$-methyl. In certain embodiments, $R^{14}$ is $-C(O)O$-ethyl. In certain embodiments, $R^{14}$ is $-C(O)O$-propyl, $-OC(O)$-isopropyl, $-C(O)O$-isobutyl, or $-OC(O)$-isoamyl. In certain embodiments, $R^{14}$ is $-(CH_2)_2-CO_2R^A$, wherein $R^A$ is hydrogen or optionally substituted alkyl. In certain embodiments, $R^{14}$ is $-(CH_2)_3-CO_2R^A$, wherein $R^A$ is hydrogen or optionally substituted alkyl. In certain embodiments, $R^{14}$ is $-(CH_2)_4-CO_2R^A$, wherein $R^A$ is hydrogen or optionally substituted alkyl. In certain embodiments, $R^{14}$ is $-(CH_2)_5-CO_2R^A$, wherein $R^A$ is hydrogen or optionally substituted alkyl. In certain embodiments, $R^{14}$ is $-(CH_2)_6-CO_2R^A$, wherein $R^A$ is hydrogen or optionally substituted alkyl.

In certain embodiments, $R^{14}$ is optionally substituted aryl. In some embodiments, $R^{14}$ is of the following structure:

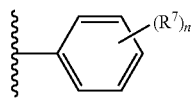

wherein:

each instance of $R^7$ is independently selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, $-OR^A$, $-OC(O)R^A$, $-SR^A$, $-N(R^B)_2$, $-N(R^A)C(O)R^A$, $-C(O)N(R^B)_2$, $-CN$, $-NO_2$, $-C(O)R^A$, $-C(O)OR^A$, $-S(O)R^A$, $-SO_2R^A$, $-SO_2N(R^B)_2$, and $-NHSO_2R^B$;

each instance of $R^A$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl;

each instance of $R^B$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl, or two $R^B$ are taken together with the intervening atoms to form a heterocycle; and n is 0, 1, 2, 3, 4 or 5.

As generally defined herein, n is 0, 1, 2, 3, 4, or 5. In certain embodiments, n is 0 and $R^{14}$ is phenyl. In certain embodiments, n is 1 and $R^{14}$ is of the formula

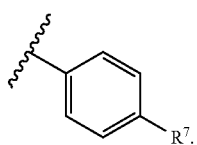

In certain embodiments, n is 1 and $R^{14}$ is of the formula

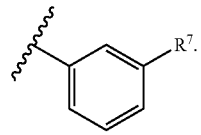

In certain embodiments, n is 1 and $R^{14}$ is of the formula

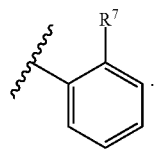

In certain embodiments, n is 2 and $R^{14}$ is of the formula

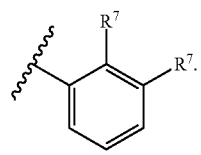

In certain embodiments, n is 2 and $R^{14}$ is of the formula

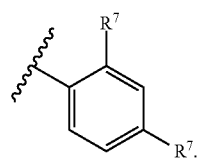

In certain embodiments, n is 2 and $R^{14}$ is of the formula

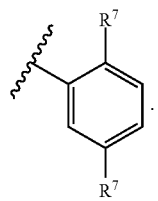

In certain embodiments, n is 2 and $R^{14}$ is of the formula

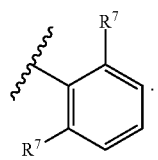

In certain embodiments, In certain embodiments, n is 2 and $R^{14}$ is of the formula

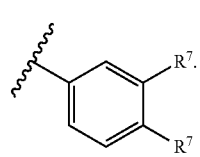

In certain embodiments, In certain embodiments, n is 2 and $R^{14}$ is of the formula

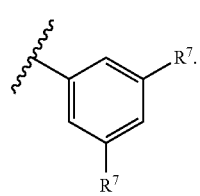

In certain embodiments, n is 3 and $R^{14}$ is of the formula

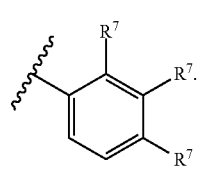

In certain embodiments, n is 3 and $R^{14}$ is of the formula

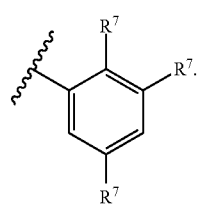

In certain embodiments, n is 3 and $R^{14}$ is of the formula

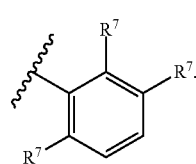

In certain embodiments, n is 3 and $R^{14}$ is of the formula

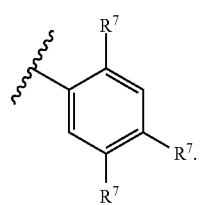

In certain embodiments, n is 3 and $R^{14}$ is of the formula

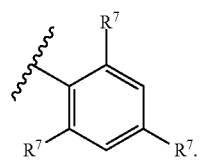

In certain embodiments, n is 4 and $R^{14}$ is of the formula

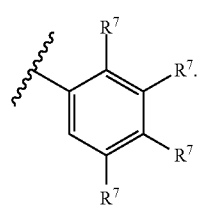

In certain embodiments, n is 4 and $R^{14}$ is of the formula

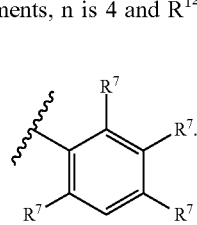

In certain embodiments, n is 4 and $R^{14}$ is of the formula

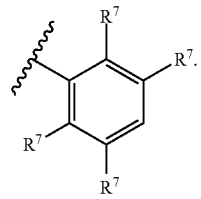

In certain embodiments, n is 4 and $R^{14}$ is of the formula

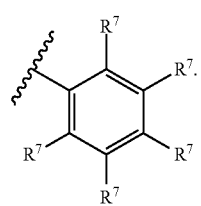

In certain embodiments, n is 5 and $R^{14}$ is of the formula

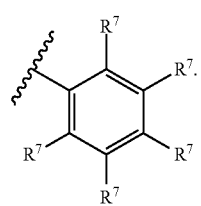

In certain embodiments, $R^7$ is hydrogen. In some embodiments, $R^7$ is halo. In certain embodiments, $R^7$ is fluoro. In certain embodiments, $R^7$ is chloro. In certain embodiments, $R^7$ is bromo. In certain embodiments, $R^7$ is iodo. In some embodiments, $R^7$ is optionally substituted alkyl, optionally substituted alkenyl, optionally substituted alkynyl, optionally substituted heterocyclyl or optionally substituted aryl. In certain embodiments, $R^7$ is optionally substituted $C_{1-6}$ alkyl. In certain embodiments, $R^7$ is substituted $C_{1-6}$ alkyl. In certain embodiments, $R^7$ is substituted methyl, ethyl, propyl, butyl, pentyl, or hexyl. In certain embodiments, $R^7$ is $CH_2F$.

In certain embodiments, $R^7$ is $CHF_2$. In certain embodiments, $R^7$ is $CF_3$. In certain embodiments, $R^7$ is —$(CH_2)_s$—$CO_2R^A$, wherein s is 1, 2, 3, 4, 5, or 6. In certain embodiments, $R^7$ is —$(CH_2)_s$—$CO_2H$. In some embodiments, s is 1. In some embodiments, s is 2. In some embodiments, s is 3. In some embodiments, s is 4. In some embodiments, s is 5. In some embodiments, s is 6. In certain embodiments, $R^7$ is —$CH_2$—$CO_2R^A$, wherein $R^A$ is hydrogen or optionally substituted alkyl. In certain embodiments, $R^7$ is —C(O)O-methyl. In certain embodiments, $R^7$ is —C(O)O-ethyl. In certain embodiments, $R^7$ is —C(O)O-propyl, —OC(O)-isopropyl, —C(O)O-isobutyl, or —OC(O)-isoamyl. In certain embodiments, $R^7$ is —$(CH_2)_2$—$CO_2R^A$, wherein $R^A$ is hydrogen or optionally substituted alkyl. In certain embodiments, $R^7$ is —$(CH_2)_3$—$CO_2R^A$, wherein $R^A$ is hydrogen or optionally substituted alkyl. In certain embodiments, $R^7$ is —$(CH_2)_4$—$CO_2R^A$, wherein $R^A$ is hydrogen or optionally substituted alkyl. In certain embodiments, $R^7$ is —$(CH_2)_5$—$CO_2R^A$, wherein $R^A$ is hydrogen or optionally substituted alkyl. In certain embodiments, $R^7$ is —$(CH_2)_6$—$CO_2R^A$, wherein $R^A$ is hydrogen or optionally substituted alkyl.

In certain embodiments, $R^7$ is unsubstituted $C_{1-6}$ alkyl. In certain embodiments, $R^7$ is methyl, ethyl, propyl, butyl, pentyl, or hexyl. In certain embodiments, $R^7$ is isopropyl, isobutyl, or isoamyl. In certain embodiments, $R^7$ is isobutyl. In certain embodiments, $R^7$ is tert-butyl.

In certain embodiments, $R^7$ is —$OR^A$. In certain embodiments, $R^7$ is —OH. In certain embodiments, $R^7$ is —$OR^A$, wherein $R^A$ is optionally substituted alkyl. In certain embodiments, $R^7$ is —O-methyl. In certain embodiments, $R^7$ is —O-ethyl. In certain embodiments, $R^7$ is —O-propyl, —O-isopropyl, —O-isobutyl, or —O-isoamyl.

In certain embodiments, $R^7$ is —$N(R^B)_2$, wherein each $R^B$ is independently selected from the group consisting of methyl, ethyl, isopropyl, isobutyl, isoamyl, and benzyl. In some embodiments, $R^7$ is —$N(R^B)_2$, wherein each $R^B$ is the same. In some embodiments, $R^7$ is —$N(R^B)_2$, wherein each $R^B$ is different. In certain embodiments, $R^7$ is —$NH_2$.

In certain embodiments, $R^7$ is —$CO_2R^A$. In certain embodiments, $R^7$ is —$CO_2H$. In certain embodiments, $R^7$ is —$CO_2R^A$, wherein $R^A$ is optionally substituted alkyl. In certain embodiments, $R^7$ is —C(O)O-methyl. In certain embodiments, $R^7$ is —C(O)O-ethyl. In certain embodiments, $R^7$ is —C(O)O-propyl, —OC(O)-isopropyl, —C(O)O-isobutyl, or —OC(O)-isoamyl.

In some embodiments, at least two of $R^8$, $R^9$, $R^{10}$, $R^{11}$, $R^{12}$, and $R^{13}$ are hydrogen. In certain embodiments, $R^8$, $R^9$, $R^{12}$, and $R^{13}$ are hydrogen. In certain embodiments, $R^{12}$, and $R^{13}$ are are hydrogen. In certain embodiments, $R^8$, $R^9$, $R^{10}$ are hydrogen. In certain embodiments, $R^8$, $R^9$, and $R^{11}$ are hydrogen. In certain embodiments, $R^{11}$ and $R^{12}$ are hydrogen. In some embodiments, at least two of $R^8$, $R^9$, $R^{10}$, $R^{11}$, $R^{12}$, and $R^{13}$ are each hydrogen, and $R1^4$ is hydrogen. In some embodiments, $R^8$, $R^9$, $R^{11}$, $R^{12}$, and $R^{13}$ are hydrogen.

In some embodiments of Formula (V-a), $R^{15}$ and $R^{16}$ are each hydrogen. In certain embodiments, the present disclosure employs a compound of Formula (VI):

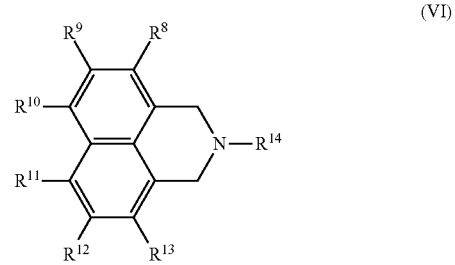

or a pharmaceutically acceptable salt, solvate, or hydrate thereof, wherein $R^8$, $R^9$, $R^{10}$, $R^{11}$, $R^{12}$, $R^{13}$, and $R^{14}$ are as described herein for Formula (V-a).

In some embodiments of Formula (VI), $R^8$, $R^9$, $R^{11}$, $R^{12}$, and $R^{13}$ are each hydrogen. In certain embodiments, the present disclosure employs a compound of Formula (VI-a):

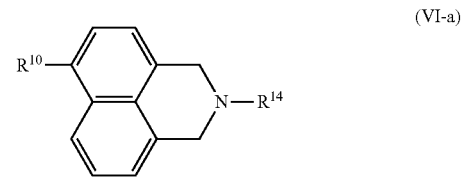

or a pharmaceutically acceptable salt, solvate, or hydrate thereof, wherein $R^{10}$ and $R^{14}$ are as described herein for Formula (V-a). In some examples, $R^{10}$ and $R^{14}$, independently, are hydrogen, optionally substituted $C_{1-6}$ alkyl, —$NR^B_2$, —$N(R^A)C(O)R^A$, —$N(R^A)C(O)OR^A$ or hydroxyl.

In some embodiments of Formula (V-a), $R^{15}$ is hydroxyl and $R^{16}$ is oxygen connected via a double bond. In certain embodiments, the present disclosure employs a compound of Formula (VII):

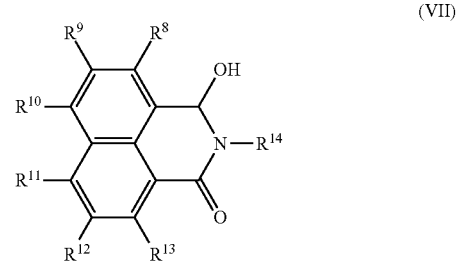

or a pharmaceutically acceptable salt, solvate, or hydrate thereof, wherein $R^8$, $R^9$, $R^{10}$, $R^{11}$, $R^{12}$, $R^{13}$, and $R^{14}$ are as described herein for Formula (V-a).

In some embodiments of Formula (VII), $R^8$, $R^9$, $R^{11}$, $R^{12}$, and $R^{13}$ are each hydrogen. In some embodiments, $R^8$, $R^9$, $R^{10}$, $R^{12}$, and $R^{13}$ are each hydrogen. In some embodiments, $R^8$, $R^9$, $R^{12}$, and $R^{13}$ are each hydrogen. In certain embodiments, the present disclosure employs a compound of Formula (VII-a):

(VII-a)

or a pharmaceutically acceptable salt, solvate, or hydrate thereof, wherein $R^{10}$, $R^{11}$, and $R^{14}$ are as described herein for Formula (V-a). In some examples, $R^{10}$, $R^{11}$, and $R^{14}$, independently, are hydrogen, optionally substituted $C_{1-6}$ alkyl, $-NR^B{}_2$, $-N(R^A)C(O)R^A$, $-N(R^A)C(O)OR^A$ or hydroxyl.

In some embodiments of Formula (V-a), $R^{15}$ is hydrogen and $R^{16}$ is oxygen connected via a double bond. In certain embodiments, the present disclosure employs a compound of Formula (VIII):

(VIII)

or a pharmaceutically acceptable salt, solvate, or hydrate thereof, wherein $R^8$, $R^9$, $R^{10}$, $R^{11}$, $R^{12}$, $R^{13}$, $R^{14}$ are as described herein for Formula (V-a).

In some embodiments of Formula (VIII), $R^8$, $R^9$, $R^{11}$, $R^{12}$, $R^{13}$ are each hydrogen. In some embodiments, $R^8$, $R^9$, $R^{10}$, $R^{12}$, $R^{13}$, and $R^{15}$ are each hydrogen. In some embodiments, $R^8$, $R^9$, $R^{12}$, $R^{13}$, and $R^{15}$ are each hydrogen. In certain embodiments, the present disclosure employs a compound of Formula (VIII-a):

(VIII-a)

or a pharmaceutically acceptable salt, solvate, or hydrate thereof, wherein $R^{10}$, $R^{11}$, and $R^{14}$ are as described herein for Formula (V-a). In some examples, $R^{10}$, $R^{11}$, and $R^{14}$, independently, are hydrogen, optionally substituted $C_{1-6}$ alkyl, $-NR^B{}_2$, $-N(R^A)C(O)R^A$, $-N(R^A)C(O)OR^A$ or hydroxyl.

In some embodiments of Formula (V-a), $R^{15}$ is hydrogen and $R^{16}$ is hydroxyl. In certain embodiments, the present disclosure employs a compound of Formula (IX):

(IX)

or a pharmaceutically acceptable salt, solvate, or hydrate thereof, wherein $R^8$, $R^9$, $R^{10}$, $R^{11}$, $R^{12}$, $R^{13}$ and $R^{14}$ are as described herein for Formula (V-a).

In some embodiments of Formula (IX), $R^8$, $R^9$, $R^{12}$, $R^{13}$, and $R^{15}$ are each hydrogen. In some embodiments of Formula (IX), $R^8$, $R^9$, $R^{10}$, $R^{12}$, $R^{13}$, and $R^{15}$ are each hydrogen. In some embodiments of Formula (IX), $R^8$, $R^9$, $R^{11}$, $R^{12}$, $R^{13}$, and $R^{15}$ are each hydrogen. In certain embodiments, the present disclosure employs a compound of Formula (IX-a):

(IX-a)

or a pharmaceutically acceptable salt, solvate, or hydrate thereof, wherein $R^{10}$, $R^{11}$, and $R^{14}$ are as described herein for Formula (V-a). In some examples, $R^{10}$, $R^{11}$, and $R^{14}$, independently, are hydrogen, optionally substituted $C_{1-6}$ alkyl, $-NR^B{}_2$, $-N(R^A)C(O)R^A$, $-N(R^A)C(O)OR^A$ or hydroxyl.

In some embodiments of Formula (V-a), $R^{15}$ and $R^{16}$ are each hydroxyl. In certain embodiments, the present disclosure employs a compound of Formula (X):

(X)

or a pharmaceutically acceptable salt, solvate, or hydrate thereof, wherein $R^8$, $R^9$, $R^{10}$, $R^{11}$, $R^{12}$, $R^{13}$ and $R^{14}$ are as described herein for Formula (V-a).

In some embodiments, $R^8$, $R^9$, $R^{11}$, $R^{12}$, and $R^{13}$ of Formula (X) are each hydrogen. In certain embodiments, the present disclosure employs a compound of Formula (X):

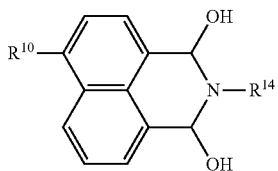

(X-a)

or a pharmaceutically acceptable salt, solvate, or hydrate thereof, wherein $R^{10}$ and $R^{14}$ are as described herein for Formula (V-a). In some examples, $R^{10}$ and $R^{14}$, independently, are hydrogen, optionally substituted $C_{1-6}$ alkyl, $-NR^B{}_2$, $-N(R^A)C(O)R^A$, $-N(R^A)C(O)OR^A$ or hydroxyl.

In some embodiments of Formula (V-a), $R^{15}$ and $R^{16}$ are each hydrogen. In certain embodiments, the present disclosure employs a compound of Formula (XI):

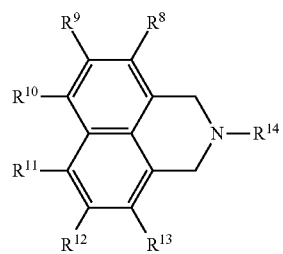

(XI)

or a pharmaceutically acceptable salt, solvate, or hydrate thereof, wherein $R^8$, $R^9$, $R^{10}$, $R^{11}$, $R^{12}$, $R^{13}$, and $R^{14}$ are as described herein for Formula (V-a).

In some embodiments, $R^8$, $R^9$, $R^{11}$, $R^{12}$, and $R^{13}$ of Formula (XI) are each hydrogen. In certain embodiments, the present disclosure employs a compound of Formula (XI-a):

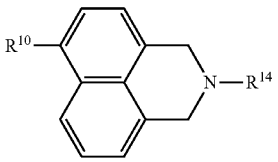

(xi-A)

or a pharmaceutically acceptable salt, solvate, or hydrate thereof, wherein $R^{10}$ and $R^{14}$ are as described herein for Formula (V-a). In some examples, $R^{10}$ and $R^{14}$, independently, are hydrogen, optionally substituted $C_{1-6}$ alkyl, $-NR^B{}_2$, $-N(R^A)C(O)R^A$, $-N(R^A)C(O)OR^A$ or hydroxyl.

In some embodiments of the present disclosure is a compound represented by formula (V-a), (VI), (VI-a), (VII), (VII-a), (VIII), (VIII-a), (IX), (IX-a), (X), (X-a), (XI), and/or (XI-a) or a pharmaceutically acceptable salt thereof, wherein $R^{10}$ is $-N(R^B)_2$, $-N(R^A)C(O)R^A$, or $-N(R^A)C(O)OR^A$ and $R^{14}$ is an optionally substituted alkyl. In some embodiments, $R^A$ is independently hydrogen or optionally substituted alkyl. In some embodiments, $R^A$ is independently hydrogen, methyl or ethyl. In some embodiments, $R^B$ is independently hydrogen or optionally substituted alkyl. In some embodiments, $R^B$ is independently hydrogen, methyl or ethyl. In some embodiments, each $R^B$ is hydrogen. In some embodiments, each $R^B$ is methyl. In some embodiments, $R^{10}$ is hydrogen, $-NH_2$, $-NHC(O)CH_3$, $-NHC(O)OR^A$, $-NHR^B$, $-NR^B{}_2$, wherein $R^B$ can be $C_1$-$C_5$ alkyl. In some embodiments, $R^{10}$ is hydrogen, $-NHC(O)CH_3$, $-NHC(O)O(CH_3)$, $-N(CH_3)_2$, $-NH_2$, or $-NHCH_2CH_3$.

In some embodiments, $R^{14}$ is an optionally substituted alkyl. In certain embodiments, $R^{14}$ is an optionally substituted methyl, ethyl, propyl, butyl, pentyl, or hexyl. In certain embodiments, $R^{14}$ is $-(CH_2)_n-N(R^B)_2$, wherein n is 1, 2, 3, 4, 5, or 6 and wherein $R^B$ is independently optionally substituted $C_{1-6}$ alkyl or two $R^B$ are taken together with the intervening atoms to form a heterocycle with at least 1-4 heteroatoms. In certain embodiments, the heterocycle is a 3-8 membered ring. In certain embodiments, $R^{14}$ is $-(CH_2)_n-N(R^B)_2$, wherein n is 2. In certain embodiments, $R^{14}$ is $-(CH_2)_2NH_2$. In certain embodiments, $R^{14}$ comprises a carboxylic acid or tetra-ammonium moiety. In certain embodiments, $R^{14}$ is $-(CH_2)_n-COOH$ or $-(CH_2)_n-COONR^C{}_3$ or, wherein n is 1, 2, 3, 4, 5, or 6 and $R^C$ is an optionally substituted $C_{1-6}$ alkyl, wherein the optional substituent is a hydroxyl. In certain embodiments, $R^C$ is $-(CH_2)_2OH$, $-(CH_2)_2OH$, $-(CH_2)_3OH$, $-(CH_2)_4OH$, $-(CH_2)_5OH$.

In certain embodiments, exemplary compounds of the present disclosure is one of the compounds provided below or analogues thereof:

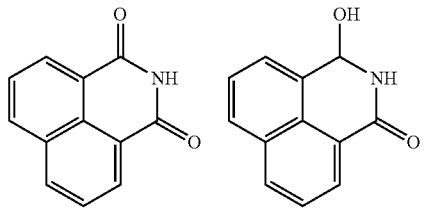

1H-benzo[d3]isoquinoline-1,3(2H)-dione 3-hydroxy-2,3-dihydro-1H-benzo[de]isoquinolin-1-one

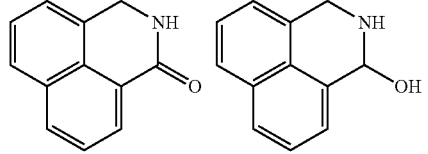

2,3-dihydro-1H-benzo-[de]isoquinolin-1-one 2,3-dihydro-1H-benzo[de]-isoquinolin-1-ol

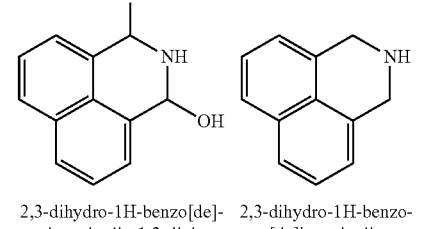

2,3-dihydro-1H-benzo[de]-isoquinolin-1,3-diol 2,3-dihydro-1H-benzo-[de]isoquinolin In some embodiments, a compound of the present disclosure is 1H-benzo[de]isoquinoline-1,3(2H)-dione or analogues thereof as represented by formula A, I-a, II, III, IV, III-a, or III-b. In some embodiments, a compound of the present disclosure is 2,3-dihydro-1H-benzo[de]isoquinoline-1-one or analogues thereof as represented by formula V-a, VIII, or VIII-a. In some embodiments, a compound of the present disclosure is 2,3-dihydro-1H-benzo[de]isoquinoline or analogues thereof as represented by formula V-a, XI, or XI-a. In some embodiments, a compound of the present disclosure is 2,3-dihydro-1H-benzo[de]isoquinoline-1,3-diol or analogues thereof as represented by formula V, X, or X-a. In some embodiments, a compound of the present disclosure is 2,3-dihydro-1H-benzo[de]isoquinolin-1-ol or analogues thereof as represented by formula V, IX, or IX-a. In some embodiments, a compound of the present disclosure is 3-hydroxy-2,3-dihydro-1H-benzo[de]isoquinoline-1-one or analogues thereof as represented by formula V, VII, or VII-a.

In an alternative embodiment, a compound of the present disclosure is depicted by a compound in Table 2 or a pharmaceutically acceptable salt, solvate, or hydrate thereof.

TABLE 2

Structures of Examplary Compounds

| BO number | Structure |
|---|---|
| BO-2566 | 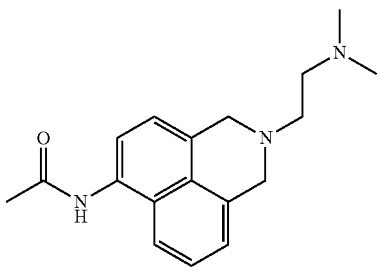 [SMILES: CC(=O)Nc1ccc2c3c(cccc13)CN(CCN(C)C)C2] |
| BO-2563 | 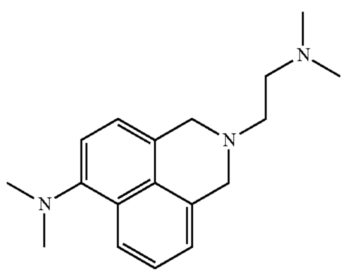 |
| BO-2560 | 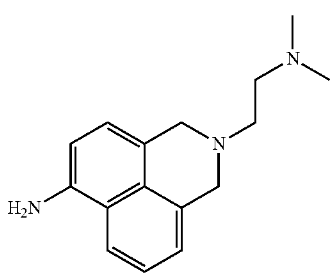 [SMILES: CN(C)CCN1Cc2cccc3c(N)ccc(c23)C1] |
| BO-2565 | 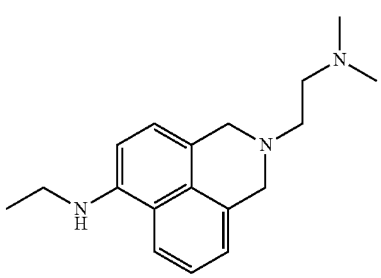 [SMILES: CCNc1ccc2c3c(cccc13)CN(CCN(C)C)C2] |

TABLE 2-continued

Structures of Examplary Compounds

| BO number | Structure |
|---|---|
| BO-2477 | 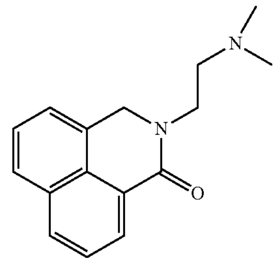 [SMILES: CN(C)CCN1Cc2cccc3cccc(c23)C1=O] |
| BO-2476 | 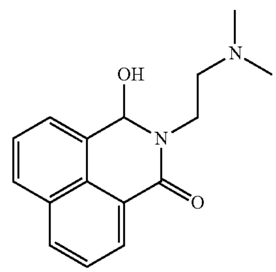 [SMILES: CN(C)CCN1C(=O)c2cccc3cccc(c23)C1O] |
| BO-2478 | 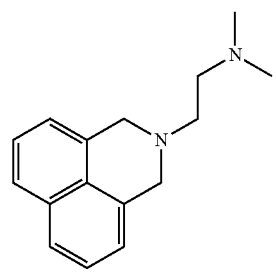 [SMILES: CN(C)CCN1Cc2cccc3cccc(c23)C1] |

Pharmaceutical Compositions

Pharmaceutical compositions of the present disclosure and for use in accordance with the present disclosure may include a pharmaceutically acceptable excipient or carrier. As used herein, the term "pharmaceutically acceptable carrier" or "pharmaceutically acceptable excipient" means a non-toxic, inert solid, semi-solid or liquid filler, diluent, encapsulating material or formulation auxiliary of any type. *Remington's Pharmaceutical Sciences*, Sixteenth Edition, E. W. Martin (Mack Publishing Co., Easton, Pa., 1980) discloses various excipients used in formulating pharmaceutical compositions and known techniques for the preparation thereof. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this present disclosure can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols, and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this disclosure.

In certain embodiments, the pharmaceutically acceptable topical formulations of the present disclosure comprise at least a compound described herein and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum coreum and into the epidermis or dermis, preferably, with little or no systemic absorption. A wide variety of compounds have been evaluated as to their effectiveness in enhancing the rate of penetration of drugs through the skin. See, for example,

*Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). In certain exemplary embodiments, penetration agents for use with the present disclosure include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methyl pyrrolidone.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

In certain embodiments, the compositions may be in the form of ointments, pastes, creams, lotions, gels, powders, solutions, sprays, inhalants. or patches. In certain exemplary embodiments, formulations of the compositions according to the present disclosure are creams, which may further contain saturated or unsaturated fatty acids such as stearic acid, palmitic acid, oleic acid, palmito-oleic acid, cetyl or oleyl alcohols, stearic acid being particularly preferred. Creams of the present disclosure may also contain a non-ionic surfactant, for example, polyoxy-40-stearate. In certain embodiments, the active component is admixed under sterile conditions with a pharmaceutically acceptable excipient and any needed preservatives or buffers as may be required. Ophthalmic formulations, eardrops, and eye drops are also contemplated as being within the scope of this disclosure. Additionally, the present disclosure contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix (e.g., PLGA) or gel.

The ointments, pastes, creams, and gels may contain excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain excipients such as lactose, talc, silicic acid, aluminum hydroxide, calcium silicates, and polyamide powder, or mixtures of these substances. Sprays can additionally contain customary propellants such as chlorofluorohydrocarbons.

It will also be appreciated that the compounds and pharmaceutical compositions of the present disclosure can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a provided compound may be administered concurrently with another agent effective against β-thalassemia or sickle cell disease), or they may achieve different effects (e.g., control of any adverse effects).

It will also be appreciated that certain of the compounds of present disclosure can exist in free form for treatment, or where appropriate, as a pharmaceutically acceptable derivative thereof. According to the present disclosure, a pharmaceutically acceptable derivative includes, but is not limited to, pharmaceutically acceptable salts, esters, salts of such esters, or a prodrug or other adduct or derivative of a compound described herein which upon administration to a patient in need is capable of providing, directly or indirectly, a compound as otherwise described herein, or a metabolite or residue thereof.

Methods of Treatment

The present disclosure provides compounds that induce γ globin and can produce beneficial therapeutic effects. In certain embodiments, compounds and compositions described herein are used to treat hemoglobinopathies such as sickle cell anemia or β-thalassemia. In certain embodiments, a provided compound or composition is used to treat sickle cell anemia. In certain other embodiments, a provided compound or composition is used to treat β-thalassemia.

Without being bound by theory, the compounds (non-HDACi compounds) described herein can stimulate γ globin expression via regulating both the p38/MAPK signaling pathway and globin gene regulators. As shown in the Examples below, several compounds described herein exhibited better gamma globin-inducing capabilities than hydroxyurea, including higher gamma globin level and superior therapeutic effect ($IC_{50}$/EC). Most importantly, those compounds are able to induce γ globin gene expression in both hydroxyurea-responsive cells and hydroxyurea-resistant cells.

In one aspect, the present disclosure provides methods comprising the compounds described herein, e.g., compounds of Formula A, I, I-a, II, III, IV, III-a, III-b, V-a, VI, VII, VIII, IX, X or XI, or compositions thereof for stimulating γ globin expression comprising: contacting a subject with a compound or a composition described herein under conditions suitable to induce γ globin expression in the subject.

In certain embodiments, the present disclosure provides a method of inducing γ globin comprising: contacting a cell with an effective amount of a compound of Formula A, I, I-a, II, III, IV, III-a, III-b, V-a, VI, VII, VIII, IX, X or XI. In certain embodiments, the present disclosure provides a method of inducing γ globin comprising: administering to a subject an effective amount of a compound of Formula A, I, I-a, II, III, IV, III-a, III-b, V-a, VI, VII, VIII, IX, X or XI.

In certain embodiments, the present disclosure provides a method of treating β-thalassemia or sickle cell anemia, the method comprising: administering an effective amount of one or more of the provided compounds or composition to a patient suffering from, suspected of having, or at risk for β-thalassemia or sickle cell anemia.

In certain embodiments, a provided compound or composition is administered orally. In certain embodiments, a provided compound or composition is administered parenterally. In certain embodiments, a provided compound or composition is administered in combination with an additional therapeutic agent.

The compounds of the present disclosure are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present disclosure will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex, and diet of the subject; the time of administration, mute of administration, and rate of excretion of the specific compound employed; the duration of the treatment; drugs used in combination or coincidental with the specific compound employed; and like factors well known in the medical arts (see, for example, *Goodman and Gilman's The Pharmacological Basis of Therapeutics*, Tenth Edition, A. Gilman, J. Hardman and L. Limbird, eds., McGraw-Bill Press, 155-173, 2001, which is incorporated herein by reference in its entirety).

Methods of Assessing Responsiveness to Hydroxyurea

Hydroxyurea, also known as hydroxycarbamide, is an antineoplastic drug for treating proliferative disorders. It is also used in treating sickle cell disease (SCD). Since a SCD patient's responsiveness to hydroxyurea depends on the expression level of HbF induced by hydroxyurea, the responsiveness of RBC can be used to predict one's responsiveness to hydroxyurea.

To assess whether a patient is responsive to hydroxyurea, a biological sample (e.g., a blood sample) containing RBCs can be collected from the patient and the expression level of a hemoglobin gene, such as a HbF gene, in the RBCs can be measured using a routine method (e.g., real-time PCR). If the expression level of the hemoglobin gene is elevated after treatment of hydroxyurea, this indicates that the patient is reponsive to the treatment. On the other hand, if the expression level of the hemoglobin gene is unchanged or decreased, this indicates that the patient might not be responsive to hydroxyurea treatment. The RBCs can be treated by hydroxyurea in vitro. Alternatively, the blood sample can be obtained from a patient who is subject to hydroxyurea treatment.

A subject identified by the method described herein as inresponsive to a hydroxyurea treatment can be subjected to a different treatment, such as a non-hydroxyurea conventional treatment or using any of the compounds disclosed herein.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Effect of Exemplary Compounds in Inducing HbF

A dual fluorescence reporter assay system was established to screen for the potential HbF-inducing agents. Taking advantage of fluoresence signal detected by fluorometer, these chemical compounds could be surveyed quickly to determine those that can switch-on the fetal γ globin promoter. Application of this dual fluoresence reporter system has successfully led to identification of several heterocyclic compounds with common core structure (benzo[de]benzo[4,5]imidazo[2,1-a]isoquinolin-7-one) and with higher efficacies/specificities in the induction of the embryonic/fetal globin chains. These chemical compounds may be developed into a new generation of therapeutical drugs for the cure of hemoglobinopathies including sickle cell disease and β-thalassemia (e.g., β-thalassemia major).

Materials and Methods

Chemistry. General Information. All commercial chemicals and solvents were reagent grade and were used without further purification. Melting points were determined in open capillaries on a Fargo melting point apparatus and are uncorrected. Thin-layer chromatography was performed on silica gel G60 F254 (Merck) with short-wavelength UV light for visualization. High resolution mass spectra were recorded on a Waters HDMS G1 instrument with ESI+, centroid mode, the samples were dissolved in MeOH. High-performance liquid chromatography was performed on Hitachi L-1230 instrument: column: Kinetex 2.6µ HILIC (150×4.6 mm). Compounds were detected by UV at 260 nm. The mobile phase was MeCN/THF (80:20 v/v) with flow rate of 1 mL/min. The purity of all tested compounds was >98% based on analytical HPLC. 1H NMR spectra was recorded on Bruker AVANCE 600 DRX and/or 400 MHz, Bruker Top-Spin spectrometers in the solvents indicated. The Proton chemical shifts were reported in parts per million (δ ppm) relative to $(CH_3)_4Si$ and coupling constants (J) in Hertz (Hz) and s, d, t, m, br s, refer to singlet, doublet, triplet, multiplet, broad respectively.

Chemical Synthesis. The synthetic route of preparing exemplified compounds is shown in Schemes 1 and 2. A mixture of naphthalic anhydride and various amines in a molar ratio of 1:10 [such as aniline, dimethylaminopropylamine, dimethylethylene diamine or ethyl 4-aminobutyrate)] in toluene in the presence of acetic acid was heated at reflux. After completion of the reaction, the solvent was evaporated under reduced pressure to dryness. The solid residue was dissolved in ethyl acetate, washed with water, and dried over $Na_2SO_4$. The solvent was removed by evaporation in vacuo. The amino substituted derivatives were synthesized from the corresponding nitro substituted derivatives by catalytic hydrogenation (5% Pd/C, $H_2$) at 35 psi. The product was purified by recrystallization with EtOH or by column chromatography.

Compounds

N-Phenyl-1,8-naphthalimide (A1). Compound A1 was obtained from 1,8-naphthalic anhydride (1.2 g, 6 mmol) in aniline (50 ml) through general procedure to yield 1.16 g (70.7%), mp 218-220° C. (Lit[16] 202° C.) (Jaubert et al., *Berichte der deutschen chemischen Gesellschaft*. 1895;28(1):360-364), ESI-HRMS calcd for $C_{18}H_{11}NO_2$ m/z 296.0687 (M+Na), found 296.0692 (M+Na). $^1$H NMR (500 MHz, DMSO-$d_6$) 8.57 (t, J=7.16 Hz, 4H, naphthylic-H) 7.97 (t, J=7.69 Hz, 2H, naphthylic-H) 7.60 (t, J=7.13 Hz, 2H, benzene-H) 7.53 (t, J=7.66 Hz, 1H, benzene-H) 7.45 (d, J=7.27 Hz, 2H, benzene-H).

N-Phenyl-4-nitro-1,8-naphthalimide (A2). Compound A2 was obtained from 4-nitro-1,8-naphthalic anhydride (2.43 g, 10 mmol) in toluene (50 ml) and aniline (9.1 ml, 100 mmol) through general procedure to yield 2.775 g (92.7%), mp >280° C. (Lit[17] 280-282° C.) (Mitsuo et al., *Journal of Synthetic Organic Chemistry, Japan*. 1956;14(9):558-564), FAB-HRMS calcd for $C_{18}H_{10}N_2O_4$ m/z 319.0719 (M+H), found 319.0715 (M+H). $^1$H NMR (500 MHz, DMSO-$d_6$) 8.83 (d, J=8.55 Hz, 1H, naphthylic-H) 8.71 (d, J=7.27 Hz, 1H, naphthylic-H) 8.69 (d, J=8.04 Hz, 1H, naphthylic-H) 8.66 (d, J=7.42 Hz, 1H, naphthylic-H) 8.2 (t, J=7.43 Hz, 1H, naphthylic-H) 7.61 (t, J=7.23 Hz, 2H, benzene-H) 7.55 (t, J=6.89 Hz, 1H, benzene-H) 7.48 (d, J=7.27 Hz, 2H, benzene-H).

N-(3,4-Dichloro-phenyl)-4-nitro-1,8-naphthalimide (A3). Compound A3 was obtained from of 4-nitro-1,8-naphthalic anhydride (2.43 g, 10 mmol) and 3,4-dichloroaniline (16 g, 100 mmol) through general procedure to yield 3.3 g (85.2%), mp >280° C., FAB-HRMS calcd for $C_{18}H_8Cl_2N_2O_4$ m/z 386.9939 (M+H), found 386.993 (M+H). $^1$H NMR (500 MHz, DMSO-$d_6$) 8.79 (d, J=8.33 Hz, 1H, naphthylic-H) 8.67 (d, J=6.62 Hz, 1H, naphthylic-H) 8.64 (d, J=8.12 Hz, 1H, naphthylic-H) 8.6 (d, J=7.91 Hz, 1H, naphthylic-H) 8.15 (t, J=8.65 Hz, 1H, naphthylic-H) 7.86 (d, J=8.55 Hz, 1H, benzene-H) 7.83 (s, 1H, benzene-H) 7.5 (d, J=8.65 Hz, 1H, benzene-H).

N-(3-Methoxy-phenyl)-4-nitro-1,8-naphthalimide (A4). Compound A4 was obtained from 4-nitro-1,8-naphthalic anhydride (2.43 g, 10 mmol) and m-anisidine (11.2 ml, 100 mmol) through general procedure to yield 3.21 g (92.2%), mp >280° C., FAB-HRMS calcd for $C_{19}H_{12}N_2O_5$ m/z 349.0824 (M+H), found 349.0832 (M+H). $^1$H NMR (500 MHz, DMSO-$d_6$) 8.83 (d, J=8.76 Hz, 1H, naphthylic-H) 8.71 (d, J=7.27 Hz, 1H, naphthylic-H) 8.69 (d, J=7.48 Hz, 1H, naphthylic-H) 8.65 (d, J=7.48 Hz, 1H, naphthylic-H) 8.2 (t, J=8.16 Hz, 1H, naphthylic-H) 7.51 (t, J=8.01 Hz, 1H, benzene-H) 7.12 (m, 2H, benzene-H) 7.05 (d, J=8.15 Hz, 1H, benzene-H) 3.85 (s, 3H, OCH$_3$).

N-(4-Butyric acid-phenyl)-4-nitro-1,8-naphthalimide (A5). Compound A5 was obtained from 4-nitro-1,8-naphthalic anhydride (486.4 g, 2 mmol) and 4-(4-amino-phenyl) butyric acid (358.5 mg, 20 mmol) through general procedure to yield 877.5 mg (95.1%), mp 254.5-256° C., ESI-HRMS calcd for $C_{22}H_{12}N_2O_6$ m/z 427.0906 (M+Na), found 427.0898 (M+Na). $^1$H NMR (500 MHz, DMSO-$d_6$) 8.82 (d, J=8.41 Hz, 1H, naphthylic-H) 8.7 (d, J=7.27 Hz, 1H, naphthylic-H) 8.68 (d, J=8.14 Hz, 1H, naphthylic-H) 8.64 (d, J=7.76 Hz, 1H, naphthylic-H) 8.19 (t, J=8.03 Hz, 1H, naphthylic-H) 7.42 (d, J=8.03 Hz, 2H, benzene-H) 7.38 (d, J=8.41 Hz, 2H, benzene-H) 2.75 (t, J=7.84 Hz, 2H, C$\underline{H}_2$CH$_2$CH$_2$COOH) 2.35 (t, J=7.46 Hz, 2H, CH$_2$CH$_2$C$\underline{H}_2$COOH) 1.94 (quin, J=7.55 Hz, 2H, CH$_2$C$\underline{H}_2$CH$_2$COOH).

N-Phenyl-4-chloro-1,8-naphthalimide (A6). Compound A6 was obtained from 4-chloro-1,8-naphthalic anhydride (465 mg, 2 mmol) and aniline (1.8 ml, 20 mmol) through general procedure to yield 137.9 mg (22.4%), mp 263-265.5° C. (Lit[18] 231-233° C.) (Takaaki et al., Fungicidal Compositions; 1973), FAB-HRMS calcd for $C_{18}H_{10}ClNO_2$ m/z 308.0478 (M+H), found 308.048 (M+H). 1H NMR (500 MHz, DMSO-$d_6$) 8.75 (d, J=7.7 Hz, 1H, naphthylic-H) 8.67 (d, J=6.6 Hz, 1H, naphthylic-H) 8.52 (d, J=7.9 Hz, 1H, naphthylic-H) 8.16 (d, J=7.9 Hz, 1H, naphthylic-H) 8.12 (t, J=7.5 Hz, 1H, naphthylic-H) 7.60 (t, J=7.18 Hz, 2H, benzene-H) 7.53 (t, J=6.89 Hz, 2H, benzene-H) 7.46 (d, J=7.46 Hz, 2H, benzene-H).

N-(3-Methoxy-phenyl)-4-chloro-1,8-naphthalimide (A7). Compound A7 was obtained from 4-chloro-1,8-naphthalic anhydride (465 mg, 2 mmol) and m-anisidine (2.3 ml, 20 mmol) through general procedure to yield 250 mg (37%), mp >280° C., FAB-HRMS calcd for $C_{19}H_{12}ClNO_3$ m/z 338.0584 (M+H), found 338.0576 (M+H). $^1$H NMR (500 MHz, DMSO-$d_6$) 8.67 (d, J=8.72 Hz, 1H, naphthylic-H) 8.6 (d, J=6.47 Hz, 1H, naphthylic-H) 8.45 (d, J=7.9 Hz, 1H, naphthylic-H) 8.08 (d, J=7.9 Hz, 1H, naphthylic-H) 8.05 (t, J=8.71 Hz, 1H, naphthylic-H) 7.43 (t, J=8.01 Hz, 1H, benzene-H) 7.04 (d, J=8.09 Hz, 1H, benzene-H) 7.02 (s, J=7.46 Hz, 1H, benzene-H) 6.96 (d, J=8.72 Hz, 1H, benzene-H) 3.78 (s, 3H, OCH$_3$).

N-(3-Trifluoromethyl-phenyl)-4-chloro-1,8-naphthalimide (A8). Compound A8 was obtained from 4-chloro-1,8-naphthalic anhydride (465 mg, 2 mmol) and 3-aminobenzotrifluoride (2.5 ml, 20 mmol) through general procedure to yield 130.2 mg (17.3%), mp 278-279° C., FAB-HRMS calcd for $C_{19}H_9ClF_3NO_2$ m/z 376.0352 (M+H), found 376.0345 (M+H). $^1$H NMR (500 MHz, DMSO-$d_6$) 8.7 (d, J=8.5 Hz, 1H, naphthylic-H) 8.62 (d, J=6.61 Hz, 1H, naphthylic-H) 8.47 (d, J=7.9 Hz, 1H, naphthylic-H) 8.11 (d, J=7.9 Hz, 1H, naphthylic-H) 8.07 (t, J=7.8 Hz, 1H, naphthylic-H) 7.9 (s, 1H, benzene-H) 7.87 (d, J=7.7 Hz, 1H, benzene-H) 7.8 (d, J=7.78 Hz, 1H, benzene-H) 7.77 (t, J=5.83 Hz, 1H, benzene-H).

N-(3-Bromo-phenyl)-4-chloro-1,8-naphthalimide (A9). Compound A9 was obtained from 4-chloro-1,8-naphthalic anhydride (465 mg, 2 mmol) and 3-bromoaniline (2.2 ml, 20 mmol) through general procedure to yield 102.2 mg (13.2%), mp >280° C., FAB-HRMS calcd for $C_{18}H_9BrClNO_2$ m/z 385.9583 (M+H), found 385.9577 (M+H). $^1$H NMR (500 MHz, DMSO-$d_6$) 8.7 (d, J=8.33 Hz, 1H, naphthylic-H) 8.61 (d, J=7.27 Hz, 1H, naphthylic-H) 8.46 (d, J=7.91 Hz, 1H, naphthylic-H) 8.1 (d, J=7.91 Hz, 1H, naphthylic-H) 8.07 (t, J=7.91 Hz, 1H, naphthylic-H) 7.72 (br s, 1H, benzene-H) 7.7 (d, J=8.12 Hz, 1H, benzene-H) 7.51 (t, J=7.8 Hz, 1H, benzene-H) 7.46 (d, J=7.09 Hz, 1H, benzene-H).

N-(3-Chloro-phenyl)-4-chloro-1,8-naphthalimide (A10). Compound A10 was obtained from 4-chloro-1,8-naphthalic anhydride (465 mg, 2 mmol) and 3-chloroaniline (2.13 ml, 20 mmol) through general procedure to yield 82.8 mg (12.1%), mp 273-275° C., FAB-HRMS calcd for $C_{18}H_9Cl_2NO_2$ m/z 342.0089 (M+H), found 342.0098 (M+H). $^1$H NMR (500 MHz, DMSO-$d_6$) 8.7 (d, J=8.55 Hz, 1H, naphthylic-H) 8.62 (d, J=7.27 Hz, 1H, naphthylic-H) 8.47 (d, J=7.91 Hz, 1H, naphthylic-H) 8.1 (d, J=7.91 Hz, 1H, naphthylic-H) 8.07 (t, J=7.91 Hz, 1H, naphthylic-H) 7.58 (m, 3H, benzene-H) 7.41 (d, J=5.94 Hz, 1H, benzene-H). Papenfuhs et al., United Kindom: Hoechst Aktiengesellschaft (Frankfurt am Main, DE); 1977.

N-(3-Bromo-4-fluoro-phenyl)-4-chloro-1,8-naphthalimide (A11). Compound A11 was obtained from 4-chloro-1,8-naphthalic anhydride (465 mg, 2 mmol) and 3-bromo-4-fluoroaniline (3.8 g, 20 mmol) through general procedure to yield 398 mg (49.2%), mp >280° C., FAB-HRMS calcd for $C_{18}H_8BrClFNO_2$ m/z 403.9489 (M+H), found 403.949 (M+H). $^1$H NMR (500 MHz, DMSO-$d_6$) 8.69 (d, J=8.76 Hz, 1H, naphthylic-H) 8.61 (d, J=7.29 Hz, 1H, naphthylic-H) 8.46 (d, J=7.91 Hz, 1H, naphthylic-H) 8.1 (d, J=7.91 Hz, 1H, naphthylic-H) 8.07 (t, J=7.65 Hz, 1H, naphthylic-H) 7.87 (dd, J=6.3, 2.24 Hz, 1H, benzene-H) 7.54 (m, 2H, benzene-H)

N-(4-Fluoro-phenyl)-4-chloro-1,8-naphthalimide (A12). Compound A12 was obtained from 4-chloro-1,8-naphthalic anhydride (465 mg, 2 mmol) and 4-fluoroaniline (1.9 ml, 20 mmol) through general procedure to yield 264 mg (40.5%), mp 274-276° C., FAB-HRMS calcd for $C_{18}H_9ClFNO_2$ m/z 326.0384 (M+H), found 326.0391 (M+H). $^1$H NMR (500 MHz, DMSO-$d_6$) 8.69 (d, J=8.56 Hz, 1H, naphthylic-H) 8.61 (d, J=7.34 Hz, 1H, naphthylic-H) 8.46 (d, J=7.91 Hz, 1H, naphthylic-H) 8.1 (d, J=7.91 Hz, 1H, naphthylic-H) 8.06 (t, J=8.79 Hz, 1H, naphthylic-H) 7.46 (m, 2H, benzene-H) 7.37 (m, 2H, benzene-H)

N-(4-Bromo-phenyl)-4-chloro-1,8-naphthalimide (A13). Compound A13 was obtained from 4-chloro-1,8-naphthalic anhydride (465 mg, 2 mmol) and 4-bromoaniline (3.4 g, 20 mmol) through general procedure to yield 513 mg (66.3%), mp >280° C., FAB-HRMS calcd for $C_{18}H_9BrClNO_2$ m/z 385.9583 (M+H), found 385.9587 (M+H). $^1$H NMR (500 MHz, DMSO-$d_6$) 8.69 (d, J=7.38 Hz, 1H, naphthylic-H) 8.61 (d, J=7.95 Hz, 1H, naphthylic-H) 8.46 (d, J=7.91 Hz, 1H, naphthylic-H) 8.1 (d, J=7.91 Hz, 1H, naphthylic-H) 8.06 (t, J=8.42 Hz, 1H, naphthylic-H) 7.74 (d, J=8.52 Hz, 2H, benzene-H) 7.39 (d, J=8.51 Hz, 2H, benzene-H)[19]

N-(3,4-Dichloro-phenyl)-4-chloro-1,8-naphthalimide (A14). Compound A14 was obtained from 4-chloro-1,8-naphthalic anhydride (465 mg, 2 mmol) and 3,4-dichloroaniline (3.24 g, 20 mmol) through general procedure to yield 123 mg (15.9%), mp >280° C. (Lit[18] >300° C.), FAB-HRMS calcd for $C_{18}H_8Cl_3NO_2$ m/z 375.9699 (M+H), found 375.9697 (M+H). $^1$H NMR (500 MHz, DMSO-$d_6$) 8.7 (d, J=8.33 Hz, 1H, naphthylic-H) 8.62 (d, J=6.62 Hz, 1H, naphthylic-H) 8.47 (d, J=7.91 Hz, 1H, naphthylic-H) 8.11 (d, J=7.91 Hz, 1H, naphthylic-H) 8.07 (t, J=7.91 Hz, 1H, naphthylic-H) 7.85 (s, 1H, benzene-H) 7.82 (m, 1H, benzene-H) 7.48 (d, J=8.12 Hz, 1H, benzene-H).

N-(2-Dimethylamino-ethyl)-1,8-naphthalimide hydrochloride (B1). Compound B1 was obtained from 1,8-naphthalic anhydride (1 g, 5.05 mmol) and N,N-dimethylethylene diamine (5.5 ml, 50 mmol) through general procedure and form water soluble salt with 1.75 M HCl/EtOAc (2.9 ml, 5.1 mmol) to yield 1.3 g (84.5%), mp >280° C. (Lit[20] 296-298° C.), ESI-HRMS calcd for $C_{16}H_{17}ClN_2O_2$ m/z 303.09 (M−H), found 303.0906 (M−H). $^1$H NMR (500 MHz, Methanol-d4) 9.61 (br s, 1H, HCl) 8.53 (d, J=7.13, 2H, naphthylic-H) 8.51 (d, J=7.47 Hz, 2H, naphthylic-H) 7.91 (t, J=7.47 Hz, 2H, naphthylic-H) 4.41 (t, J=5.98 Hz, 2H, ethylene-$CH_2$) 3.45 (t, J=5.98 Hz, 2H, ethylene-$CH_2$) 3.03 (s, 6H, N($CH_3$)$_2$).

N-(2-Dimethylamino-ethyl)-4-nitro-1,8-naphthalimide (B2). Compound B2 was obtained from 4-nitro-1,8-naphthalic anhydride (1 g, 4.11 mmol) and N,N-dimethylethylene diamine (4.37 ml, 40 mmol) through general procedure to yield 843.6 mg (65.7%), mp 131-133° C. (Lit[20] 106-109° C.), ESI-HRMS calcd for $C_{16}H_{15}N_3O_4$ m/z 314.1141 (M+H), found 314.1148 (M+H). $^1$H NMR (500 MHz, DMSO-$d_6$) 8.72 (d, J=8.55 Hz, 1H, naphthylic-H) 8.64 (d, J=7.27 Hz, 1H, naphthylic-H) 8.62 (d, J=8.12 Hz, 1H, naphthylic-H) 8.56 (d, J=8.12 Hz, 1H, naphthylic-H) 8.1 (t, J=8.01 Hz, 1H, naphthylic-H) 4.16 (t, J=6.95 Hz, 2H, ethylene-$CH_2$) 2.53 (m, 2H, ethylene-$CH_2$) 2.38 (s, 6H, N($CH_3$)$_2$).

N-(3-Dimethylamino-propyl)-4-nitro-1,8-naphthalimide (B3). Compound B3 was obtained from 4-nitro-1,8-naphthalic anhydride (1 g, 4.11 mmol) and 3-dimethylaminopropylamine (4.4 ml, 40 mmol) through general procedure to yield 564 mg (42.0%), mp 108-110° C. (Lit[21] 106-109° C.), ESI-HRMS calcd for $C_{17}H_{17}N_3O_4$ m/z 328.1297 (M+H), found 328.1299 (M+H). $^1$H NMR (500 MHz, DMSO-$d_6$) 8.71 (d, J=8.55 Hz, 1H, naphthylic-H) 8.64 (d, J=7.27 Hz, 1H, naphthylic-H) 8.61 (d, J=7.91 Hz, 1H, naphthylic-H) 8.55 (d, J=7.91 Hz, 1H, naphthylic-H) 8.1 (t, J=7.91 Hz, 1H, naphthylic-H) 4.08 (t, J=7.25 Hz, 2H, propylene-$CH_2$) 2.31 (t, J=6.95 Hz, 2H, propylene-$CH_2$) 2.12 (s, 6H, N($CH_3$)$_2$) 1.78 (quin, J=7.27 Hz, 2H, propylene-$CH_2$).

N-(2-dimethylamino-ethyl)-4-chloro-1,8-naphthalimide hydrochloride (B4) Compound B4 was obtained from 4-chloro-1,8-naphthalic anhydride (1 g, 4.3 mmol) and N,N-dimethylethylene diamine (4.37 ml, 40 mmol) through general procedure and form water soluble salt with 1.75 M HCl/EtOAc (2.6 ml, 4.5 mmol) to yield 1.16 g (81.5%), mp >280° C. (Lit[22] 293-295° C.), ESI-HRMS calcd for $C_{16}H_{16}Cl_2N_2O_2$ m/z 332.1166 (M−H), found 332.1157 (M−H). $^1$H NMR (500 MHz, DMSO-$d_6$) 9.76 (br s, 1H, HCl) 8.66 (d, J=8.55 Hz, 1H, naphthylic-H) 8.62 (d, J=7.27 Hz, 1H, naphthylic-H) 8.47 (d, J=7.91 Hz, 1H, naphthylic-H) 8.09 (d, J=7.91 Hz, 1H, naphthylic-H) 8.05 (t, J=7.52 Hz, 1H, naphthylic-H) 4.4 (t, J=5.98 Hz, 2H, ethylene-$CH_2$) 3.44 (t, J=5.88 Hz, 2H, ethylene-$CH_2$) 2.88 (s, 6H, N($CH_3$)$_2$).

N-Ethyl-1,8-naphthalimide (C1). Compound C1 was obtained from 1,8-naphthalic anhydride (396.4 mg, 2 mmol) and ethylamine (12.9, 20 mmol) through general procedure to yield 168 mg (37.3%), mp 171-172.5° C. (Lit[18] 158° C.), FAB-HRMS calcd for $C_{14}H_{11}NO_2$ m/z 226.0868 (M+H), found 226.0868 (M+H). $^1$H NMR (500 MHz, DMSO-$d_6$) 8.57 (d, J=7.99 Hz, 2H, naphthylic-H) 8.53 (d, J=8.67 Hz, 2H, naphthylic-H) 7.94 (t, J=7.69 Hz, 2H, naphthylic-H) 4.16 (q, J=7.05 Hz, 2H, C$\underline{H}_2$CH$_3$) 1.28 (t, J=7.05 Hz, 3H, CH$_2$C$\underline{H}_3$).

N-Methyl-4-nitro-1,8-naphthalimide (C2). Compound C2 was obtained from 4-nitro-1,8-naphthalic anhydride (2.43 g, 10 mmol) and methylamine (77 g, 100 mmol) through general procedure to yield 1.31 g (51.1%), mp 209-212.5° C. (Lit[18] 208-209° C.), FAB-HRMS calcd for $C_{13}H_8N_2O_4$ m/z 257.0562 (M+H), found 257.0563 (M+H). $^1$H NMR (500 MHz, DMSO-$d_6$) 8.7 (d, J=8.22 Hz, 1H, naphthylic-H) 8.62 (m, 2H, naphthylic-H) 8.56 (m, 1H, naphthylic-H) 8.09 (t, J=8.22 Hz, 1H, naphthylic-H) 3.41 (s, 3H, CH$_3$).

N-Ethyl-4-nitro-1,8-naphthalimide (C3). Compound C3 was obtained from 4-nitro-1,8-naphthalic anhydride (2.43 g, 10 mmol) and ethylamine (64.4 g, 40 mmol) through general procedure to yield 922.6 mg (34.1%), mp 191-192.5° C. (Lit[18] 187.5-188.5° C.), FAB-HRMS calcd for $C_{14}H_{10}N_2O_4$ m/z 271.0719 (M+H), found 271.0722 (M+H). $^1$H NMR (500 MHz, DMSO-$d_6$) 8.71 (d, J=9.0 Hz, 1H, naphthylic-H) 8.63 (m, 2H, naphthylic-H) 8.56 (m, 1H, naphthylic-H) 8.09 (t, J=7.63 Hz, 1H, naphthylic-H) 4.09 (q, J=7.04 Hz, 2H, C$\underline{H}_2$CH$_3$) 1.24 (t, J=7.04 Hz, 3H, CH$_2$C$\underline{H}_3$).

N-Methyl-4-chloro-1,8-naphthalimide (C4). Compound C4 was obtained from 4-chloro-1,8-naphthalic anhydride (465 mg, 2 mmol) and methylamine (15.5g, 200 mmol) through general procedure to yield 160 mg (32.6%), mp 186-188° C. (Lit[18] 171-173° C.) (Takaaki et al., Fungicidal Compositions; 1973), FAB-HRMS calcd for $C_{13}H_8ClNO_2$ m/z 246.032 (M+H), found 246.0318 (M+H). $^1$H NMR (500 MHz, DMSO-$d_6$) 8.62 (d, J=8.69 Hz, 1H, naphthylic-H) 8.60 (d, J=7.48 Hz, 1H, naphthylic-H) 8.45 (d, J=7.69 Hz, 1H, naphthylic-H) 8.06 (d, J=7.91 Hz, 1H, naphthylic-H) 8.02 (t, J=7.91 Hz, 1H, naphthylic-H) 3.4 (s, 3H, CH$_3$).

N-Ethyl-4-chloro-1,8-naphthalimide (C5). Compound C5 was obtained from 4-chloro-1,8-naphthalic anhydride (465 mg, 2 mmol) and ethylamine (12.9 g, 200 mmol) through general procedure to yield 170 mg (32.7%), mp 167-170° C. (Lit[18] 165-166° C.) (Takaaki et al., Fungicidal Compositions; 1973), FAB-HRMS calcd for $C_{14}H_{10}ClNO_2$ m/z 260.0478 (M+H), found 260.0484 (M+H). $^1$H NMR (500 MHz, DMSO-$d_6$) 8.61 (t, J=7.91 Hz, 2H, naphthylic-H) 8.45 (d, J=7.91 Hz, 1H, naphthylic-H) 8.05 (d, J=7.91 Hz, 1H, naphthylic-H) 8.02 (t, J=7.49 Hz, 1H, naphthylic-H) 4.08 (q, J=7.05 Hz, 2H, C$\underline{H}_2$CH$_3$) 1.22 (t, J=7.05 Hz, 3H, CH$_2$C$\underline{H}_3$).

N-(Butyric acid ethyl ester)-4-nitro-1,8-naphthalimide (D1). Compound D1 was obtained from ethyl 4-aminobutyrate hydrochloride (8.4 g, 50 mmol) and 4-nitro-1,8-naphthalic anhydride (1.22 g, 5 mmol) through general procedure to yield 1.65 g (97.0%), mp 115-116° C., FAB-HRMS calcd for $C_{18}H_{16}N_2O_6$ m/z 357.1087 (M+H), found 357.1091 (M+H). $^1$H NMR (500 MHz, DMSO-$d_6$) 8.72 (d, J=8.55 Hz, 1H, naphthylic-H) 8.64 (d, J=7.27 Hz, 1H, naphthylic-H) 8.62 (d, J=8.12 Hz, 1H, naphthylic-H) 8.56 (d, J=7.91 Hz, 1H, naphthylic-H) 8.1 (t, J=8.01 Hz, 1H, naphthylic-H) 4.11 (t, J=6.84 Hz, 2H, CH$_2$CH$_2$CH$_2$COOCH$_2$CH$_3$) 3.97 (q, J=7.05 Hz, 2H, CH$_2$CH$_2$CH$_2$COOCH$_2$CH$_3$) 2.41 (t, J=7.37 Hz, 2H, CH$_2$CH$_2$CH$_2$COOCH$_2$CH$_3$) 1.94 (quin, J=7.11 Hz, 2H, CH$_2$CH$_2$CH$_2$COOCH$_2$CH$_3$) 1.12 (t, J=7.05 Hz, 3H, CH$_2$CH$_2$CH$_2$COOCH$_2$CH$_3$)

N-Phenyl-4-amino-1,8-naphthalimide (E1). Compound E1 was obtained from N-phenyl-4-nitro-naphthalimide (1.27 g, 4 mmol) through general procedure to yield 583 mg (56.4%), mp 276-278° C. (Lit[23] 302-304° C.) (Mitsuo et al., *Journal of Synthetic Organic Chemistry, Japan*. 1956;14(8): 504-508), ESI-HRMS calcd for $C_{18}H_{12}N_2O_2$ m/z 287.0821 (M–H), found 287.0816 (M–H). $^1$H NMR (500 MHz, DMSO-$d_6$) 8.66 (d, J=7.69 Hz, 1H, naphthylic-H) 8.43 (d, J=6.62 Hz, 1H, naphthylic-H) 8.19 (d, J=8.33 Hz, 1H, naphthylic-H) 7.69 (t, J=8.58 Hz, 1H, naphthylic-H) 7.5 (m, 4H, benzene-H, amino-H) 7.43 (t, J=7.8 Hz, 1H, benzene-H) 7.3 (d, J=6.95 Hz, 2H, benzene-H) 6.88 (d, J=8.33 Hz, 1H, naphthylic-H).

N-(2-dimethylamino-ethyl)-4-amino-1,8-naphthalimide hydrochloride (E2). Compound E2 was obtained from N-(2-dimethylamino-ethyl)-4-nitro-1,8-naphthalimide (200 mg, 0.64 mmol) through general procedure and form water soluble salt with 1.75 M HCl/EtOAc (0.37 ml, 0.65 mmol) to yield 174.2 mg (77.3%), mp >280° C. (Lit[20] 184-185° C.) (Norton et al., *Anticancer Drugs*. 2008;19(1):23-36), ESI-HRMS calcd for $C_{16}H_{18}ClN_3O_2$ m/z 318.1009 (M–H), found 318.1003 (M–H). $^1$H NMR (500 MHz, DMSO-$d_6$) 9.3 (br s, 1H, HCl) 8.66 (d, J=8.72 Hz, 1H, naphthylic-H) 8.46 (d, J=6.79 Hz, 1H, naphthylic-H) 8.22 (d, J=8.55 Hz, 1H, naphthylic-H) 7.68 (t, J=8.73 Hz, 1H, naphthylic-H) 7.56 (br s, 2H, exchangeable, amino-H) 6.87 (d, J=8.33 Hz, 1H, naphthylic-H) 4.35 (t, J=5.88 Hz, 2H, ethylene-CH$_2$) 3.42 (in H$_2$O, show in methanol-d4, ethylene-CH$_2$) 2.89 (br s, 6H, N(CH$_3$)$_2$). Norton et al., *Anticancer Drugs*. 2008;19(1): 23-36.

N-(3-dimethylamino-propyl)-4-amino-1,8-naphthalimide hydrochloride (E3). Compound E3 was obtained from N-(3-dimethylamino-propyl)-4-nitro-naphthalimide (250 mg, 0.76 mmol) through general procedure and form water soluble salt with 1.75 M HCl/EtOAc (0.45 ml, 0.8 mmol), to yield 120 mg (42.8%), mp >280° C. (Lit[21] 184-185° C.) (Stevenson et al., *J Med Chem*. 1984;27(12):1677-1682), ESI-HRMS calcd for $C_{17}H_{20}ClN_3O_2$ m/z 303.09 (M–Cl), found 303.0903 (M–Cl). $^1$H NMR (500 MHz, DMSO-$d_6$) 9.75 (br s, 1H, HCl) 8.65 (d, J=8.79 Hz, 1H, naphthylic-H) 8.44 (d, J=8.79 Hz, 1H, naphthylic-H) 8.21 (d, J=8.33 Hz, 1H, naphthylic-H) 7.67 (t, J=8.79 Hz, 1H, naphthylic-H) 7.51 (br s, 2H, exchangeable, amino-H) 6.86 (d, J=8.55 Hz, 1H, naphthylic-H) 4.08 (t, J=6.62 Hz, 2H, propylene-CH$_2$) 3.11 (t, J=7.82 Hz, 2H, propylene-CH$_2$) 2.73 (s, 6H, N(CH$_3$)$_2$) 2.02 (m, 2H, propylene-CH$_2$).

The primary erythroid cell culture. The peripheral blood samples were purchased from the Taipei Blood Center. The concentrated blood was diluted 1:5 (V/V) with PBS and gentle layer on Ficoll-Hypaque (d=1.007 g/ml) (Ge-Healthcare). After centrifugation at 400 g for 20 minutes, the cells in the inter-phase region were collected. The collected cells were washed with PBS and centrifuged at low speed for three times. The remained mononuclear cells were expanded in Phase I medium containing 1× SFEM (StemSpan), 100 ng/ml SCF, 20 ng/ml IL-3, 20 ng/ml IL-6, and 100 ng/ml Flt3-L at 37° C. incubator with 5% CO$_2$ for 7 days. The expanded mononuclear cells were then differentiated in Phase II medium which contains 1× SFEM (StemSpan), 20 ng/ml SCF, 5 ng/ml IL-3, 1 U/ml EPO for another 7 days. The resulted differentiated erythroid cells were treated with indicated compounds of different dosages with the seeding density of 5×10$^5$ cells/ml for another 3 days.

Quantitative RT-PCR. After 3 days of drug-treatment, the total RNA was extracted by RNA Spin mini kit (Ge-Healthcare) and reverse-transcription was performed by using superscript II (Invitrogen) followed the manufactors instruction. Quantitative PCR was performed on LightCycler with using STBR green master mix followed the manufactors instruction (Roche). The absolute quantitative RT-PCR was calculated by the standard curve with supplying a known copy number of plasmids. The relative quantitative RT-PCR was normalized to the expression levels of the β-actin and compared to the mock control.

Cell viability assay. The cell viability was detected by using AlamarBlue reagent (Invitrogen). After 3 days, the drug-tested cells were transferred into 96-well plate, added with 1/10 volume of AlamarBlue reagent, and then incubate at 37° C. overnight. The cell viability was calculated by a fluorescence reader (Ex 530-560 nm, Em 590 nm).

Western blot analysis. After 3 days of compound treatment, total protein or histone of the drug-treated cells was extracted. Histone was extracted by histone extraction buffer (10 mM HEPES, 1.5 mM MgCl$_2$, mM KCl, 0.5 mM DTT, 1.5 mM PMSF and 0.2 N HCl) at 4° C. overnight then centrifuged at 13,000 rpm for 5 minutes and collected the supernatant. Thirty microgram of histone extracts were separated in 15% SDS-PAGE and blotted onto PVDF membrane. After blocking with 5% non-fat milk in TBST, the membrane was then incubated with primary antibody against total histone H4 or total acetyl histone H4 at 4° C. overnight. Total protein was extracted by modified RIPA (50 mM Tris-HCl pH7.8, 150 mM NaCl, 1% NP-40, 0.5% sodium deoxycholate, 0.1% SDS, 1 mM EGTA, 5 mM EDTA, 10 mM NaF, 1 mM NaV$_3$O$_4$ and 1× complete, EDTA-free Protease Inhibitor Cocktail). Thirty microgram of total protein extracts were separate by 10% SDS-PAGE and blotted onto PVDF membrane. After blocking with 5% non-fat milk in TBST, the membrane was incubated with primary antibody against BCL11A, p38, p-p38, γ-globin or β-actin at 4° C. overnight. After incubating with horseradish peroxidase-conjugated secondary antibodies and washing the blot, the signals of indicated proteins were visualized by using ECL (PerKinElmer) following the manufactor's protocol.

Statistical analysis. The data are presented as the mean plus or minus standard error of the mean (SEM) for at least 3 experiments. Statistical analysis of the raw data was performed by the 2-tailed t test. The Student t test was used to measure differences in samples. A probability of less than 0.05 (P<0.05) was considered significant. (*: P<0.05, : P<0.01, *: P<0.001)

Results

N-substituted 1,8-naphthalimide Derivatives are Potential HbF-inducing Agents.

Figure 2:
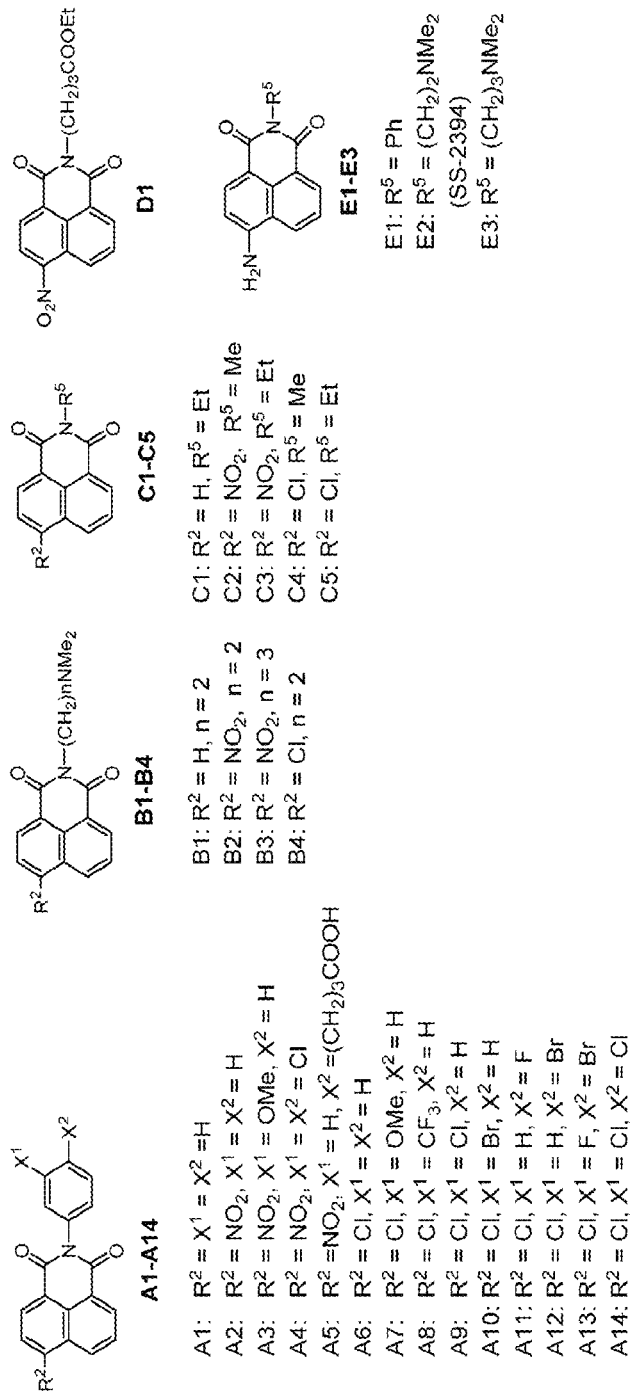
FIG. 2 shows the structures of five subgroups of N-substituted 1,8-naphthalimide derivatives. The naphthalimide derivatives were prepared by the condensation of naphthalic anhydride derivatives with substituted aniline (A1-A14), dimethylaminopropylamine/dimethylethylene diamine (B1-B4), alkly amine (C1-C5), or ethyl 4-aminobutyrate (D1). The amino-substituted naphthalimide derivatives (E1-E3) were prepared by the reduction of the nitro-substituted naphthalimide compounds A2, B2, and B3 by catalytic hydrogenation.
Figure 3:
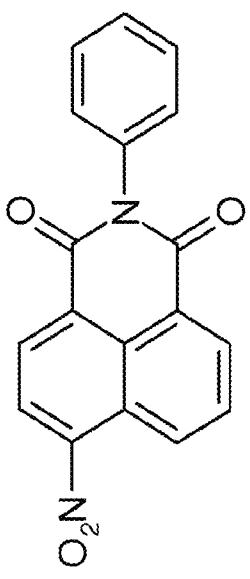
FIG. 3 is graph showing the dosage effects of six naphthalimide derivatives in mediating the γ globin gene induction and cell proliferation in primary human erythroid cells. Six naphthalimide derivatives with identical pharmacophore were selected to estimate their γ globin gene inducing abilities in primary human erythroid cells. After 3 days of compounds treatment, the total mRNA was extracted and the relative induction fold of the γ globin gene was analyzed by quantitative RT-PCR. The cell proliferation rate was examined by AlamarBlue reagent. Data are presented as the relative expression level in mean±SEM, N=8.
Figure 3:
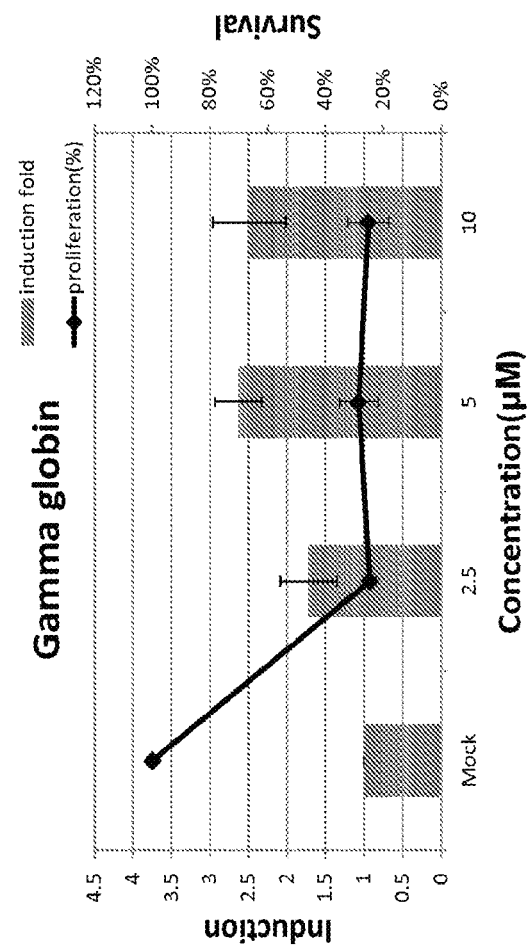
Figure 3:
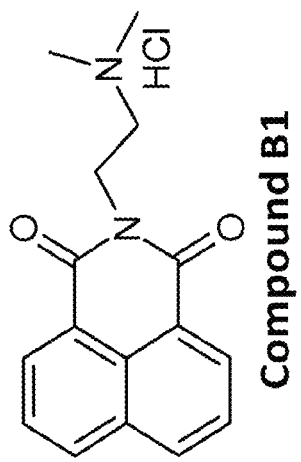
Figure 3:
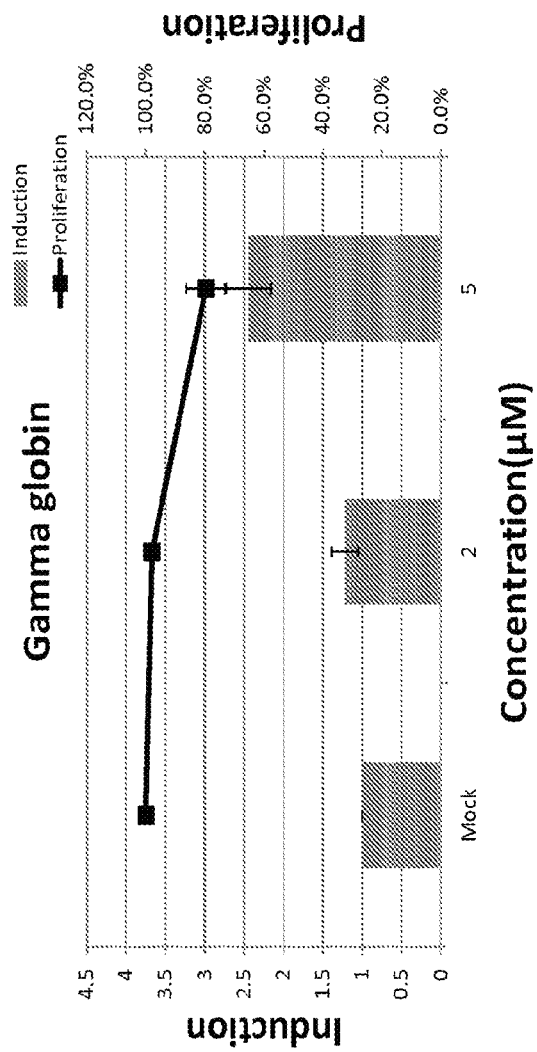
Figure 3:
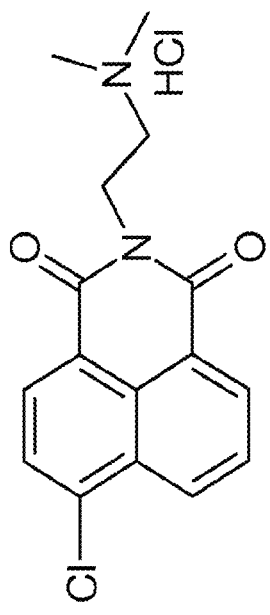
Figure 3:
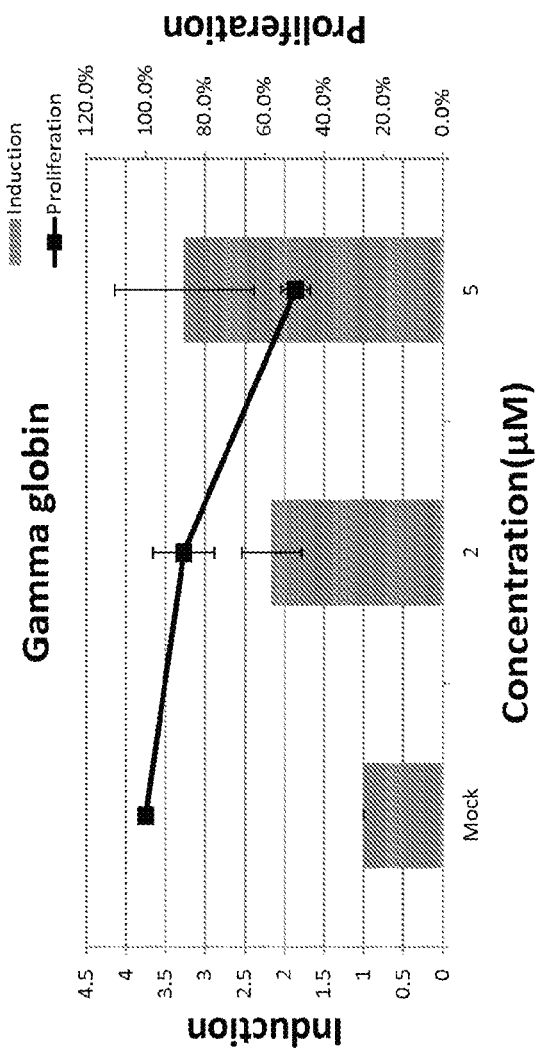
Figure 3:
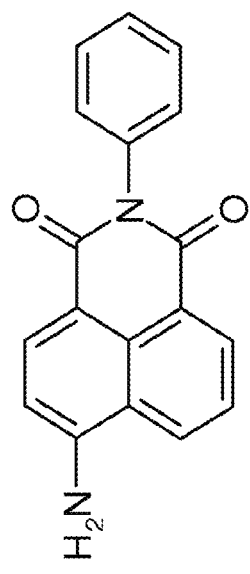
Figure 3:
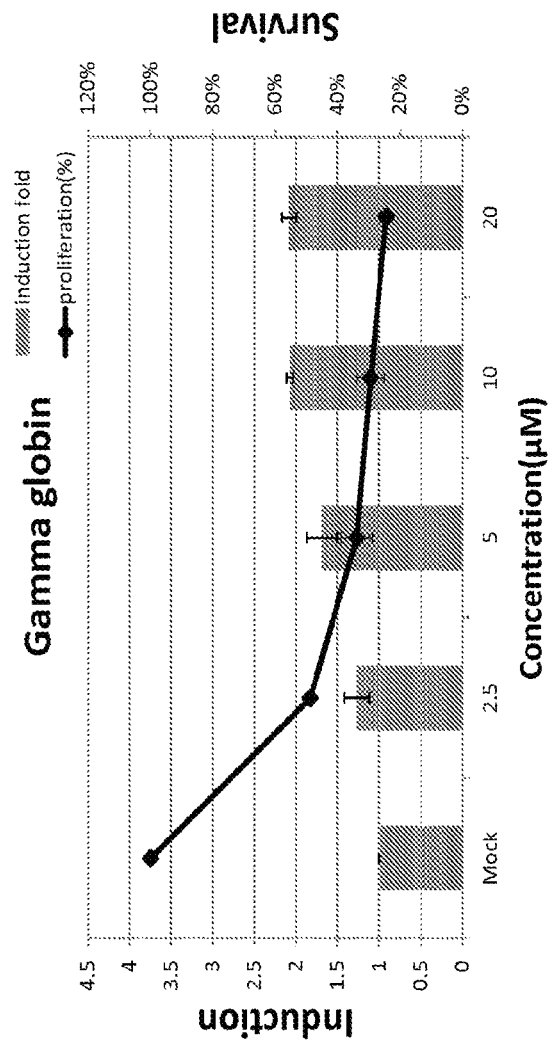
Figure 3:
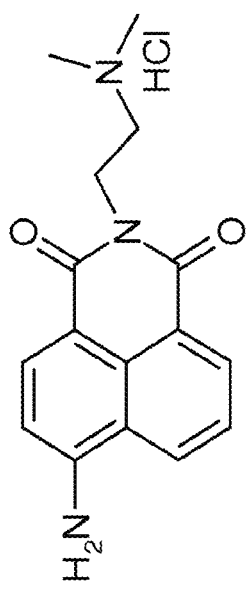
Figure 3:
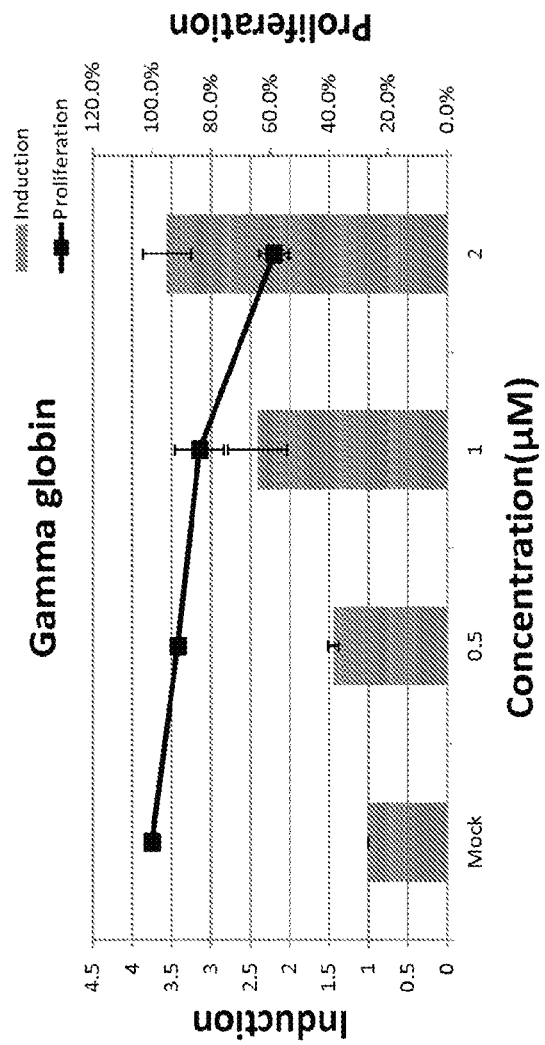
Figure 3:
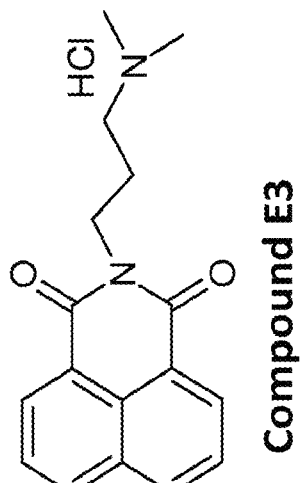
Figure 3:
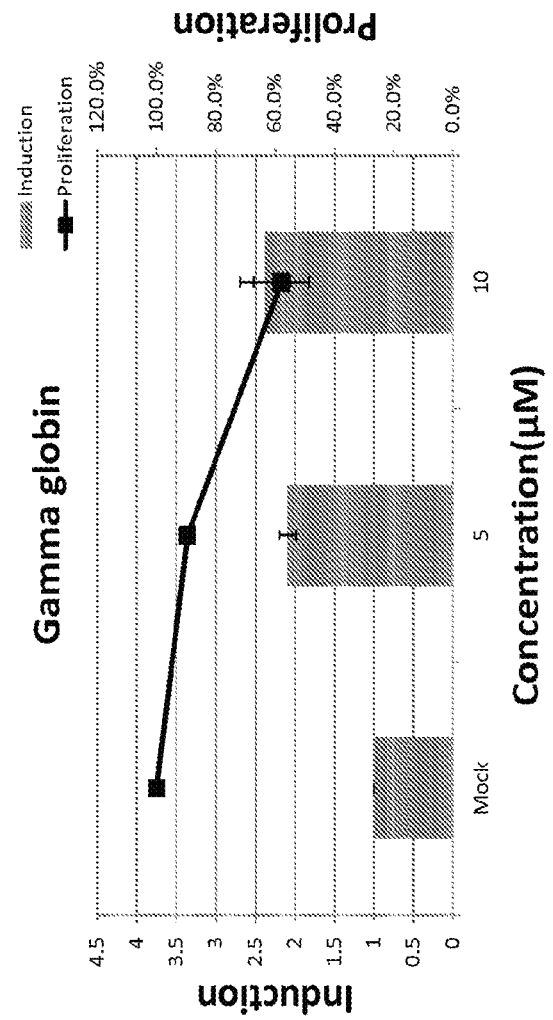

To search for new agents, which are capable of inducing the expression of γ globin, a series of naphthalimide derivatives with various substituent(s) on the naphthalene ring and the heterocyclic N-atom (A1-A14, B1-B4, C1-05, D1, and E1-E3, FIG. 2) were synthesized. These derivatives were subjected to evaluating the γ globin induction abilities in differentiated peripheral blood mononuclear cells (PBMCs). The PBMCs isolated from the peripheral blood of donors were expanded and differentiated for a total of 14 days in a two-phase liquid culture. The resulted primary erythoid cells were then treated with different dosages of naphthalimide derivatives individually for another 3 days. The expression levels of the endogenous γ globin gene were estimated by relative quantitative RT-PCR and the proliferation rates of these cells were examined by AlamarBlue cell viability assay. Among these naphthalimide derivatives, compounds A2, B1, B4, E1, E2, and E3 were found to have potent γ globin-inducing effect; 2-4.5-folds induction of the γ globin gene expression in the compounds-treated cells (FIG. 3).

The proliferation rates of these cells displayed reverse relationships with the concentrations of these compounds. To compare the HbF-inducing capability of these compounds, the induction folds of γ globin gene at concentrations of their $IC_{50}$ (the half maximal inhibitory concentration) were examined. The $IC_{50}$ values indicate that the concentrations of the individual compound at which the cell (primary human erythroid cells) proliferation rate is reduced by 50%. As shown in Table 3, compounds B1, B4, E2, and E3 significantly elevated the expression levels of γ globin mRNA up to 4.1-, 3.3-, 4.0-, and 2.7-folds at concentrations of their $IC_{50}$, respectively (Table 3), While, compounds A2 and E1 displayed only minor γ globin-inducing potentials with only 1.1- and 1.3-folds of the γ globin gene induction at concentrations of their $IC_{50}$, respectively.

TABLE 3

Comparison of $IC_{50}$, solubility, and γ globin gene inducing abilities of γ globin-inducing compounds.

| Compound ID | DMSO | $H_2O$ | $IC_{50}$ (μM) | EC (μM) induction of HU $IC_{50}$ (2.3 fold) | $IC_{50}$/ EC | γ globin induction ($IC_{50}$) |
|---|---|---|---|---|---|---|
| S51021 | 10 mM | | 21.8 | 2.3 | 9.5 | 2.97 |
| A1 | 10 mM | | | 2.3 | 7.8 | 0.3 | 1.3 |
| B1 | | >100 mM | 10.7 | 4.7 | 2.3 | 4.1 |
| B4 | | >100 mM | 5.0 | 2.2 | 2.3 | 3.3 |
| E1 | 10 mM | | 0.3 | 2.9 | 0.1 | 1.1 |
| E2 (SS-2394) | | >100 mM | 2.3 | 0.8 | 2.9 | 4.0 |
| E3 | | >100 mM | 11.2 | 7.4 | 1.5 | 2.7 |
| HU | | >100 mM | 145.9 | 145.9 | 1 | 2.3 |
| NaB | | >100 mM | 221.6 | ND | ND | 1.3 |

The primary human erythorid cells were treated with parental compound, NaB, HU, or synthesized naphthalimide derivatives (A1, B1, B4, E, E2, or E3) individually. The values of $IC_{50}$ (the half mximal inhibitory concentration), EC (effective concentration), and the ratio of $IC_{50}$ to EC ($IC_{50}$/EC) were calculated, which were used to compare the advantages of these g globin-inducing compounds to hydroxyurea and each other. The g globin induction fold of each compound at its $IC_{50}$ was also shown. ND: non-detectable.

Comparisons of the Therapeutic Potentials Among Naphthalimide Derivatives, S51021, NaB, and HU In order to evaluate the therapeutic potentials of naphthalimide derivatives A2, B1, B4, E1, E2, and E3 in comparison with the parental S51021 as well as other HbF inducers (e.g., NaB and HU), the effective concentration (EC) of each compound was investigated first. The EC values are defined as the concentrations of compounds that induce the γ globin gene expression by 2.3-folds, the fold of the γ globin gene induction by HU at the concentration of $IC_{50}$. The ratio of $IC_{50}$ to EC ($IC_{50}$/EC) is used to determine whether the compound tested has superior therapeutic effect than that of HU (the ratio $IC_{50}$/EC of HU was set as 1).

Although compounds A2 and E1 can activate the γ globin gene expression, their therapeutic potentials were lower than that of HU. In contrast, compounds B1, B4, E2 and E3 exhibit better therapeutic potentials than HU. Of these agents, compound E2 (SS-2394) has the highest $IC_{50}$/EC ratio ($IC_{50}$/EC=2.79) and relatively higher γ globin induction folds (4.0-folds) at the concentration of $IC_{50}$ (Table I). Although none of naphthalimide derivatives showed better $IC_{50}$/EC value than that of S51021, compounds B1, B4, and E2 indeed displayed higher γ globin induction folds than that of S51021 at the concentrations of their $IC_{50}$. It should be noted that compounds B1, B4, E2, and E3 were synthesized as hydrochloride salts and have greatly improved water-solubility (Table 3).

The HbF-inducing Agents Specifically Induce the Embryonic/Fetal Globin Genes Expression.

To evaluate the specificity of S51021, SS-2394, HU, and NaB in mediating globin genes activation, the amounts of individual β-liked globin mRNAs were measured by absolute quantitative RT-PCR. As shown in Table 4, the proportions of the embryonic ε globin and the fetal γ globin mRNAs were both significantly increased by the tested compounds. On the other hand, the proportions of the β globin mRNA were notably reduced after drug-treatment. Among them, the SS-2394 is the most effective fetal globin inducer; increasing the proportion of the fetal γ globin from 7.9% to 11.6% in the drug-treated primary human adult erythroid cells, whereas the proportion of the adult β globin mRNA was reduced from 88.8% to 82.3% (Table 4).

TABLE 4

The expression levels of each β-like globin chains in the primary human erythroid cells

| | ε globin | γ globin | β globin | δ globin |
|---|---|---|---|---|
| Mock | 0.0 ± 0.0% | 7.9 ± 0.8% | 88.8 ± 1.0% | 3.3 ± 0.2% |
| HU | 0.1 ± 0.0% | 11.2 ± 1.1% | 84.2 ± 1.3% | 4.5 ± 0.2% |
| NaB | 0.1 ± 0.0% | 10.8 ± 1.0% | 87.4 ± 1.0% | 1.8 ± 0.1% |
| S51021 | 0.1 ± 0.0% | 10.6 ± 1.2% | 85.6 ± 1.2% | 3.7 ± 0.2% |
| SS-2394 | 0.58 ± 0.1% | 11.6 ± 1.0% | 82.3 ± 1.1% | 5.5 ± 0.4% |

The primary human erythroid cells were treated with HU (145.9 μM), NaB (221.6 μM), S51021 (21.8 μM) or SS2394 (2.3 μM) for 3 days, and the expression levels of each globin mRNA were estimated by absolute quantitative RT-PCR analysis. The proportions of individual β-like globin chains among the total β-like globin mRNA are shown. Data are presented as the mean±SEM, N=3.

Figure 4A:
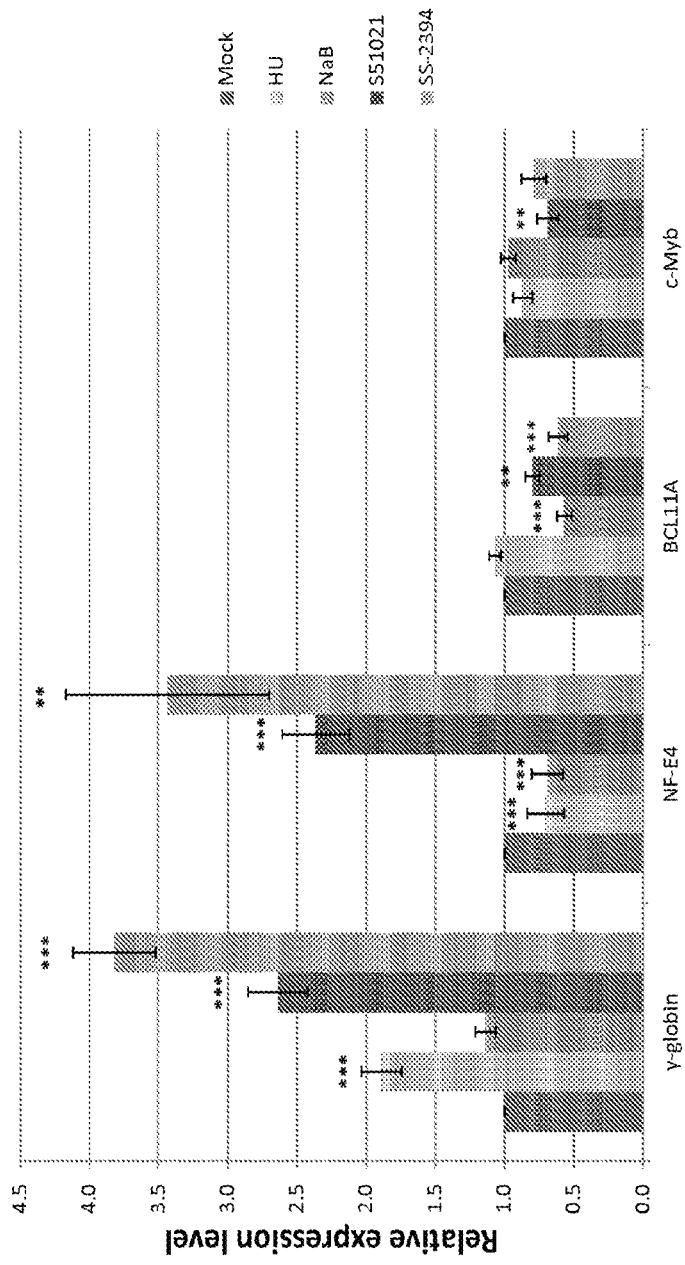
FIG. 4 is a graph showing the expression profiles of the γ globin gene and HbF-related regulators after compounds treatment in the primary human erthroid cells. The primary human erythroid cells were treated with HU (145.9 μM), NaB (221.6 μM), S51021 (21.8 μM) or SS-2394 (2.3 μM) at their IC$_{50}$ for 3 days. (A) Total RNA was extracted, and the expression profiles of γ globin, NF-E4, BCL11A, and c-Myb were analyzed by relative quantitative RT-PCR. Data are presented as the relative expression level in mean±SEM, N=8. (B) Upper panel: For detection of the induction level of γ globin, fifty microgram of total cell lysate was analyzed by western blot analysis using antibody against γ globin, or β-actin. Lower panel: The signal intensity was quantified by an image-analyzing software. The intensity of γ globin expression levels of mock control was set as 1. Data are shown as the mean±SEM, N=5. (C) Upper panel: For detection of the expression level of BCL11A, thirty microgram of total protein was separated by SDS-PAGE electrophoresis, transferred to PVDF membrane, and immunobloted with antibody against BCL11A and β-actin. Lower panel: The signal was quantified by an image-analyzing software. The intensity of the mock control BCL11A levels were set as 1. Data are shown as the mean±SEM, N=5. (D) The HU-nonresponding primary human erythroid cells were treated with HU (145.9 μM), NaB (221.6 μM), S51021 (21.8 μM) or SS-2394 (2.3 μM) for 3 days. Total RNA was extracted, and the expression level of γ globin gene was analyzed by relative quantitative RT-PCR. Data are shown as the mean±SEM, N=3.

Expression Levels of Transcription Activator and Repressor are Modulated by the HbF-inducing Compounds It has been reported that several transcriptional factors, such as NF-E4, c-Myb, and BCL11A, are involved in the regulation of the γ globin gene expression. Zhou et al., Mol Cell Biol. 2000;20(20):7662-7672; Jiang et al., Blood. 2006; 108(3):1077-1083; and Sankaran et al., Science. 2008;322 (5909):1839-1842. NF-E4 was reported to form transcription activation complex, stage selector protein (SSP), which recruited to the γ globin promoter and switched on the γ globin gene expression in the primary human adult erythorid cells. Zhou et al., Mol Cell Biol. 2000;20(20):7662-7672. c-Myb was showed to involve in erythropoiesis and its overexpression in K562 cells inhibited the γ-globin gene expression.[25] More recently, BCL11A was identified to be a developmental stage-specific repressor for controlling the γ globin gene expression. Sankaran et al., Science. 2008;322 (5909):1839-1842. The expression level of full-length BCL11A was increased in parallel with globin switching, suggesting that BCL11A represses the γ globin gene expression in the adult erythroid cells. To clarify the regulatory factors involved in modulating γ globin gene expression in the drug-treated primary human adult erythroid cells, the mRNA levels of the γ globin as well as these transcription factors in response to compounds treatment were determined by the relative quantitative RT-PCR (FIG. 4A). The expression levels of the γ globin mRNA were significantly up-regulated to 1.9-3.7-folds in the cells treated with S51021, SS-2394, or HU, but not NaB (FIG. 4A).

Figure 4B:
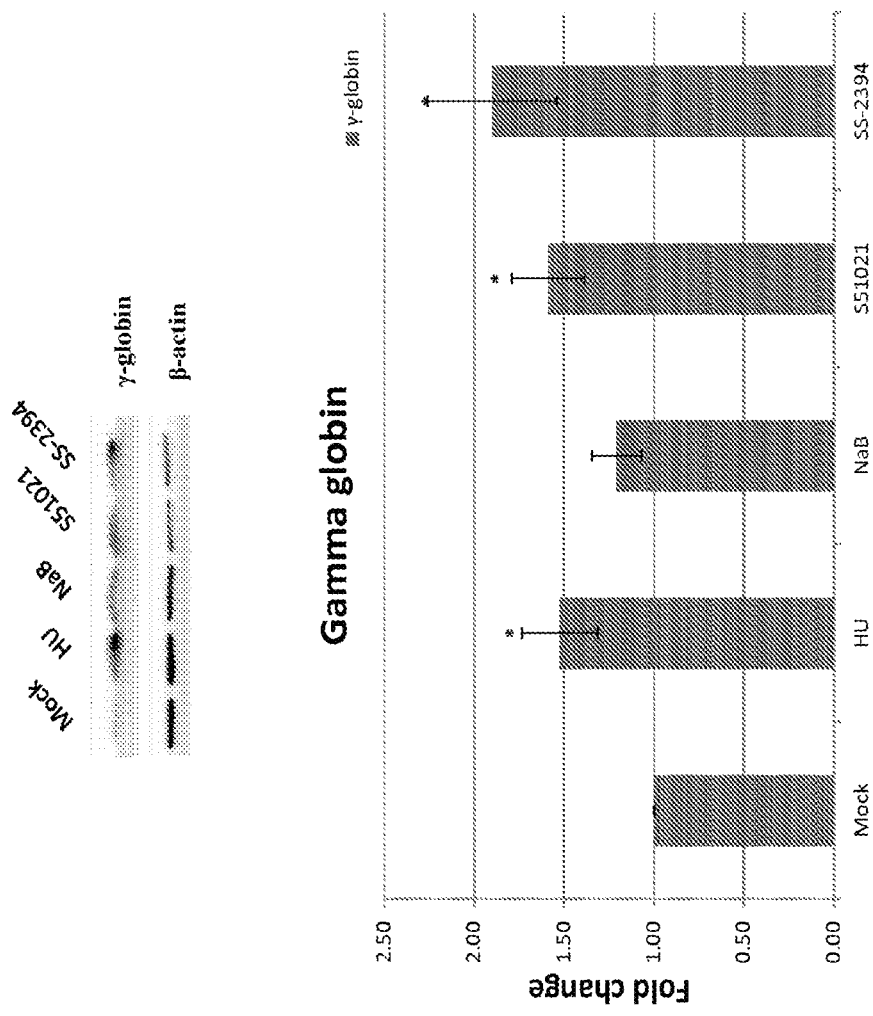
Figure 4C:
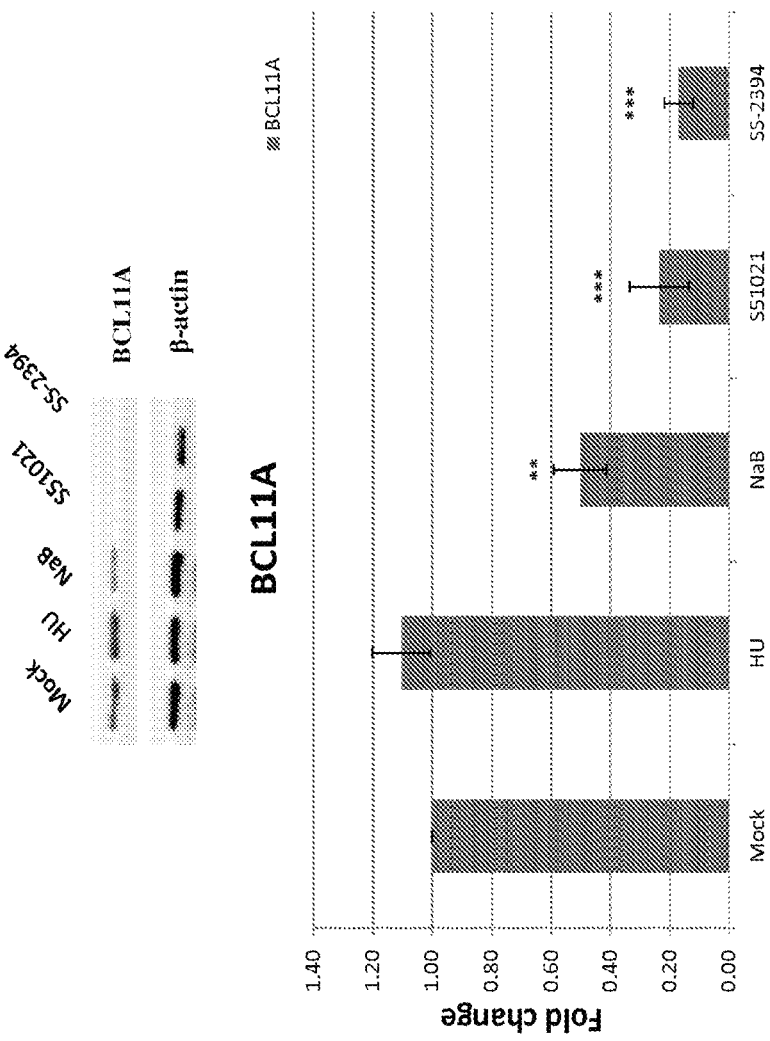
Figure 4D:
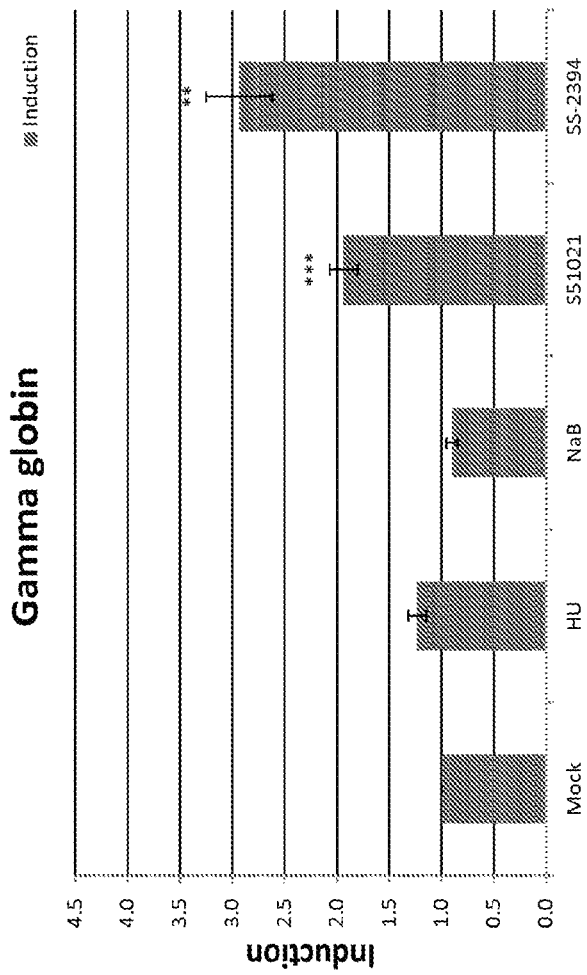

The elevation of protein expression levels of the γ globin chain were further confirmed in the primary human adult erythroid cells treated with S51021 and SS-2394 (FIG. 4B). The expression levels of NF-E4 were increased to 2.4- and 3.4-folds in the cells treated with S51021 and SS-2394, respectively, but decreased to 0.6 fold in the cells treated with either HU or NaB (FIG. 4A). The expression level of c-Myb mRNA was reduced only in the cells treated with S51021 (FIG. 4A). The expression levels of BCL11A mRNA were significantly reduced to 0.8-, 0.6-, and 0.6-folds by S51021, SS-2394, and NaB, respectively (FIG. 4A). A significant reduction of BCL11A protein was also revealed in the primary human adult erythroid cells treated with S51021, SS-2394, or NaB (FIG. 4C). Taken together, these data suggest that the modulations of certain transcription factors, such as NF-E4, c-Myb, and BCL11A, may cooperatively contribute to the γ globin gene induction by the tested compounds. Furthermore, both S51021 and SS-2394 can efficiently induce the re-activation of γ globin gene in the primary human adult erythroid cells, which were not responded upon HU treatment, indicating that S51021 and SS-2394 activate the γ globin gene expression through a distinct mechanism from that of HU (FIG. 4D).

p38 Signaling Pathway is Involved in the γ Globin Gene Activation Triggered by the HbF-inducing Agents.

In addition to these transcription factors, the activation of p38 MAPK signaling pathway was also suggested to mediate the fetal γ globin gene expression in response to NaB or TSA treatment Ramakrishnan et al., *Blood Cells Mol Dis;* 47(1):12-22; and Pace et al., *Exp Hematol.* 2003;31(11): 1089-1096. To verify whether the p38 MAPK signaling pathway is involved in the activation of the γ globin expression by the tested compounds, the phosphorylation status of p38 in these drug-treated erythroid cells was examined by Western blot analysis. Our data showed that all the tested compounds (S51021, SS-2394, HU, and NaB) significantly increased the phosphorylation levels of p38 in parallel with the elevated γ globin protein (FIG. 5), suggesting that the activation of p38 MAPK signaling pathway may, at least in part, contribute to the re-activation of the γ globin gene expression by these HbF-inducing compounds.

S51021 and SS-2394 are not Histone Deacetylase Inhibitors.

Figure 6:
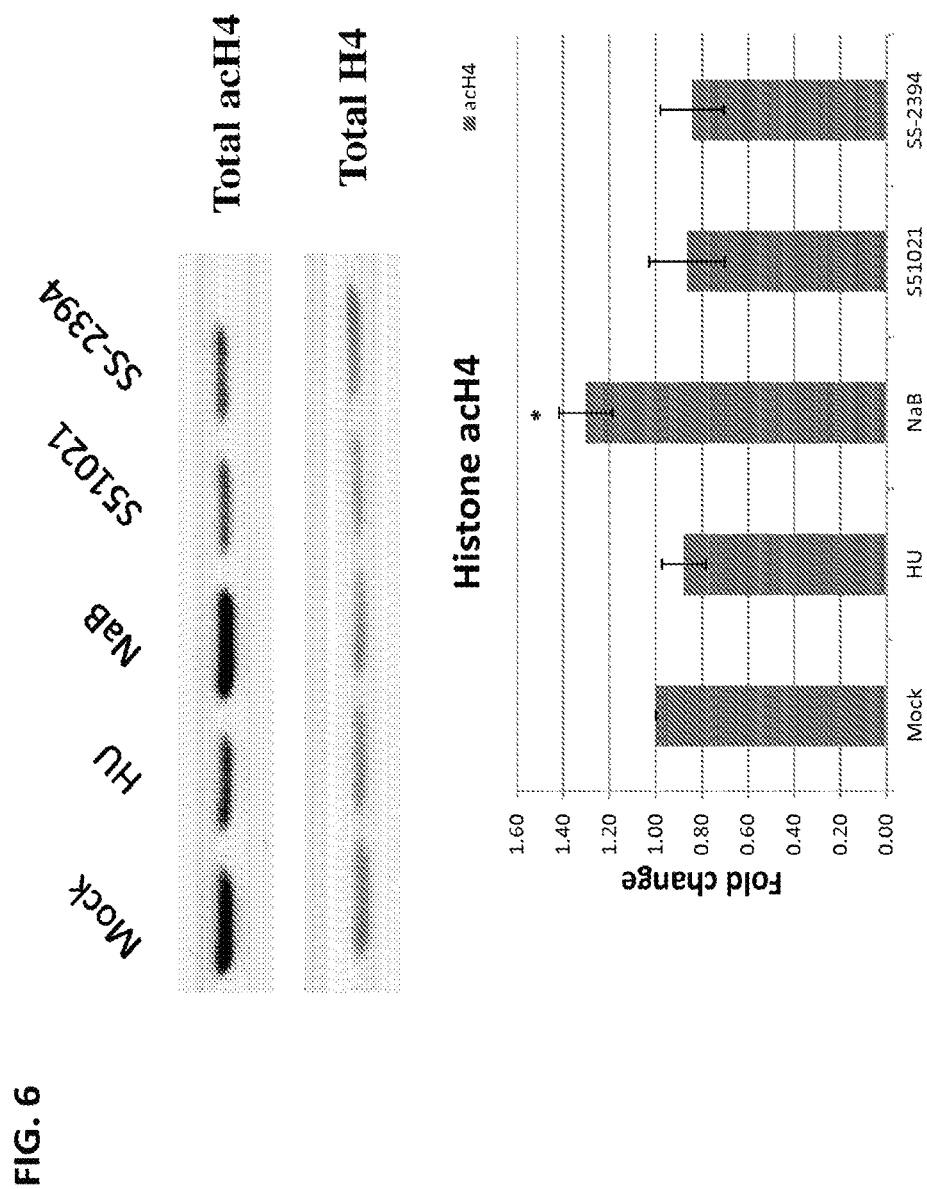
FIG. 6 is a graph showing the acetylation status of histone H4 in primary erythroid cells treating with HU, NaB, S51021 or SS-2394. Upper pnel: To examine the acetylation pattern of histone H4, the primary human erythroid cells were treated with HU (145.9 μM), NaB (221.6 μM), S51021 (21.8 μM) or SS-2394 (2.3 μM) at their IC$_{50}$ for 3 days. Total histones were extracted by histone extraction buffer. Thirty microgram of histone extract was used for western blot analysis and immunobloted with antibody against histone H4 or acetylated histone H4. Lower panel: The signal intensity was quantified by an image-analyzing software. The intensity of mock control was set as 1. Data are shown as the mean±SEM, N=4.
Figure 7:
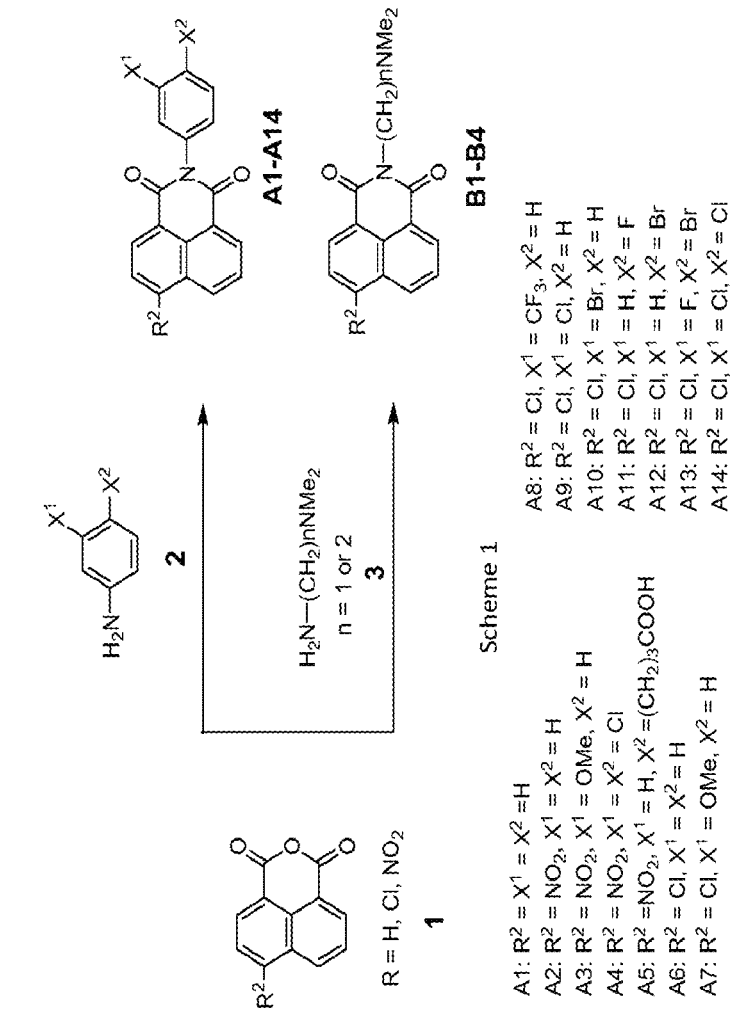
FIG. 7 shows two exemplary synthetic schemes, Scheme 1 and Scheme 2, for synthesing the compounds described herein.
Figure 7:
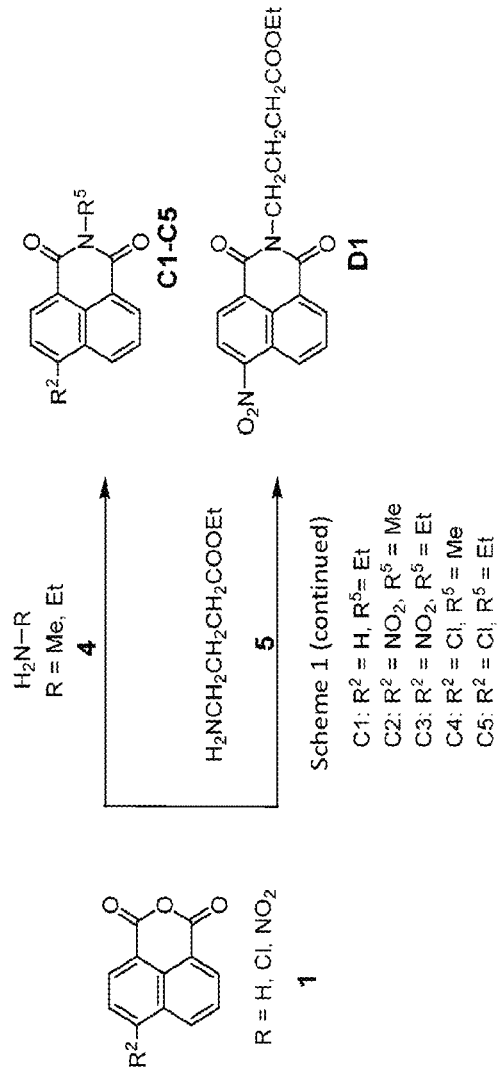
Figure 7:
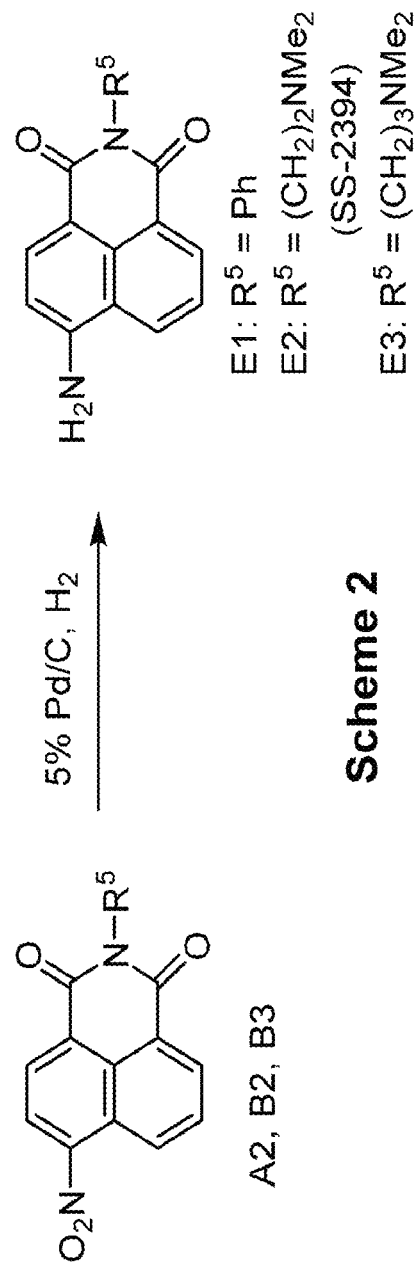

Several HDACi, such as NaB, apicidin, and TSA, have been reported to function as HbF-inducing agents. General believes that the hyper-acetylation of histone by HDACi treatments would contribute to the activation of the γ globin gene expression. To realize whether the epigenetic modification of histone H4 is manipulated by S51021 or SS-2394 treatment, primary human adult erythroid cells were treated with S51021, SS-2394, HU, or NaB for 3 days, and the acetylation status of cellular histone H4 was then analyzed (FIG. 6). Our data showed that the global acetylation status of histone H4 (total acH4) was significantly enhanced in the NaB-treated primary erythroid cells. In the contrast, the amounts of global acetylated histone H4 were not dramatically alternated by S51021, SS-2394 and HU. It indicates that the S51021, SS-2394, and HU are not histone deacetylase inhibitors.

Discussion

Underlying Mechanisms Involved in Reactivation of the γ Globin Gene Expression Mediated by S51021 and SS-2394

Figure 5:
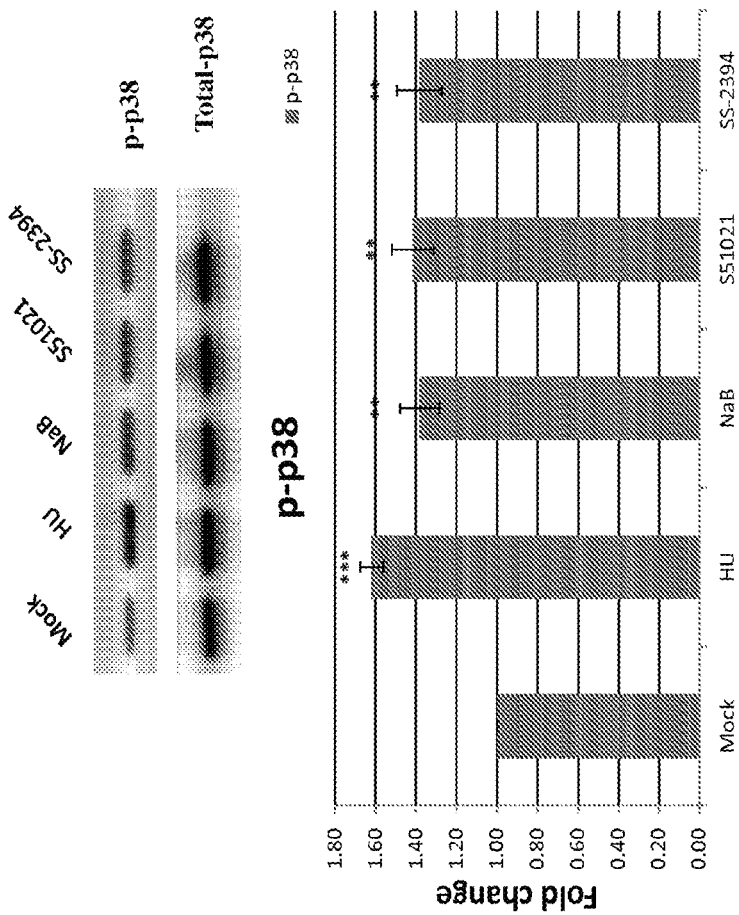
FIG. 5 is a graph showing the phosphorylation status of p38 in primary erythroid cells treating with HU, NaB, S51021, or SS-2394. Upper panel: For detection of the phosphorylation status of p38, twenty microgram of total cell lysate extracted from the primary human erythroid cells treated with HU (145.9 μM), NaB (221.6 μM), S51021 (21.8 μM) or SS-2394 (2.3 μM) was analyzed by Western blot analysis using antibody against p-p38 or p38. Lower panel: The signal intensity was quantified by an image-analyzing software. The intensity of p-p38 levels of mock control cells was set as 1. Data are shown as the mean±SEM, N=5.

Unlike NaB or TSA, S51021 and SS-2394 are not histone deacetylase inhibitors, which did not modulate the global acetylation statues of histone H4 (FIG. 6). Furthermore, it was found that both S51021 and SS-2394 could efficiently re-activate the expression of γ globin gene even in these primary erythroid cells which were not responded to HU (FIG. 4D). All these data demonstrate that the S51021 and SS-2394 belong to a novel class of HbF-inducing agents, which are functional different from these of previous identified compounds including NaB, HU, and TSA. Although the detail mechanisms involved in the γ globin gene induction have not yet been completely clarified, our current studies provide insight into understanding of the underlying mechanism that involves in the re-activation of the γ globin gene expression mediated by S51021 or SS-2394. In the primary human adult erythroid cells, S51021 and SS-2394 treatment significantly down-regulated the expression levels of transcription repressor BCL11A. On the other hand, the expression level of transcription activator NF-E4 was significantly up-regulated by S51021 and SS-2394 treatment (FIG. 4). In addition to these transcription mediators (BCL11A and NF-E4), our data also showed that the phosphorylation level of the p38 was significantly increased by S51021 and SS-2394 (FIG. 5). Moreover, the pre-treatment of p38 MAPK inhibitor SB203580 efficiently abolished the elevation of γ globin gene expression triggered by S51021 and SS-2394 (data not shown). Taken together, it is demonstrated here that re-activation of the γ globin gene expression mediated by S51021 or SS-2394 is a complicated process, in which the modulations of transcription regulators (BCL11A and NF-E4) as well as p38 signaling participate in the regulatory program.

Cell Stress Response Involves in the Elevation of the γ Globin Gene Expression Mediated by HbF-induing Agents.

Previous studies have demonstrated that 1,8-naphthalimides, such as amonafide, function as DNA intercalators and topoisomerase II (topo II) inhibitors in clinical development for the treatment of cancers including acute myeloid leukemia and prostate carcinoma. Norton et al., *Anticancer Drugs.* 2008;19(1):23-36; and Allen et al., *Expert Opinion on Investigational Drugs.* 2011;20(7):995-1003. The newly identified compounds, B1, B4, E2, and E3, which induce HbF, were previous found to exert their anti-cancer ability due to inhibition of topo II (DNA intercalator). Norton et al., *Anticancer Drugs.* 2008;19(1):23-36; Stevenson et al., *J Med Chem.* 1984;27(12):1677-1682; and Zee-Cheng et al., *J Med Chem.* 1985;28(9):1216-1222. Considering the fact that cell growth inhibition and DNA intercalating cause cell stress response, it raises the possibility that cell stress response signaling may contribute to the elevation of γ globin gene expression. Indeed, several cell stress response-inducing agents, such as HU, thalidomide, TSA, and anisomycin, have been reported to activate the γ globin gene expression. Pace B et al., *Exp Hematol.* 2003;31(11):1089-1096; Mabaera R et al, *Exp Hematol.* 2008;36(9):1057-1072; Aerbajinai et al., *Blood.* 2007;110(8):2864-2871; and Cokic V P., *Journal of Clinical Investigation.* 2003;111(2):231-239. It also demonstrated that most of these cell stress response-inducing agents also inhibit cell proliferation and activate the p38 MAPK signaling pathway.[31] As shown in FIG. 5, both S51021 and SS-2394 inhibited cell growth and elevated the phosphorylation status of p38 MAPK at the concentrations of their $IC_{50}$, suggesting that the cell stress response may be involved in the γ globin gene re-activation mediated by S51021 and SS-2394. However, the correlations between cell stress response and modulations of transcription regulators mediated by compound treatment need to be further investigated.

SS-2394 is a Lead Compound for Further Developing Novel HbF-inducing Agent.

A a series of naphthalimide derivatives were synthesized for evaluating their HbF-inducing abilities. These agents were identified via lead optimization by structural modification of S51021. Of these derivatives, SS-2394 was found to have significant effect on increasing elevation of the γ globin mRNA. Although SS-2394 displayed lower $IC_{50}$/EC ratio than that of S51021, several lines of evidence suggest that SS-2394 is a better lead compound for further drug development as an effective agent for treating β-thalassemia and sickle cell disease; First, SS-2394 shows higher γ globin gene induction fold at the concentration of its $IC_{50}$ than that of S51021, suggesting that SS-2394 is a more efficient HbF-inducing agent than S51021 or others (FIG. 4A). Second, SS-2394 contains a symmetric pharmacophore which can be easily synthesized and purified. Third, this agent has greatly improved water-solubility and bioavailability and is more proper for new drug development (Table I). Fourth, SS-2394 displays higher HbF-inducing specificity than other compounds as demonstrated by the observation of the highest proportion of the γ globin mRNA (Table II). In sum, SS-2394, which is not a histone deacetylase inhibitor, was identified as a lead compound for further developing novel agents for treating hemoglobinopathies such as β-thalassemia and sickle cell disease.

Example 2

Examplary Compounds for Treating β-thalassemia and Sickle-cell Disease

SS-2394 shows higher water-solubility than that of the parental compound S51021 but SS-2394 has much higher cytotoxicity than that of S51021 as evident by comparison of their $IC_{50}$. To optimize the biological activity and reduce the cytotoxicity of SS-2394 by structural modification, the core structure of naphthalimide (I) was modified by alternating the carbonyl function of benzo[de]isoquinoline-1,3(2H)-dione; reducing the carbonyl function to hydroxyl derivatives (II), which can be further converted into dehydroxylated derivatives III and IV (Scheme 1). During biological evaluation of SS-2394, it was observed that the C6-amino function in SS-2394 was unstable and can be deaminated or converted into the corresponding C6-hydroxy derivatives. Therefore, various substituent R to the C6 of benzo[de]isoquinolin ring were introduced. The substituent R can be H, $NH_2$, $NHCOCH_3$, NHR', $NR'_2$; wherein R' can be a C1 to C5 alkyl group. The new compounds bear a N,N-dimethylaminoethyl hydrophilic side chain, which can form acid salts with various inorganic acids or organic acids. Thus, the compounds are water soluble compounds and are suitable for biological application.

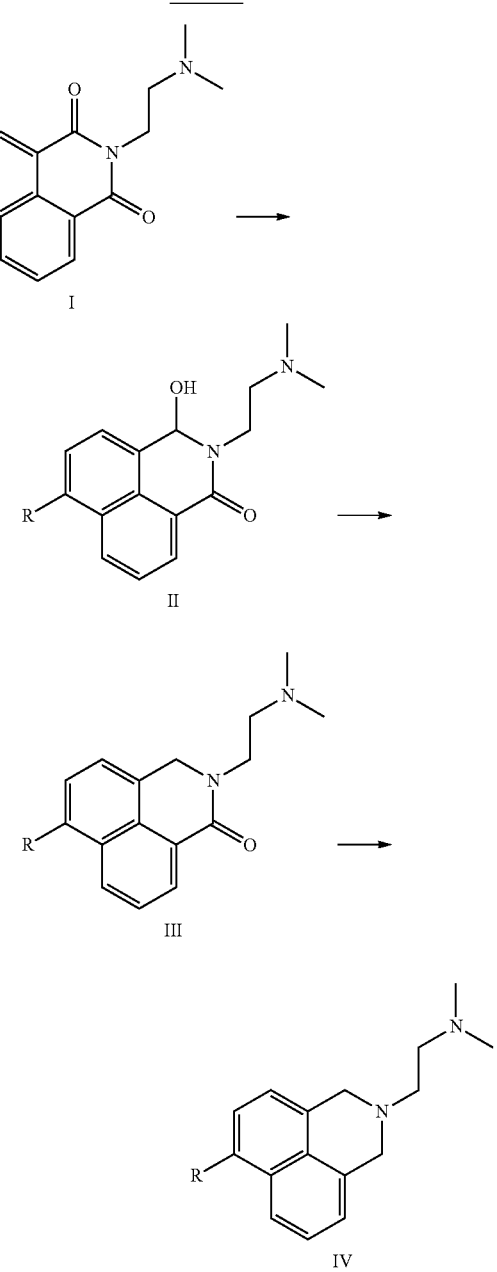

Scheme 1

General Methods

Several representative analogues which have been synthesized are provided in Table 2. The synthetic routes of these derivatives are displayed in Schemes 2, 3 and 4. See also Daffy et al., Chemistry—A European Journal, 1998, 4, 1810-1815; Cheng; Journal of Medicinal Chemistry, 1985, 28, 1216-1222; and Lucatello et al., Bioorganic and Medicinal Chemistry, 2007, 15, 555-562.

Briefly, compound SS-2394 (1) was treated with acetic acid/acetic anhydride to give the N-acetyl derivatives (2, BO-2559), which was converted into 2,3-dihydro-1H-benzo[de]isoquinoline 3 (BO-2566) (Scheme 2). Treatment of 3 with HCl in EtOH gave the 6-amino-2,3-dihydro-1H-benzo[de]isoquinoline (4, BO-2560).

Scheme 2

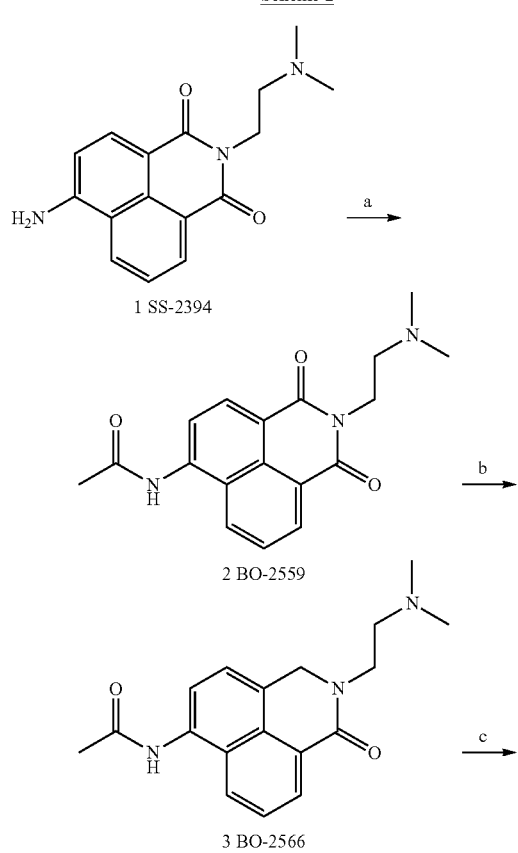

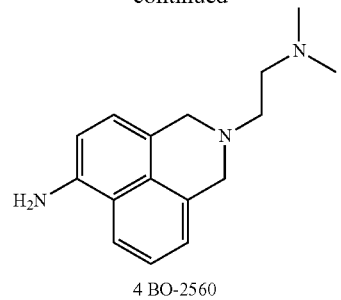

Reaction conditions: a: AcOH/Ac₂O; b: AlCl₃/LiAlH₄/THF; c: HCl/EtOH

To prevent the hydrolysis of C6-NH₂ function, a NMe₂ function was introduced to the C6 position of 2,3-dihydro-1H-benzo[de]isoquinoline-1,3(2H)-dione. Thus, compound 6-NMe₂ substituted derivative BO-2561 (6, Scheme 3) was synthesized from C6-Cl derivative 5 by treating with dimethylamine in DMF in the presence of KOH. Under such reaction conditions, we also obtained C6-OH derivative (7, BO-2562) as the by-product. By following a similar procedure, compound 6 (BO-2561) was converted into 6-NH₂-2,3-dihydro-1H-benzo[e]isoquinoline (8, BO-2563). The C6-NEt derivatives (9, BO-2564) was also synthesized by treating compound 5 with ethylamine. Similarly, compound 9 was further converted into the corresponding benzo[de]isoquinoline (10, BO-2565).

Scheme 3

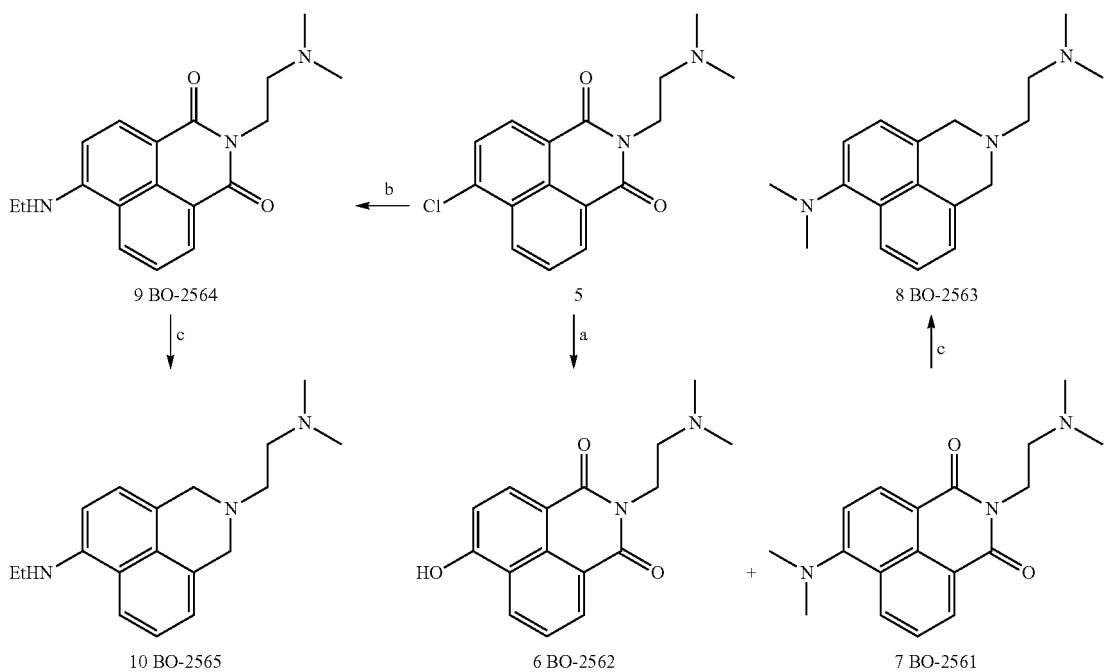

Reaction conditions: a: DMF/KOH; b: N,N-Diethylformamide/KOH; c: AlCl₃/LiAlH₄/THF Compound lacking one or two carbonyl function(s) were synthesized for evaluating their biological activity. As shown in Scheme 4, dione 11 was treated with NaBH$_4$ in ethanol to give mono-hydroxy derivative 12 (BO-2476), which was further converted into mono-carbonyl derivative 13 (BO-2477). Similarly, dione 11 was converted into the corresponding benzo[de]isoquinoline 14 (BO-2563).

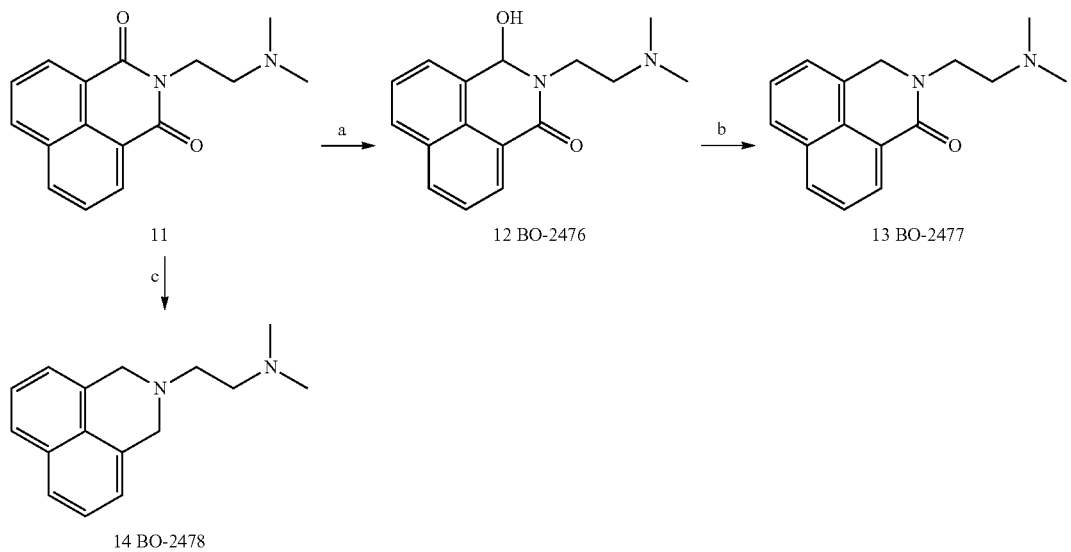

Scheme 4

Reaction conditions: a: NaBH$_4$/EtOH; b: Et$_3$SiH/TFA; c: AlCl$_3$/LiAlH$_4$

Compounds

N-(2-(2-(Dimethylamino)ethyl)-1,3-dioxo-2,3-dihydro-1H-benzo[de]isoquinolin-6-yl)acetamide (2, BO-2559). Daffy et al., Chemistry—A European Journal, 1998, 4, 1810-1815. A suspension of known 6-amino-2-(2-(dimethylamino)-ethyl)-1H-benzo[de]isoquinoline-1,3(2H)-dione (1, 640 mg, 2 mmol) in a mixture of acetic acid (24 mL) and acetic anhydride (3 mL) was refluxed for 45 min. Methanol was added to destroy excess acetic anhydride and then co-evaporated with methanol several times to dryness. The yellow product was collected by filtration to give the desired product N-(2-(2-(dimethylamino)ethyl)-1,3-dioxo-2,3-dihydro-1H-benzo-[de]isoquinolin-6-yl)acetamide (2, BO-2559),[1] 590 mg (90%); mp. 278-279° C.; $^1$H NMR (DMSO-d$_6$) δ 2.30 (3H, s, CH$_3$), 2.87 (6H, s, N(CH$_3$)$_2$), 3.41 (2H, t, J=5.9 Hz, CH$_2$), 4.38 (2H, t, J=5.9 Hz CH$_2$), 7.91 (1H, t, J=8.5 Hz, ArH), 8.34 (1H, d, J=8.2 Hz, ArH), 8.50 (1H, d, J=8.2 Hz, ArH), 8.55 (1H, d, J=6.6 Hz, ArH), 8.79 (1H, d, J=8.6 Hz, ArH), 10.52 (1H, br, NH). HRMS [ES$^+$]: calcd for C$_{18}$H$_{19}$N$_3$O$_3$, 325.3618 [M+H]$^+$, found 326.1500.

2-(2-(Dimethylamino)ethyl)-2,3-dihydro-1H-benzo[de]isoquinolin-6-amine (4, BO-2560). LiAlH$_4$ (20 mg, 3 mmol) was added portionwise to a stirring suspension of AlCl$_3$ (85 mg, 0.62 mmol) in dry THF (10 mL) in an ice-water bath under Argon and stirred for 10 min. N-(2-(2-(dimethylamino)ethyl)-1,3-dioxo-2,3-dihydro-1H-benzo[de]isoquinolin-6-yl)acetamide (2, 163 mg, 0.5 mmol) was added portionwise to the above suspension. The reaction mixture was stirred at room temperature for 20 min and then heated to 40° C. for 1 hr. The reaction mixture was poured into ice-water and the solid was removed by filtration through a pad of Celite. The filtrates were evaporated to dryness under reduced pressure and the residue was dissolved in ethanol (50 mL) and then HCl$_{(conc)}$ (0.5 mL) and then evaporated to dryness. The solid product was recrystallized from ethanol to give 2-(2-(dimethylamino)ethyl)-2,3-dihydro-1H-benzo[d]-isoquinolin-6-amine (4, BO-2560), 101 mg (78%); mp. 253-254° C.; $^1$H NMR (DMSO-d$_6$) δ 2.86 (6H, s, N(CH$_3$)$_2$), 3.70 (4H, s, 2×CH$_2$), 4.65-4.97 (4H, s, 2×CH$_2$), 6.65 (1H, d, J=7.8 Hz, ArH), 7.28 (1H, d, J=7.8 Hz, ArH), 7.42 (1H, d, J=7.1 Hz, ArH), 7.49 (1H, t, J=7.8 Hz, ArH), 8.22 (1H, d, J=8.3 Hz, ArH), 10.83 (2H, br, NH$_2$). HRMS [ES$^+$]: calcd for C$_{16}$H$_{21}$N$_3$, 255.3580 [M+H]$^+$, found 256.1814.

2-(2-(dimethylamino)ethyl)-6-hydroxy-1H-benzo[de]isoquinoline-1,3(2H)-dione (6, BO-2562)[2] and 6-(dimethylamino)-2-(2-(dimethylamino)ethyl)-1H-benzo[de]isoquinoline-1,3(2H)-dione (7, BO-2561). A solution of 6-chloro-2-(2-(dimethylamino)ethyl)-1H-benzo-[de]isoquinoline-1,3(2H)-dione (5, 1.5 g, 5 mmol) and KOH (1.12 g, 20 mmol) in 10 mL of DMF was heated at reflux for 45 min. The solvent was then evaporated in vacuo to dryness. The residue was chromotographered on a silica gel column (4×20 cm) using CHCl$_3$:MeOH (100:2 v/v) as the eluent. The first main product eluated was collected to give 6-(dimethylamino)-2-(2-(dimethyl-amino)ethyl)-1H-benzo[de]isoquinoline-1,3(2H)-dione (7, BO-2561), 795 mg (50%), mp. 198-199° C. $^1$H NMR (DMSO-d$_6$) δ 2.89 (6H, s, N(CH$_3$)$_2$), 3.12 (6H, s, N(CH$_3$)$_2$), 3.44 (2H, t, J=5.9 Hz, CH$_2$), 4.38 (2H, t, J=5.9 Hz, CH$_2$), 7.24 (1H, d, J=7.8 Hz, ArH), 7.79 (1H, t, J=7.9 Hz, ArH), 8.37 (1H, d, J=8.4 Hz, ArH), 8.50 (1H, d, J=7.2 Hz, ArH), 8.56 (1H, d, J=8.4 Hz, ArH). HRMS [ES$^+$]: calcd for C$_{18}$H$_{21}$N$_3$O$_2$, 311.3782 [M+H]$^+$, found 312.1061).

The second product eluated was collected to give 2-(2-(dimethylamino)ethyl)-6-hydroxy-1H-benzo[de]isoquinoline-1,3(2H)-dione (6) (Daffy et al., Chemistry—A European Journal, 1998, 4, 1810-1815) 160 mg (11%); mp. 202-204° C.; $^1$H NMR (DMSO-d$_6$) δ 2.38 (6H, s, N(CH$_3$)$_2$), 2.71 (2H, t, J=8.3 Hz, CH$_2$), 4.19 (2H, t, J=8.3 Hz, CH$_2$), 6.77 (1H, d, J=8.5 Hz, ArH), 7.56 (1H, t, J=7.7 Hz, ArH), 8.18 (1H, d, J=8.5 Hz, ArH), 8.37 (1H, d, J=7.2 Hz, ArH), 8.48 (1H, d, J=8.1 Hz, ArH). HRMS [ES$^+$]: calcd for $C_{16}H_{16}N_2O_3$, 284.3098 [M+H]$^+$, found 285.1240.

2-(2-(Dimethylamino)ethyl)-N,N-dimethyl-2,3-dihydro-1H-benzo[de]isoquinolin-6-amine (8, BO-2563). LiAlH$_4$ (20 mg, 3 mmol) was added portionwise to a stirring suspension of AlCl$_3$ (85 mg, 0.62 mmol) in 10 mL of THF in an ice-water bath under Argon for 10 min. 6-(dimethylamino)-2-(2-(dimethylamino)ethyl)-1H-benzo[de]-isoquinoline-1,3(2H)-dione (7, 311 mg, 1 mmol) was added portionwise. The reaction mixture was allowed to stir at room temperature and then heated to 40° C. for 1 h. The reaction mixture was poured into ice-water and filtered through a pad of Celite. The filtrate were evaporated to dryness under reduced pressure. The solid product was recrystallized from EtOH to give 2-(2-(dimethylamino)ethyl)-N,N-dimethyl-2,3-dihydro-1H-benzo[de]isoquinolin-6-amine (8, BO-2563), 184 mg (65%), mp. 251-252° C.; $^1$H NMR (DMSO-d$_6$) δ 2.89 (6H, s, N(CH$_3$)$_2$), 2.95 (6H, s, N(CH$_3$)$_2$), 3.94 (4H, S, 2×CH$_2$), 4.71 (2H, S, CH$_2$), 4.76 (2H, S, CH$_2$), 7.36 (1H, d, J=7.2 Hz, ArH), 7.46 (1H, d, J=7.8 Hz, ArH), 7.52 (1H, d, J=7.2 Hz, ArH), 7.66 (1H, t, J=7.8 Hz, ArH), 8.19 (1H, d, J=8.5 Hz, ArH). HRMS [ES$^+$]: cald for $C_{18}H_{25}N_3$, 283.4112 [M+H]$^+$, found 284.2129.

2-(2-(Dimethylamino)ethyl)-6-(ethylamino)-1H-benzo[de]isoquinoline-1,3(2H)-dione (9, BO-2564). A solution of 6-chloro-2-(2-(dimethylamino)ethyl)-1H-benzo[de]isoquinoline-1,3(2H)-dione (1.8 g, 6 mmol), and KOH (1.68 g, 30 mmol) in 4 mL of N,N-diethylformamide was refluxed for 2 hr. The solvent was evaporated to dryness. The residue was chromotographer on silica gel (6×20 cm) using CHCl$_3$: methanol 100:4 as eluant to give syrup product 2-(2-(dimethylamino)ethyl)-6-(ethylamino)-1H-benzo[de]isoquinoline-1,3(2H)-dione (9, BO-2564), 313 mg (10%); mp. 253-4° C.; $^1$H NMR (DMSO-d$_6$) δ1.30 (3H, t, J=7.1 Hz, CH$_2$CH$_3$), 2.20 (6H, s, N(CH$_3$)$_2$), 2.48.(2H, t, J=6.9 Hz, CH$_2$), 3.42 (2H, q, J=7.1 Hz, CH$_2$CH$_3$) 4.13 (2H, t, J=6.9 Hz, CH$_2$), 6.79 (1H, d, J=8.5 Hz, ArH), 7.68 (1H, t, J=7.9 Hz, ArH), 7.74 (1H, br, NH), 8.28 (1H, d, J=8.5 Hz, ArH), 8.42 (1H, d, J=9.0 Hz, ArH), 8.44 (1H, d, J=7.3 Hz, ArH), 8.69 (1H, d, J=8.5 Hz, ArH). HRMS [ES$^+$]: calcd for $C_{18}H_{21}N_3O_2$, 311.3782 [M+H]$^+$, found 312.1814.

2-(2-(dimethylamino)ethyl)-N-ethyl-2,3-dihydro-1H-benzo[de]isoquinolin-6-amine (10, BO-2565). A suspension of AlCl$_3$(85 mg, 0.62 mmol) in 10 mL of THF was added portionwise LiAlH$_4$ (20 mg, 3 mmol) at ice-water bath under Argon for 10 min. 2-(2-(dimethylamino)ethyl)-6-(ethylamino)-1H-benzo[de]isoquinoline-1,3(2H)-dione (170 mg, 0.5 mmol) was added portionwise at ice-water. It was stirred at room temperatur and then heated to 40° C. for 1 hr. The reaction mixture was poured into ice-water. The solid was removed by a pad of Celite. The filtrates were evaporated to dryness. The product was recrystallized from EtOH/HCl to give 2-(2-(dimethyl-amino)ethyl)-N-ethyl-2,3-dihydro-1H-benzo[de]isoquinolin-6-amine, 38 mg (24%), mp. 239-240° C.; $^1$H NMR (DMSO-d$_6$) δ1.30 (3H, t, J=7.0 Hz, CH$_2$CH$_3$), 2.87 (6H, s, N(CH$_3$)$_2$), 3.27 (2H, q, J=7.0 Hz, CH$_2$CH$_3$), 3.69 (4H, brs, 2×CH$_2$), 4.87 (4H, brs, 2×CH$_2$), 6.61 (1H, d, J=7.3 Hz, ArH), 7.29 (1H, d, J=7.7 Hz, ArH), 7.49 (1H, br, NH), 7.62 (1H, t, J=7.7 Hz, ArH), 7.98 (1H, d, J=8.2 Hz, ArH), 8.20 (1H, d, J=8.4 Hz, ArH). HRMS [ES$^+$]: calcd for $C_{18}H_{25}N_3$, 283.4112 [M+H]$^+$, found 284.3225.

2-(2-(Dimethylamino)ethyl)-3-hydroxy-2,3-dihydro-1H-benzo[de]isoquinolin-1-one (12, BO-2476). NaBH$_4$ (0.37 g, 10 mmol) was added portionwise to a solution of 2-(2-(dimethylamino)ethyl)-1H-benzo[de]isoquinoline-1,3(2H)-dione (11, 0.27 g, 1 mmol) in EtOH/Water (20 mL, v/v:10/1). The mixture was stirred overnight at room temperature. After the completion of the reaction, the reaction mixture was evaporated under reduced pressure to dryness. The solid residue was triturated with water and extracted with CH$_2$Cl$_2$ (100 mL×3).The combined organic extracts were dried over Na$_2$SO$_4$ and evaporated to dryness and the solid was recrystallized from Haxen/CH$_2$Cl$_2$ to afford the desired product 2-(2-(dimethylamino)ethyl)-3-hydroxy-2,3-dihydro-1H-benzo[de]isoquinolin-1-one (12, BO-2476), 0.24 g (89%); mp. 129-130° C.; $^1$H NMR (DMSO-d$_6$) δ 2.26 (6H, s, N—Me$_2$), 2.48-2.45 (1H, m, CH), 2.72-2.68 (1H, m, CH), 3.71-3.65 (1H, m, CH), 3.97-3.92 (1H, m, CH), 6.15 (1H, s, CH—OH), 7.71-7.64 (3H, m, ArH), 7.78 (1H, s, CH—OH, exchangeable), 8.03 (1H, d, J=7.1 Hz, ArH), 8.19 (1H, d, J=8.2 Hz, ArH), 8.24 1H, d, J=7.1 Hz, ArH). HRMS [ES$^+$]: cald for $C_{16}H_{18}N_2O_2$, 270.3262 [M+H]$^+$, found 271.2231.

2-(2-(Dimethylamino)ethyl)-2,3-dihydro-1H-benzo[de]isoquinolin-1-one (13, BO-2477). To a solution of 2-(2-(dimethylamino)ethyl)-3-hydroxy-2,3-dihydro-1H-benzo[de]isoquinolin-1-one (12, 0.27 g, 1 mmol) in CH$_2$Cl$_2$ (10 mL) were added triethylsilane (0.48 mL, 3 mmol) and TFA (4 mL). The reaction mixture was stirred overnight at room temperature. After the completion of, solvent was evaporated under reduced pressure to dryness and the residue was triturated with saturated NaHCO$_3$ solution and then extracted with CH$_2$Cl$_2$. The combined organic extracts were dried over Na$_2$SO$_4$ and evaporated to dryness. The solid residue was recrystallized from Haxen/CH$_2$Cl$_2$ to 2-(2-(dimethylamino)ethyl)-2,3-dihydro-1H-benzo[de]isoquinolin-1-one (13, BO-2477), 0.22 g, 86%; mp. 253-254° C.; $^1$H NMR (DMSO-d$_6$) δ 2.86 (6H, s, N—Me$_2$), 3.48-3.45 (2H, m, CH$_2$), 4.02-3.99 (2H, m, CH$_2$), 5.14 (2H, s, CH$_2$), 7.48 (1H, d, J=7.0 Hz, ArH), 7.66-7.59 (2H, m, ArH), 7.91 (1H, d, J=8.2 Hz, ArH), 8.16-8.12 (2H, m, ArH). HRMS [ES$^+$]: cald for $C_{16}H_{18}N_2O$, 254.3269 [M+H]$^+$, found 255.1169.

2-(1H-Benzo[de]isoquinolin-2(3H)-yl)-N,N-dimethylethan-1-amine (14, BO-2478). Lucatello et al., *Bioorganic and Medicinal Chemistry*, 2007, 15, 555-562. To suspension of AlCl$_3$ (0.17 g, 1.25 mmol) in anhydrous THF was added LiAlH$_4$ (0.24 g, 6 mmol) followed by slow addition of 2-(2-(dimethyl-amino)ethyl)-1H-benzo[de]isoquinoline-1,3 (2H)-dione (11, 0.27 g, 1 mmol) at 0° C. The mixture was then refluxed for 3 h, cooled to 0° C. and then poured into ice/THF cautiously. The solid separated was collected by filtration and the filtrate was extracted with CH$_2$Cl$_2$. The organic layer was separated and dried over anhydrous Na$_2$SO$_4$ and evaporated to dryness afforded the final product. The final product was then converted in to HCl salt by treating with EA/HCl to give 2-(1H-benzo[de]isoquinolin-2(3H)-yl)-N,N-dimethylethan-1-amine (14, BO-2478), 0.215 g (78%); mp. 208-209° C.; $^1$H NMR (CDCl$_3$-d$_6$) δ 2.28 (6H, s, N—(CH$_3$)$_2$), 2.62-2.58 (2H, m, CH$_2$), 2.78-2.75 (2H, m, CH$_2$), 4.02 (2H, s, CH$_2$), 7.19 (2H, d, J=8.6 Hz, ArH), 7.41-7.36 (2H, m, ArH), 7.68 (2H, d, J=10.3 Hz, ArH). HRMS [ES$^+$]: cald for $C_{16}H_{21}N_2Cl$, 276.8043 [M+H]$^+$, found 277.7241.

Biological Activity

Figure 8:
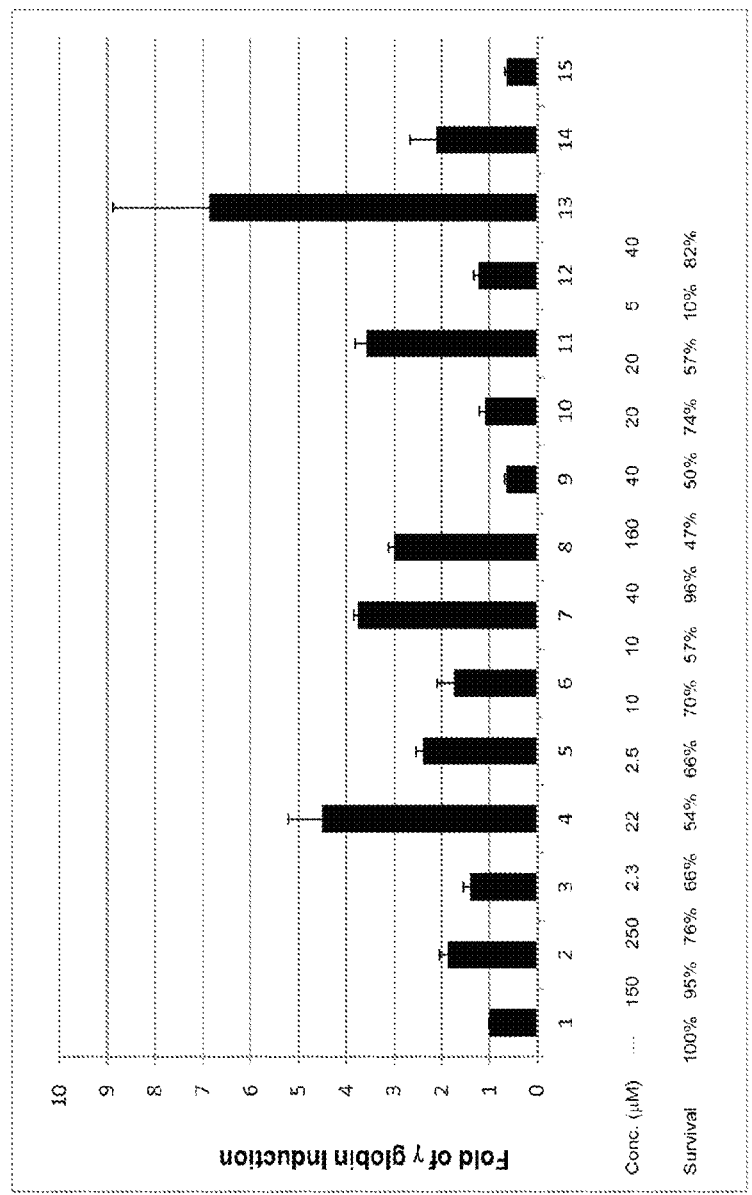
FIG. 8 shows the effect of γ globin-induction and cytotoxicity against primary erythroid cells by the representative analogues of 2,3-dihydro-1H-benzo[de]isoquinoline.

All the newly synthesized compounds were evaluated for their γ globin-inducing abilities. FIG. 8 shows the effect of γ globin-induction and cytotoxicity against primary erythroid cells by the representative analogues of 2,3-dihydro-1H-benzo[de]isoquinoline (line 1: mock control; line 2: hydroxyurea (HU); line 3: sodium butyrate (NaB); line 4: SS-2394; line 5: 551021; line 6: BO-2562; line 7: BO-2561; line 8: BO-2559; line 9: BO-2566; line 10: BO-2563, line 11: BO-2560; line 12: BO-2565; line 13: BO-2477; line 14: BO-2476; line 15: BO-2478. The tested concentrations of each compound and the survival rates of the primary erythroid cells after 2 days of compound treatment are listed at the bottom of the graph.

As shown in FIG. 8, the newly synthesized compounds BO-2559, BO-2560, BO-2561, BO-2476 and BO-2477 showed significant γ globin-inducing abilities, of which the expression levels of γ globin gene were up-regulated by 2.1-6.9 folds in primary erythroid cells. All these newly identified γ globin-inducing compounds have reduced cytotoxicities with $IC_{50}$ ranging from 5 to 40 μM against primary erythroid cells. Among the compounds tested, compound BO-2477 was shown to have the highest γ globin-inducing activity with relatively lower cytotoxicity.

What is claimed is:

1. A method of inducing γ globin production, comprising: contacting a cell with an effective amount of a compound of formula (I-a):

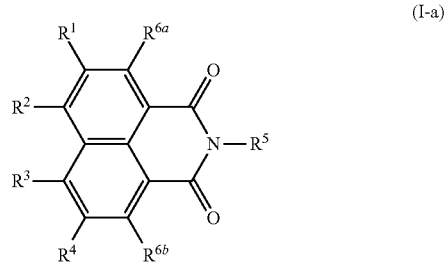

(I-a)

or a pharmaceutically acceptable salt thereof, wherein:
$R^1$, $R^2$, $R^3$, $R^4$, $R^{6a}$, and $R^{6b}$ are each independently selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$;
$R^5$ is hydrogen, optionally substituted alkenyl, optionally substituted alkynyl, optionally substituted heterocyclyl, optionally substituted heteroaryl, or optionally substituted aryl, unsubstituted alkyl, or alkyl substituted with halogen, —$OR^A$, —$N(R_B)_2$, —$C(=O)OR^A$, a monocyclic or bicyclic aryl aromatic ring system with 6-10 carbon atoms, wherein at least one ring is aromatic, —CHO, —CN, or —$NO_2$;
each instance of $R^A$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl; and
each instance of $R^B$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl, or two $R^B$ are taken together with the intervening atoms to form a heterocycle.

2. The method of claim 1, wherein the compound is selected from the group consisting of the compounds of the formula:

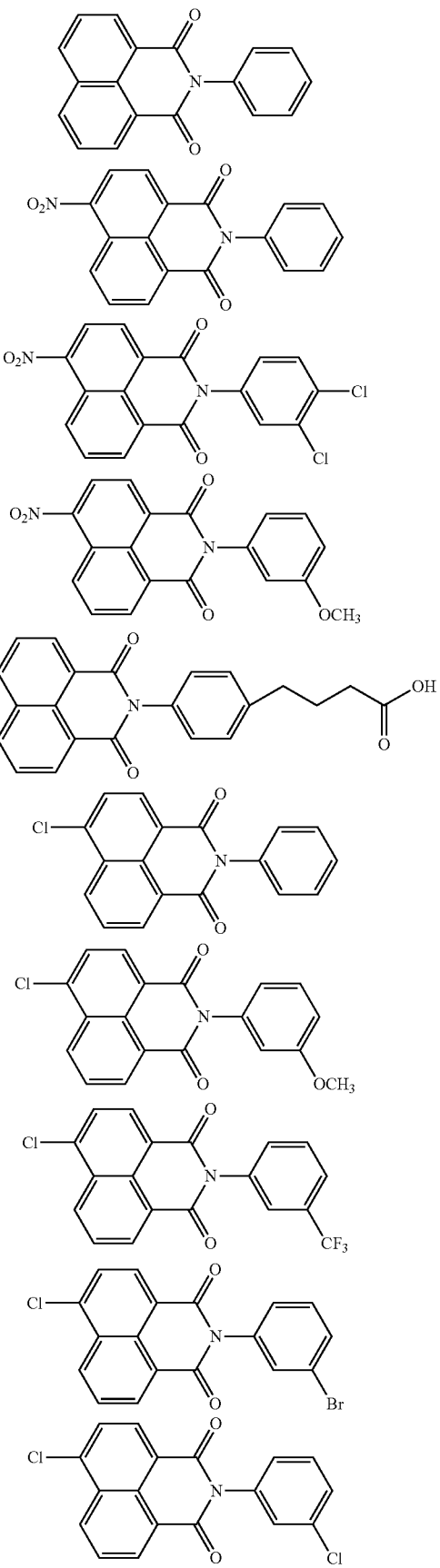

93
-continued
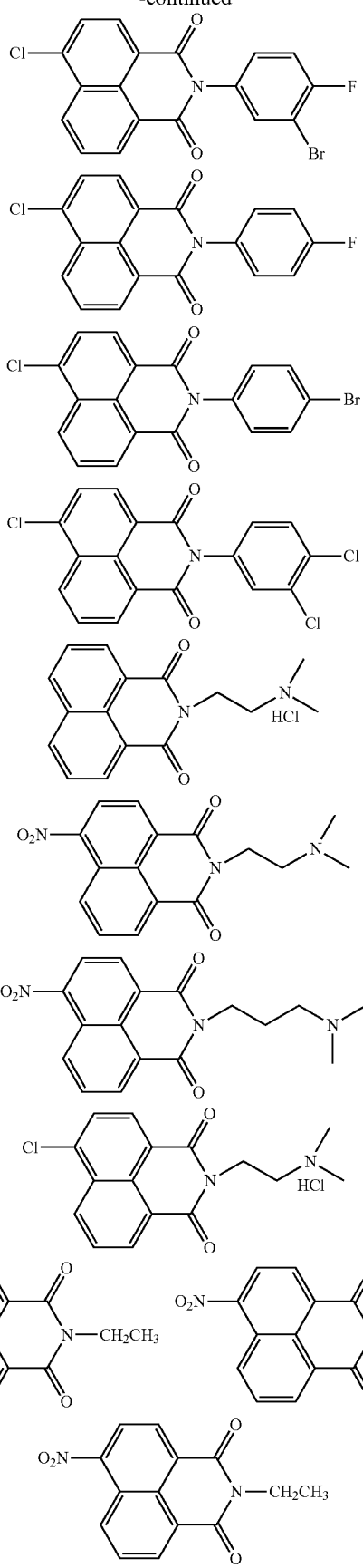
94
-continued
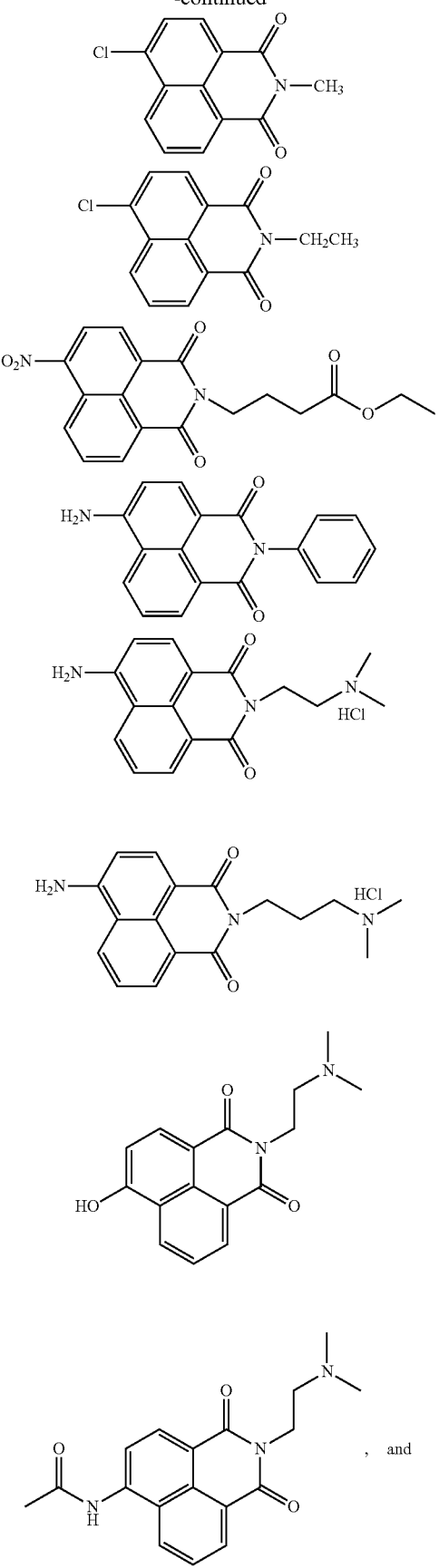
, and

-continued

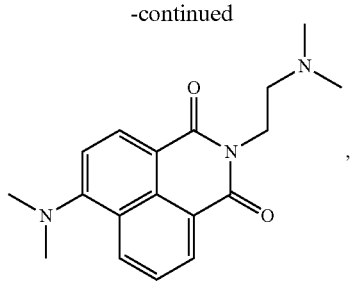

or a pharmaceutically acceptable salt thereof.

3. A method of treating anemia, comprising:
administering to a subject in need thereof an effective amount of a pharmaceutical composition comprising a compound of the formula (I-a):

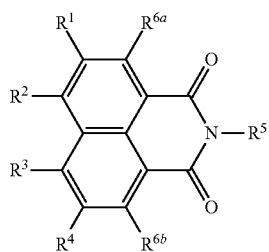

or a pharmaceutically acceptable salt thereof,
wherein:
$R^1$, $R^2$, $R^3$, $R^4$, $R^{6a}$, and $R^{6b}$ are each independently selected from the group consisting of hydrogen, halogen, optionally substituted alkyl, optionally substituted alkenyl, optionally substituted alkynyl, optionally substituted heterocyclyl, optionally substituted heteroaryl, optionally substituted aryl, —$OR^A$, —$OC(O)R^A$, —$SR^A$, —$N(R^B)_2$, —$N(R^A)C(O)R^A$, —$C(O)N(R^B)_2$, —CN, —$NO_2$, —$C(O)R^A$, —$C(O)OR^A$, —$S(O)R^A$, —$SO_2R^A$, —$SO_2N(R^B)_2$, and —$NHSO_2R^B$;
$R^5$ is hydrogen, optionally substituted alkenyl, optionally substituted alkynyl, optionally substituted heterocyclyl, optionally substituted heteroaryl, optionally substituted aryl, unsubstituted alkyl, or alkyl substituted with halogen, —$OR^A$, —$N(R_B)_2$, —$C(=O)OR^A$, a monocyclic or bicyclic aryl aromatic ring system with 6-10 carbon atoms, wherein at least one ring is aromatic, —CHO, —CN, or —$NO_2$;
each instance of $R^A$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl; and
each instance of $R^B$ is independently selected from the group consisting of hydrogen, optionally substituted alkyl, optionally substituted alkenyl, optionally substituted alkynyl, optionally substituted heterocyclyl, optionally substituted heteroaryl, and optionally substituted aryl, or two $R^B$ are taken together with the intervening atoms to form a heterocycle.

4. The method of claim 3, wherein the subject suffers from or is suspected of having β-thalassemia.

5. The method of claim 3, wherein the subject suffers from or is suspected of having sickle cell anemia.

6. The method of claim 3, wherein the pharmaceutical composition is administered orally.

7. The method of claim 3, wherein the pharmaceutical composition is administered parentally.

8. The method of claim 3, wherein the pharmaceutical composition is administered in combination with an additional therapeutic agent.

9. The method of claim 1, wherein the contacting step is performed by administering an effective amount of the compound of formula (I-a) or a pharmaceutically acceptable salt thereof to a subject in need thereof.

10. The method of claim 9, wherein the subject suffers from or is suspected of having anemia.

11. The method of claim 10, wherein the subject suffers from or is suspected of having β-thalassemia.

12. The method of claim 10, wherein the subject suffers from or is suspected of having sickle cell anemia.

13. The method of claim 9, wherein the pharmaceutical composition is administered orally.

14. The method of claim 9, wherein the pharmaceutical composition is administered parentally.

15. The method of claim 9, wherein the pharmaceutical composition is administered in combination with an additional therapeutic agent.

16. The method of claim 3, wherein the compound is selected from the group consisting of the compounds of the formula:

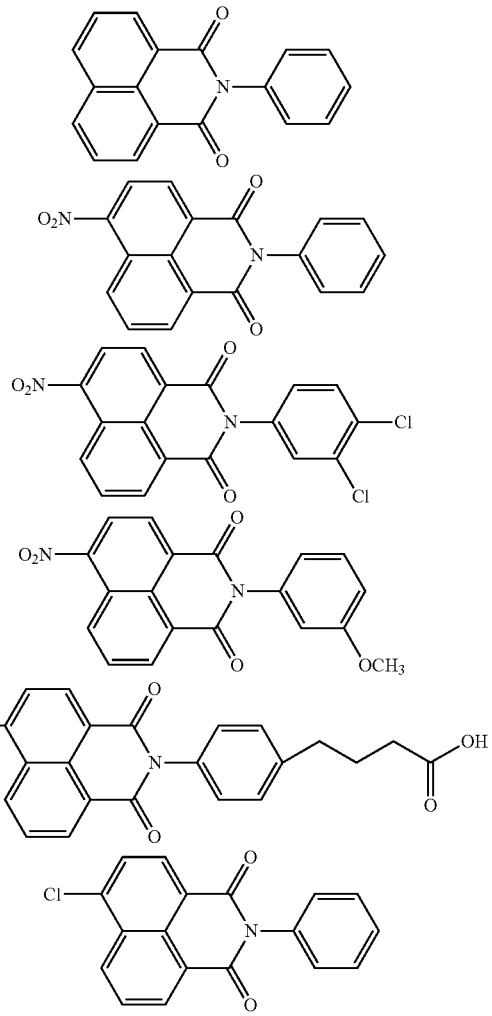

97
-continued
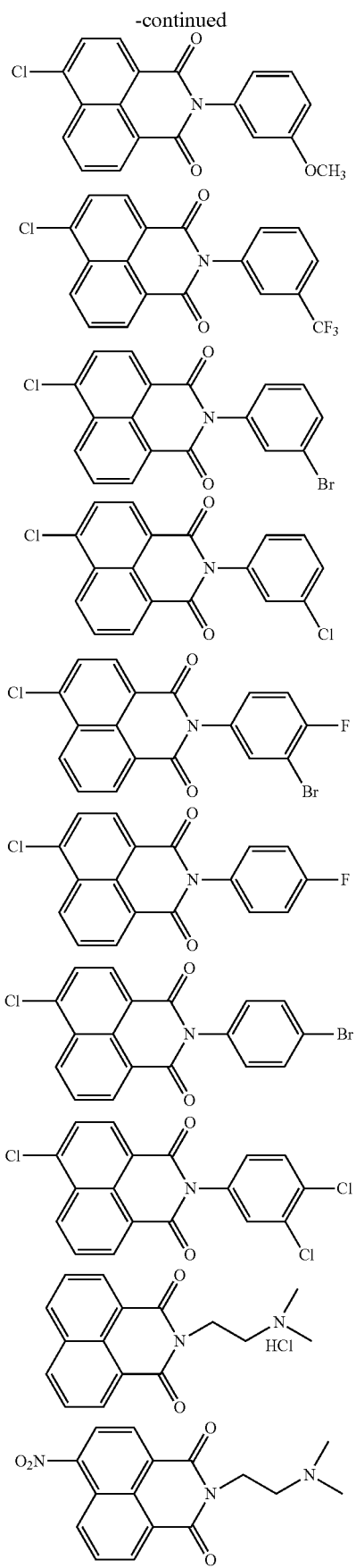
98
-continued
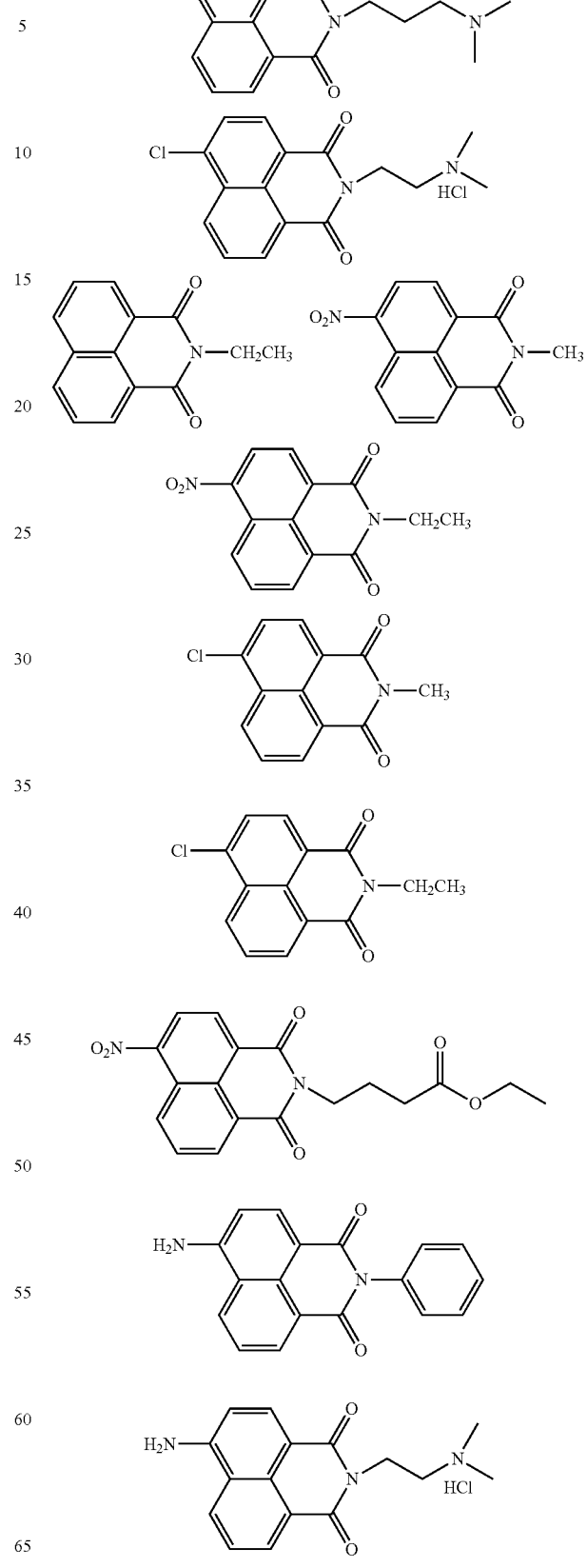

99
-continued
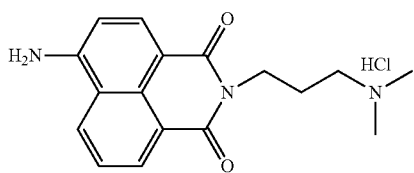
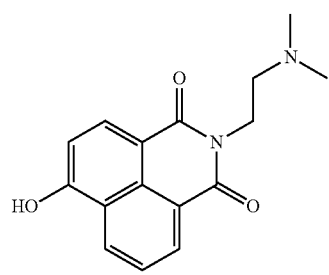
100
-continued
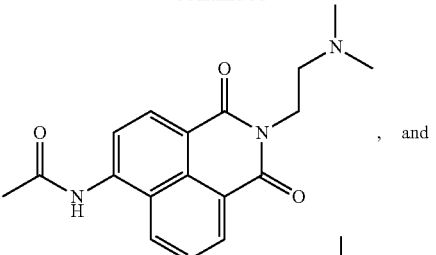, and
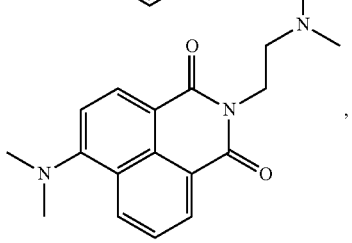,
or a pharmaceutically acceptable salt thereof.
* * * * *